(12) United States Patent
Iwanowicz et al.

(10) Patent No.: US 6,919,335 B2
(45) Date of Patent: Jul. 19, 2005

(54) HETEROCYCLES THAT ARE INHIBITORS OF IMPDH ENZYME

(75) Inventors: Edwin J. Iwanowicz, West Windsor, NJ (US); Scott H. Watterson, Pennington, NJ (US); T. G. Murali Dhar, Newtown, PA (US); William J. Pitts, Newtown, PA (US); Henry H. Gu, Bordentown, NJ (US)

(73) Assignee: Bristol-Myers Squibb Co., Princeton, NJ (US)

( * ) Notice: Subject to any disclaimer, the term of this patent is extended or adjusted under 35 U.S.C. 154(b) by 0 days.

(21) Appl. No.: 09/840,503

(22) Filed: Apr. 23, 2001

(65) Prior Publication Data

US 2002/0040022 A1 Apr. 4, 2002

Related U.S. Application Data

(60) Provisional application No. 60/199,420, filed on Apr. 24, 2000.

(51) Int. Cl.[7] .................. C07D 413/00; C07D 265/36; C07D 215/16; A61K 31/445; A61K 31/495

(52) U.S. Cl. .................... 514/230.5; 546/153; 544/105; 544/128; 544/363; 514/312; 514/235.2; 514/253.07

(58) Field of Search .......................... 546/153; 514/312, 514/230.5, 235.2, 253.07; 544/105, 128, 363

(56) References Cited

U.S. PATENT DOCUMENTS

| | | | |
|---|---|---|---|
| 3,495,009 A | 2/1970 | Tronche et al. | 424/283 |
| 4,686,234 A | 8/1987 | Nelson et al. | 514/469 |
| 4,725,622 A | 2/1988 | Nelson et al. | 514/469 |
| 4,727,069 A | 2/1988 | Nelson et al. | 514/211 |
| 4,753,935 A | 6/1988 | Nelson et al. | 514/233.5 |
| 4,786,637 A | 11/1988 | Allison et al. | 514/233.5 |
| 4,808,592 A | 2/1989 | Nelson et al. | 514/233.5 |
| 4,861,776 A | 8/1989 | Nelson et al. | 514/233.5 |
| 4,868,153 A | 9/1989 | Allison et al. | 514/470 |
| 4,948,793 A | 8/1990 | Allison et al. | 514/233.5 |
| 4,952,579 A | 8/1990 | Nelson et al. | 514/233.5 |
| 4,959,387 A | 9/1990 | Nelson et al. | 524/469 |
| 4,992,467 A | 2/1991 | Allison et al. | 514/464 |
| 5,247,083 A | 9/1993 | Knox et al. | 544/153 |
| 5,380,879 A | 1/1995 | Sjogren | 549/310 |
| 5,444,072 A | 8/1995 | Patterson et al. | 514/320 |
| 5,665,583 A | 9/1997 | Collart et al. | 435/191 |
| 5,807,876 A | 9/1998 | Armistead et al. | 514/374 |

FOREIGN PATENT DOCUMENTS

| WO | WO94/01105 | 1/1994 |
|---|---|---|
| WO | WO94/12184 | 6/1994 |
| WO | WO97/40028 | 10/1997 |
| WO | WO98/40381 | 9/1998 |
| WO | WO 03/035066 | 5/2003 |

OTHER PUBLICATIONS

CAS printout for Yu et al. Chem. Abs. 72:31563, 1970.*
Papageorgiou, Enterohepatic recirculation: a powerful incentive for drug discorry in the inosine monophosphate dehydrogenas field, Mini. Rev. Med. Chem. 1:71–77, 2001.*
Jackson et al., Nature, vol. 256, pp. 331–333, 1975.
Collart et al., J. Biol. Chem., vol. 263, No. 30, pp. 15769–15772, 1988.
Natsumeda et al., J. Biol. Chem. vol. 265, No. 9, pp. 5292–5295, 1990.
Chan et al., Tetrahed. Lett., vol. 39, pp. 2933–2936, 1998.
Lam et al., Tetrahed. Lett., vol. 39, pp. 2941–2944, 1988.
Kuo et al., J. Med. Chem, vol. 36, pp. 1146–1156, 1993.
Toda et al., Heterocycles, vol. 38, No. 9, pp. 2091–2097, 1994.
Kalinin et al., Tetrahedron Lett., vol. 33, No. 3, pp. 373–376, 1992.
Torii et al., Tetrahedron, vol. 49, No. 31, pp. 6773–6784, 1993.
Wang et al., J. Org. Chem., vol. 65, pp. 1889–1891, 2000.
Li et al., J. Med. Chem., vol. 37, pp. 3400–3407, 1994.
Babudri et al., J. Chem. Soc. Perkins Trans. I., pp. 1899–1903, 1984.
Hradil et al., J. Heterocyclic Chem., vol. 36, pp. 141–144, 1999.
Behrman et al., J. Chem. Research(s), pp. 164–165, 1995.
Miyaura et al., Synthetic Communications, 1981, vol. 11, No. 7, 513–519.
Ishiyama et al., J. Org. Chem., 1995, vol. 60, No. 23, 7508–7510.
Chen et al., Synthesis, 1987, 482–483.
Clay et al., Synthesis, 1993, 290–293.
Vysokov et al., Ruissian Journal of Organic Chemistry, 1993, vol. 34, No. 3, 428–433.
Carr et al., The Journal of Biological Chemistry, 1993, vol. 265, No. 36, 27286–27290.
Kalinin, Russian Chemical Reviews, 1991, vol. 60, No. 2, 339–373.

(Continued)

*Primary Examiner*—Richard L. Raymond
(74) *Attorney, Agent, or Firm*—Laurelee A. Duncan; Maureen P. O'Brien

(57) ABSTRACT

Compounds of the formula

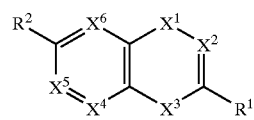

wherein $X^1$ is C(O), —S(O)—, or —S(O)$_2$—;
$X^2$ is $CR^3$ or N; $X^3$ is —NH—, —O—, or —S—;
$X^4$ is $CR^4$ or N; $X^5$ is $CR^5$ or N; and $X^6$ is $CR^6$ or N are useful as inhibitors of IMPDH enzyme. Thus, these compounds can be used as therapeutic agents for IMPDH-associated disorders.

22 Claims, No Drawings

OTHER PUBLICATIONS

Konno et al., The Journal of Biological Chemistry, 1991, vol. 266, No. 1, 506–509.
Canelos et al., Journal Allergy Clin. Immunol., 2001, vol. 107, SIBO Abstracts, Abstract No. 593, p. S180.
Miyaura et al., J. Am. Chem. Soc., 1989, vol. 111, 314–321.
Sui et al., Eur. J. Med. Chem., 1999, vol. 34, 381–387.
Montero et al., Clinica Chemica Acts, 1995, vol. 238, 169–178.
Katritzky et al., Comprehensive Heterocyclic Chemistry, The Structure, Reactions, Synthesis and Uses of Heterocyclic Compounds, Pergamon Press, New York, First Edition, 1984.
Katritzky et al., Comprehensive Heterocyclic Chemistry II, A Review of the Literature 1982–1995, The Structure, Reactions, Synthesis, and Use of Heterocyclic Compounds, Pergamon Press, New York, 1996.
Larock, Comprehensive Organic Transformations, A Guide to Functional Group Preparations, pp. 389–439, VCH Publishers, Inc., 1989.
Hudlicky, Reductions in Organic Chemistry, Second Edition, ACS Monograph 188, pp. 91–101, American Chemical Society, Washington, DC, 1996.
Padwa, 1,3–Dipolar Cycloaddition Chemistry, vol. 2, John Wiley and Sons, New York, NY, 1984.
Padwa, 1,3–Dipolar Cycloaddition Chemistry, vol. 1, John Wiley and Sons, New York, NY, 1984.
Hudlicky, Oxidations in Organic Chemistry, ACS Monograph 186, American Chemical Society, Washington, DC, 1990.
Carey et al., Advanced Organic Chemisty, Third Edition, Part B: Reactions and Synthesis, Plenum Press, New York, NY, 1990.
Hagen et al., Pharmazie, vol. 46, 531–532, 1991.
Chemical Abstracts, vol. 122, No. 5, Jan. 30, 1995, Abstract No. 55994v.
Singh et al., J. Indian Chem. Soc., vol. 71, No. 3, 159–160, 1994.
Chemical Abstract, vol. 122, No. 5, Jan. 30, 1995, Abstract No. 55978t.
Levin et al., Bioorg. Med. Chem. Lett., vol. 4, No. 15, 1819–1824, 1994.
Chemical Abstracts, vol. 116, No. 11, Mar. 16, 1992, Abstract No. 106220a.

* cited by examiner

HETEROCYCLES THAT ARE INHIBITORS OF IMPDH ENZYME

This application claims priority from U.S. application Ser. No. 60/199,420 filed Apr. 24, 2000.

FIELD OF THE INVENTION

The present invention relates to novel compounds which inhibit IMPDH, and to methods of making such compounds. The invention also encompasses pharmaceutical compositions containing these compounds. The compounds and pharmaceutical compositions of the invention are particularly well suited for inhibiting IMPDH enzyme activity and, consequently, can be advantageously used as therapeutic agents for IMPDH-associated disorders. This invention also relates to methods for inhibiting the activity of IMPDH using the compounds of this invention alone or in combination with other pharmaceutically active agents.

BACKGROUND OF THE INVENTION

Inosine monophosphate dehydrogenase (IMPDH) has been shown to be a key enzyme in the regulation of cell proliferation and differentiation. Nucleotides are required for cells to divide and replicate. In mammals, nucleotides may be synthesized through one of two pathways: the de novo synthesis pathway or the salvage pathway. The extent of utilization of each pathway is dependent on the cell type. This selectivity has ramifications with regard to therapeutic utility as described below.

IMPDH is involved in the de novo synthesis of guanosine nucleotides. IMPDH catalyzes the irreversible NAD-dependent oxidation of inosine-5'-monophosphate ("IMP") to xanthosine-5'-monophosphate ("XMP"), Jackson et al., *Nature* 256:331–333 (1975).

IMPDH is ubiquitous in eukaryotes, bacteria and protozoa. The prokaryotic forms share 30–40% sequence identity with the human enzyme.

Two distinct cDNA's encoding IMPDH have been identified and isolated. These transcripts are labeled type I and type II and are of identical size (514 amino acids). Collart et al., *J. Biol. Chem.* 263:15769–15772 (1988); Natsumeda et al., *J. Biol. Chem.* 265:5292–5295 (1990); and U.S. Pat. No. 5,665,583 to Collart et al. These isoforms share 84% sequence identity. IMPDH type I and type II form tetramers in solution, the enzymatically active unit.

B and T-lymphocytes depend on the de novo, rather than salvage pathway, to generate sufficient levels of nucleotides necessary to initiate a proliferative response to mitogen or antigen. Due to the B and T cell's unique reliance on the de novo pathway, IMPDH is an attractive target for selectively inhibiting the immune system without also inhibiting the proliferation of other cells.

Immunosuppression has been achieved by inhibiting a variety of enzymes. Examples include: phosphatase calcineurin (inhibited by cyclosporin and FK-506); dihydroorotate dehydrogenase (DHODase), an enzyme involved in the biosynthesis of pyrimidines (inhibited by leflunomide and brequinar); the kinase FRAP (inhibited by rapamycin); and the heat shock protein hsp70 (inhibited by deoxyspergualin).

Inhibitors of IMPDH have also been described in the art. WO 97/40028 and U.S. Pat. No. 5,807,876 describe a class of urea derivatives that possess a common urea backbone. WO 98/40381 describes a series of heterocyclic substituted anilines as inhibitors of IMPDH.

U.S. Pat. Nos. 5,380,879 and 5,444,072 and PCT publications WO 94/01105 and WO 94/12184 describe mycophenolic acid ("MPA") and some of its derivatives as potent, uncompetitive, reversible inhibitors of human IMPDH type I and type II. MPA has been demonstrated to block the response of B and T-cells to mitogen or antigen. Immunosuppressants, such as MPA and derivatives of MPA, are useful drugs in the treatment of transplant rejection and autoimmune disorders, psoriasis, inflammatory diseases, including, rheumatoid arthritis, tumors and for the treatment of allograft rejection. These are described in U.S. Pat. Nos. 4,686,234, 4,725,622, 4,727,069, 4,753,935, 4,786,637, 4,808,592, 4,861,776, 4,868,153, 4,948,793, 4,952,579, 4,959,387, 4,992,467, and 5,247,083.

The combination of agents for prevention and/or treatment of IMPDH-associated disorders, especially allograft rejection, has been investigated. In one study, it was observed that cyclic AMP agonists, such as Rolipram (Schering AG), a Type 4 Phosphodiesterase Inhibitor (PDE4) and immunomodulator, synergized with IMPDH inhibitor MPA by a cAMP- and IMPDH-dependent dependent mechanism. (P. A. Canelos, L. M. Lichtenstein, S. K. Huang, D. M. Essayan, J. Allergy and Clinical Immunology, 107:593 (2001)). The chemical structure of Rolipram is [4-[3-(cyclopentyloxy)-4-methoxy-phenyl]-2-pyrrolidinone]. The investigators found that cyclic AMP agonists, such as the PDE4 inhibitor Rolipram (Rol), markedly downregulated antigen-specific T lymphocyte responses through their effects on a variety of signaling pathways. In the study, the potential for a very low concentration of Rol ($10^{-7}$ M, approximate $IC_{10}$) to synergize with a variety of immunosuppressive agents used for the prevention and/or treatment of allograft rejection was defined. While little or no synergistic effect on inhibition of antigen-induced proliferation (assessed by $^3$H Thymidine incorporation) could be demonstrated with calcineurin antagonists (cyclosporine and tacrolimus), sirolimus, or corticosteroids, a marked synergistic effect was demonstrated with MPA, the active metabolite of mycophenolate mofetil (CellCept, Roche). This effect was statistically significant over 4 orders of magnitude ($10^{-6}$ to $10^{-9}$ M). This synergism was recapitulated with dibuteryl-cAMP ($2\times10^{-6}$ M, approximate $IC_{10}$) and inhibited with the use of H-9, suggesting a mechanism involving both cAMP and protein kinase A.

Since MPA is a selective, uncompetitive, and reversible inhibitor of IMPDH, a key enzyme in the purine salvage pathway, the potential for cAMP-mediated cross-talk at this locus was further investigated. It was found that gene expression for IMPDH types I and II (assessed by RT-PCR) remained unaffected by the administration of rolipram, MPA, or both at low and high concentrations. However, functional reversal of the synergistic effect was demonstrated with the use of deoxyguanosine, a specific antagonist of MPA on IMPDH (% inhibition of proliferation 81±16 vs. 35±12, p<0.05). Finally, despite a marked synergistic effect on inhibition of proliferation, no significant downregulation in the generation of proinflammatory cytokines (IL-2, IL-4, and IFN, each assessed by RT-PCR), could be detected with the administration of Rol $10^{-7}$ M, MPA $10^{-8}$ M, or the combination. It was concluded that Rol demonstrates marked synergy with MPA by a cAMP-and IMPDH-dependent mechanism. The utility of this combination of agents for the induction of T cell tolerance was suggested by the specificity of the observed effect for proliferation, without the abrogation of cytokine generation and early signaling processes.

Tiazofurin, ribavirin and mizoribine also inhibit IMPDH. These nucleoside analogs are competitive inhibitors of IMPDH; however, these agents inhibit other NAD dependent enzymes. This low level of selectivity for IMPDH limits the therapeutic application of tiazofurin, ribavirin and mizoribine. Thus, new agents which have improved selectivity for IMPDH would represent a significant improvement over the nucleoside analogs.

Mycophenolate mofetil, sold under the trade name CELLCEPT, is a prodrug which liberates MPA in vivo. It is approved for use in preventing acute renal allograft rejection following kidney transplantation. The side effect profile limits the therapeutic potential of this drug. MPA is rapidly metabolized to the inactive glucuronide in vivo. In humans, the blood levels of glucuronide exceed that of MPA. The glucuronide undergoes enterohepatic recycling causing accumulation of MPA in the bile and subsequently in the gastrointestinal w tract. This together with the production of the inactive glucuronide effectively lowers the drug's in vivo potency, while increasing its undesirable gastrointestinal side effects.

Unlike type I, type II mRNA is preferentially upregulated in human leukemic cell lines K562 and HL-60. Weber, *J. Biol. Chem.* 266: 506–509 (1991). In addition, cells from human ovarian tumors and leukemic cells from patients with chronic granulocytic, lymphocytic and acute myeloid leukemias also display an up regulation type II mRNA. This disproportionate increase in IMPDH activity in malignant cells may be addressed through the use of an appropriate IMPDH inhibitor. IMPDH has also been shown to play a role in the proliferation of smooth muscle cells, indicating that inhibitors of IMPDH may be useful in preventing restenosis or other hyperproliferative vascular diseases.

IMPDH has been shown to play a role in viral replication in some viral cell lines. Carr, *J. Biol. Chem.* 268:27286–27290 (1993). The IMPDH inhibitor VX-497, is currently being evaluated for the treatment of hepatitis C virus in humans. Ribavirin has also been used in the treatment of hepatitis C and B viruses and when used in combination with interferon an enhancement in activity was observed. The IMPDH inhibitor ribavirin is limited by its lack of a sustained response in monotherapy and broad cellular toxicity.

There remains a need for potent selective inhibitors of IMPDH with improved pharmacological properties, physical properties and fewer side effects. Such inhibitors would have therapeutic potential as immunosuppressants, anti-cancer agents, anti-vascular hyperproliferative agents, anti-inflammatory agents, antifungal agents, antipsoriatic and anti-viral agents. The compounds of the present invention are effective inhibitors of IMPDH.

SUMMARY OF THE INVENTION

It is an object of the present invention to provide heterocyclic compounds of the following formula (I), their enantiomers, diastereomers, tautomers and pharmaceutically acceptable salts, prodrugs and solvates thereof, for use as IMPDH inhibitors:

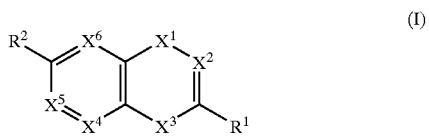

including isomers, enantiomers, diastereomers, tautomers, pharmaceutically acceptable salts, prodrugs and solvates thereof wherein:

$X^1$ is C=O, —S(O)—, or —S(O)$_2$—;

$X^2$ is $CR^3$ or N;

$X^3$ is —NH—, —O—, or —S—;

$X^4$ is $CR^4$ or N;

$X^5$ is $CR^5$ or N;

$X^6$ is $CR^6$ or N;

$R^1$ is alkyl, substituted alkyl, alkenyl, substituted alkenyl, alkynyl, substituted alkynyl, $NR^8R^9$, $SR^{20}$, cycloalkyl, substituted cycloalkyl, aryl, substituted aryl, heterocycloalkyl, or heteroaryl;

$R^2$ is halogen, cyano, nitro, hydroxy, oxo (double bond is no longer present between $CR^2$ and $X^6$), $SR^7$, $S(O)R^7$, $SO_2R^7$, $SO_2NR^8R^9$, $CO_2R^7$, $C(O)NR_8R^9$, or heteroaryl;

$R^3$ is hydrogen, hydroxy, halogen, cyano, $CO_2R^7$, $NR^8R^9$, alkyl, substituted alkyl, alkenyl, substituted alkenyl, alkynyl, substituted alkynyl, cycloalkyl, substituted cycloalkyl, aryl, substituted aryl, heterocycloalkyl or heteroaryl;

$R^4$, $R^5$, and $R^6$ are independently selected from the group consisting of hydrogen, halogen, nitro, cyano, O—$R^7$, $NR^8$ $R^9$, $SR^7$, $S(O)R^7$, $SO_2R^7$, $SO_3R^7$, $SO_2NR^8R^9$, $CO_2R^7$, $C(O)$ $NR^8R^9$, C(O)alkyl, C(O)substituted alkyl, alkyl, substituted alkyl, alkenyl, substituted alkenyl, alkynyl and substituted alkynyl;

$R^7$, $R^{10}$, and $R^{11}$, are independently selected from the group consisting of hydrogen, alkyl, substituted alkyl, alkenyl, alkynyl, cycloalkyl, substituted cycloalkyl, C(O) alkyl, C(O)substituted alkyl, C(O)cycloalkyl, C(O) substituted cycloalkyl, C(O)aryl, C(O)substituted aryl, C(O) Oalkyl, C(O)Osubstituted alkyl, C(O)heterocycloalkyl, C(O)heteroaryl, aryl, substituted aryl, heterocycloalkyl and heteroaryl;

$R^8$ and $R^9$ are independently selected from the group consisting of hydrogen, alkyl, substituted alkyl, cycloalkyl, substituted cycloalkyl, alkenyl, alkynyl, C(O)alkyl, C(O) substituted alkyl, C(O)cycloalkyl, C(O)substituted cycloalkyl, C(O)aryl, C(O)substituted aryl, C(O)Oalkyl, C(O)Osubstituted alkyl, C(O)heterocycloalkyl, C(O) heeroaryl, aryl, substituted aryl, heterocycloalkyl, and heteroaryl or $R^8$ and $R^9$ taken together with the nitrogen atom to which they are attached complete a heterocycloalkyl or heteroaryl ring;

$R^{20}$ is alkyl, substituted alkyl, cycloalkyl, aryl, substituted aryl, heteroaryl or heterocycloalkyl;

$R^3$ and $R^1$ may be taken together with the carbon atoms to which they are attached to form a monocyclic or substituted monocyclic ring system of 5 or 6 carbon atoms; and $R^4$ and $R^5$ may be joined together by the chain —O—CH$_2$—O—or —O—CH$_2$—CH$_2$—O—.

It is another object of the present invention to provide pharmaceutical compositions containing the IMPDH inhibitor compounds of the invention.

It is yet another object of the present invention to provide methods for treating inosine monophosphate dehydrogenase associated disorders using the IMPDH inhibitor compounds of the invention. It is a further object of the present invention to provide methods for treating treating inosine monophosphate dehydrogenase associated disorders and preventing or treating allograft rejection using the IMPDH inhibitor compounds of the invention and phosphodiesterase Type 4 inhibitors.

Detailed Description of the Invention

[1] Thus in a first embodiment, the present invention provides a method of treating inosine monophosphate dehydrogenase associated disorders comprising: administering a therapeutically effective amount of a compound of formula (I)

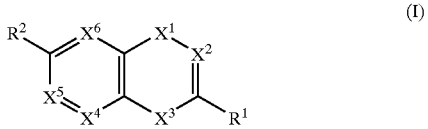

(I)

including isomers, enantiomers, diastereomers, tautomers, pharmaceutically acceptable salts, prodrugs and solvates thereof wherein:

$X^1$ is C=O, —S(O)—, or —S(O)$_2$—;
$X^2$ is $CR^3$ or N;
$X^3$ is —NH—, —O—, or —S—;
$X^4$ is $CR^4$ or N;
$X^5$ is $CR^4$ or N;
$X^6$ is $CR^5$ or N;
$X^6$ is $CR^6$ or N;
$R^1$ is alkyl, substituted alkyl, alkenyl, substituted alkenyl, alkynyl, substituted alkynyl, $NR^8R^9$, $SR^{20}$, cycloalkyl, substituted cycloalkyl, aryl, substituted aryl, heterocycloalkyl, or heteroaryl;

$R^2$ is halogen, cyano, nitro, hydroxy, oxo (double bond is no longer present between $CR^2$ and $X^6$), $SR^7$, $S(O)R^7$, $SO_2R^7$, $SO_2NR^8R^9$, $CO_2R^7$, $C(O)NR^8R^9$, or heteroaryl;

$R^3$ is hydrogen, hydroxy, halogen, cyano, $CO_2R^7$, $NR^8R^9$, alkyl, substituted alkyl, alkenyl, substituted alkenyl, alkynyl, substituted alkynyl, cycloalkyl, substituted cycloalkyl, aryl, substituted aryl, heterocycloalkyl or heteroaryl;

$R^4$, $R^5$, and $R^6$ are independently selected from the group consisting of hydrogen, halogen, nitro, cyano, O—$R^7$, $NR^8R^9$, $SR^7$, $S(O)R^7$, $SO_2R^7$, $SO_3R^7$, $SO_2NR^8R^9$, $CO_2R^7$, $C(O)NR^8R^9$, C(O)alkyl, C(O)substituted alkyl, alkyl, substituted alkyl, alkenyl, substituted alkenyl, alkynyl and substituted alkynyl;

$R^7$, $R^{10}$, and $R^{11}$, are independently selected from the group consisting of hydrogen, alkyl, substituted alkyl, alkenyl, alkynyl, cycloalkyl, substituted cycloalkyl, C(O) alkyl, C(O)substituted alkyl, C(O)cycloalkyl, C(O) substituted cycloalkyl, C(O)aryl, C(O)substituted aryl, C(O)Oalkyl, C(O)Osubstituted alkyl, C(O)heterocycloalkyl, C(O)heteroaryl, aryl, substituted aryl, heterocycloalkyl and heteroaryl;

$R^8$ and $R^9$ are independently selected from the group consisting of hydrogen, alkyl, substituted alkyl, cycloalkyl, substituted cycloalkyl, alkenyl, alkynyl, C(O)alkyl, C(O) substituted alkyl, C(O)cycloalkyl, C(O)substituted cycloalkyl, C(O)aryl, C(O)substituted aryl, C(O)Oalkyl, C(O)Osubstituted alkyl, C(O)heterocycloalkyl, C(O) heteroaryl, aryl, substituted aryl, heterocycloalkyl, and heteroaryl or $R^8$ and $R^9$ taken together with the nitrogen atom to which they are attached complete a heterocycloalkyl or heteroaryl ring;

$R^{20}$ is alkyl, substituted alkyl, cycloalkyl, aryl, to substituted aryl, heteroaryl or heterocycloalkyl;

$R^3$ and $R^1$ may be taken together with the carbon atoms to which they are attached to form a monocyclic or substituted monocyclic ring system of 5 or 6 carbon atoms; and $R^4$ and $R^5$ may be joined together by the chain —O—CH$_2$—O— or —O—CH$_2$—CH$_2$—O—.

[2] In a preferred embodiment, the present invention provides a method of treating inosine monophosphate dehydrogenase associated disorders comprising: administering a therapeutically effective amount of a compound of formula (II)

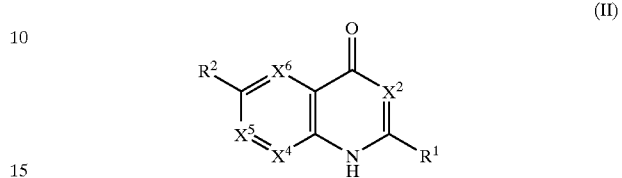

(II)

including isomers, enantiomers, diastereomers, tautomers, pharmaceutically acceptable salts, prodrugs and solvates thereof wherein:

$R^2$ is a monocyclic substituted or unsubstituted heteroaryl group.

[3] In another preferred embodiment, the present invention provides a method of treating inosine monophosphate dehydrogenase associated disorders comprising: administering a therapeutically effective amount of a compound of formula (III)

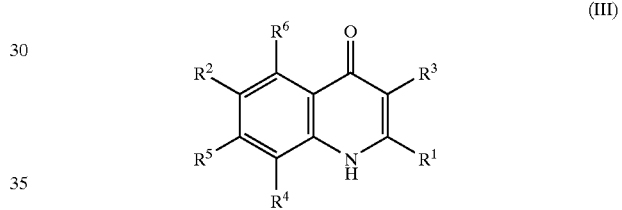

(III)

including isomers, enantiomers, diastereomers, tautomers, pharmaceutically acceptable salts, prodrugs and solvates thereof wherein:

$R^2$ is 4-oxazolyl, substituted 4-oxazolyl, 5-oxazolyl, or substituted 5-oxazolyl;

$R^3$ is hydrogen, hydroxy, $NR^8R^9$, alkyl of 1 to 4 carbons, alkenyl of 2 to 4 carbons, alkynyl of 2 to 4 carbons, substituted alkyl of 1 to 4 carbons, phenyl, substituted phenyl, cycloalkyl of 5 to 7 carbons, substituted cycloalkyl of 5 to 7 carbons, monocyclic heterocycloalkyl and monocyclic heteroaryl;

$R^4$ is hydrogen, halogen, nitro, hydroxy, alkyl of 1 to 4 carbons, cyano, $CF_3$, $OCF_3$, $OCH_3$, $SCH_3$, $S(O)CH_3$, or $S(O)_2CH_3$;

$R^5$ is hydrogen, halogen, nitro, hydroxy, alkyl of 1 to 4 carbons, cyano, vinyl, $CF_3$, $CF_2CF_3$, $CH=CF_2$, $OCH_3$, $OCF_3$, $OCHF_2$, $SCH_3$, $S(O)CH_3$, or $S(O)_2CH_3$; and $R^6$ is hydrogen, halogen, nitro, hydroxy, alkyl of 1 to 4 carbons, cyano, $CF_3$, $OCH_3$, $OCF_3$, $SCH_3$, $S(O)$ $CH_3$, and $S(O)_2CH_3$.

[4] In another preferred embodiment, the present invention provides a method of treating inosine monophosphate dehydrogenase associated disorders comprising: administering a therapeutically effective amount of a compound including isomers, enantiomers, diastereomers, tautomers, pharmaceutically acceptable salts, prodrugs and solvates wherein:

$R^2$ is 4-oxazolyl, substituted 4-oxazolyl, 5-oxazolyl, substituted 5-oxazolyl or heteroaryl;

$R^3$ is hydrogen, hydroxy, halogen, methyl or $NR^8R^9$;

$R^4$ is hydrogen;

R[5] is halogen, methyl, ethyl, substituted alkenyl, alkyne, OMe or OCF$_3$; and R[6] is hydrogen.

[5] In another preferred embodiment, the present invention provides a method of treating inosine monophosphate dehydrogenase associated disorders comprising: administering a therapeutically effective amount of a compound including isomers, enantiomers, diastereomers, tautomers, pharmaceutically acceptable salts, prodrugs and solvates wherein:

R[2] is 4-oxazolyl, substituted 4-oxazolyl, 5-oxazolyl or substituted 5-oxazolyl;

R[3] is hydrogen, hydroxy, halogen or methyl;

R[4] is hydrogen;

R[5] is halogen, methyl or OMe; and

R[6] is hydrogen.

[6] In an even more preferred embodiment, the present invention provides a method of treating inosine monophosphate dehydrogenase associated disorders comprising: administering a therapeutically effective amount of a phosphodiesterase Type 4 inhibitor and a compound of formula (X):

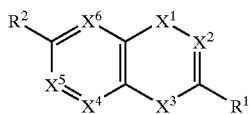

(X)

including isomers, enantiomers, diastereomers, tautomers, pharmaceutically acceptable salts, prodrugs and solvates thereof wherein:

X[1] is C=O, —S(O)—, or —S(O)$_2$—;

X[2] is CR[3] or N;

X[3] is —NH—, —O—, or —S—;

X[4] is CR[4] or N;

X[5] is CR[5] or N;

X[6] is CR[6] or N;

R[1] is alkyl, substituted alkyl, alkenyl, substituted alkenyl, alkynyl, substituted alkynyl, NR[8]R[9], SR[20], cycloalkyl, substituted cycloalkyl, aryl, substituted aryl, heterocycloalkyl, or heteroaryl;

R[2] is halogen, cyano, nitro, hydroxy, oxo (double bond is no longer present between CR[2] and X[6]), SR[7], S(O)R[7], SO$_2$R[7], SO$_2$NR[8]R[9], CO$_2$R[7], C(O)NR[8]R[9], or heteroaryl;

R[3] is hydrogen, hydroxy, halogen, cyano, CO$_2$R[7], NR[8]R[9], alkyl, substituted alkyl, alkenyl, substituted alkenyl, alkynyl, substituted alkynyl, cycloalkyl, substituted cycloalkyl, aryl, substituted aryl, heterocycloalkyl or heteroaryl;

R[4], R[5], and R[6] are independently selected from the group consisting of hydrogen, halogen, nitro, cyano, O—R[7], NR[8]R[9], SR[7], S(O)R[7], SO$_2$R[7], SO$_3$R[7], SO$_2$NR[8]R[9], CO$_2$R[7], C(O)NR[8]R[9], C(O)alkyl, C(O)substituted alkyl, alkyl, substituted alkyl, alkenyl, substituted alkenyl, alkynyl and substituted alkynyl;

R[7], R[10], and R[11], are independently selected from the group consisting of hydrogen, alkyl, substituted alkyl, alkenyl, alkynyl, cycloalkyl, substituted cycloalkyl, C(O)alkyl, C(O)substituted alkyl, C(O)cycloalkyl, C(O) substituted cycloalkyl, C(O)aryl, C(O)substituted aryl, C(O)Oalkyl, C(O)Osubstituted alkyl, C(O)heterocycloalkyl, C(O)heteroaryl, aryl, substituted aryl, heterocycloalkyl and heteroaryl;

R[8] and R[9] are independently selected from the group consisting of hydrogen, alkyl, substituted alkyl, cycloalkyl, substituted cycloalkyl, alkenyl, alkynyl, C(O)alkyl, C(O) substituted alkyl, C(O)cycloalkyl, C(O)substituted cycloalkyl, C(O)aryl, C(O)substituted aryl, C(O)Oalkyl, C(O)Osubstituted alkyl, C(O)heterocycloalkyl, C(O) heteroaryl, aryl, substituted aryl, heterocycloalkyl, and heteroaryl or R[8] and R[9] taken together with the nitrogen atom to which they are attached complete a heterocycloalkyl or heteroaryl ring;

R[20] is alkyl, substituted alkyl, cycloalkyl, aryl, substituted aryl, heteroaryl or heterocycloalkyl;

R[3] and R[1] may be taken together with the carbon atoms to which they are attached to form a monocyclic or substituted monocyclic ring system of 5 or 6 carbon atoms; and R[4] and R[5] may be joined together by the chain —O—CH$_2$—O— or —O—CH$_2$—CH$_2$—O—.

[7] In another even more preferred embodiment, the present invention provides a method for the treatment or prevention of allograft rejection comprising: administering a therapeutically effective amount of a phosphodiesterase Type 4 inhibitor and a compound of formula (X):

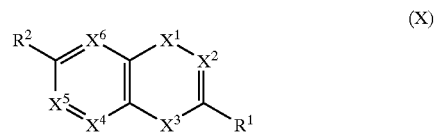

(X)

including isomers, enantiomers, diastereomers, tautomers, pharmaceutically acceptable salts, prodrugs and solvates thereof wherein:

X[1] is C=O, —S(O)—, or —S(O)$_2$—;

X[2] is CR[3] or N;

X[3] is —NH—, —O—, or —S—;

X[4] is CR[4] or N;

X[5] is CR[5] or N;

X[6] is CR[6] or N;

R[1] is alkyl, substituted alkyl, alkenyl, substituted alkenyl, alkynyl, substituted alkynyl, NR[8]R[9], SR[20], cycloalkyl, substituted cycloalkyl, aryl, substituted aryl, heterocycloalkyl, or heteroaryl;

R[2] is halogen, cyano, nitro, hydroxy, oxo (double bond is no longer present between CR[2] and X[6]), SR[7], S(O)R[7], SO$_2$R[7], SO$_2$NR[8]R[9], CO$_2$R[7], C(O)NR[8]R[9], or heteroaryl;

R[3] is hydrogen, hydroxy, halogen, cyano, CO$_2$R[7], NR[8]R[9], alkyl, substituted alkyl, alkenyl, substituted alkenyl, alkynyl, substituted alkynyl, cycloalkyl, substituted cycloalkyl, aryl, substituted aryl, heterocycloalkyl or heteroaryl;

R[4], R[5], and R[6] are independently selected from the group consisting of hydrogen, halogen, nitro, cyano, O—R[7], NR[8]R[9], SR[7], S(O)R[7], SO$_2$R[7], SO$_3$R[7], SO$_2$NR[8]R[9], CO$_2$R[7], C(O)NR[8]R[9], C(O)alkyl, C(O)substituted alkyl, alkyl, substituted alkyl, alkenyl, substituted alkenyl, alkynyl and substituted alkynyl;

R[7], R[10], and R[11], are independently selected from the group consisting of hydrogen, alkyl, substituted alkyl, alkenyl, alkynyl, cycloalkyl, substituted cycloalkyl, C(O) alkyl, C(O)substituted alkyl, C(O)cycloalkyl, C(O) substituted cycloalkyl, C(O)aryl, C(O)substituted aryl, C(O) Oalkyl, C(O)Osubstituted alkyl, C(O)heterocycloalkyl, C(O)heteroaryl, aryl, substituted aryl, heterocycloalkyl and heteroaryl;

R[8] and R[9] are independently selected from the group consisting of hydrogen, alkyl, substituted alkyl, cycloalkyl, substituted cycloalkyl, alkenyl, alkynyl, C(O)alkyl, C(O) substituted alkyl, C(O)cycloalkyl, C(O)substituted cycloalkyl, C(O)aryl, C(O)substituted aryl, C(O)Oalkyl, C(O)Osubstituted alkyl, C(O)heterocycloalkyl, C(O) heteroaryl, aryl, substituted aryl, heterocycloalkyl, and heteroaryl or R[8] and R[9] taken together with the nitrogen atom to which they are attached complete a heterocycloalkyl or heteroaryl ring;

$R^{20}$ is alkyl, substituted alkyl, cycloalkyl, aryl, substituted aryl, heteroaryl or heterocycloalkyl;

$R^3$ and $R^1$ may be taken together with the carbon atoms to which they are attached to form a monocyclic or substituted monocyclic ring system of 5 or 6 carbon atoms; and $R^4$ and $R^5$ may be joined together by the chain —O—CH$_2$—O— or —O—CH$_2$—CH$_2$—O—.

[8] In another even more preferred embodiment, the phosphodiesterase Type 4 inhibitor is Rolipram.

[9] In another even more preferred embodiment, the phosphodiesterase Type 4 inhibitor is [4-[3-(cyclopentyloxy)-4-methoxy-phenyl]-2-pyrrolidinone].

[10] In a second embodiment, the present invention provides a novel compound, comprising: a compound of formula (I)

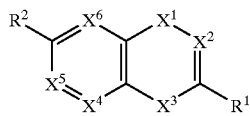
(I)

including isomers, enantiomers, diastereomers, tautomers, pharmaceutically acceptable salts, prodrugs and solvates thereof wherein:
$X^1$ is C=O, —S(O)—, or —S(O)$_2$—;
$X^2$ is CR$^3$ or N;
$X^3$ is —NH—, —O—, or —S—;
$X^4$ is CR$^4$ or N;
$X^5$ is CR$^5$ or N;
$X^6$ is CR$^6$ or N;
$R^1$ is alkyl, substituted alkyl, alkenyl, substituted alkenyl, alkynyl, substituted alkynyl, cycloalkyl, substituted cycloalkyl, aryl, substituted aryl, heterocycloalkyl, or heteroaryl;
$R^2$ is cyano, hydroxy, oxo (double bond is no longer present between CR$^2$ and X$^6$), SR$^7$, S(O)R$^7$, SO$_2$R$^7$, SO$_2$NR$^8$R$^9$, CO$_2$R$^7$, C(O)NR$^8$R$^9$, or heteroaryl;
$R^3$ is hydrogen, hydroxy, halogen, cyano, CO$_2$R$^7$, NR$^8$R$^9$, alkyl, substituted alkyl, alkenyl, substituted alkenyl, alkynyl, substituted alkynyl, cycloalkyl, substituted cycloalkyl, aryl, substituted aryl, heterocycloalkyl or heteroaryl;
$R^4$, $R^5$, and $R^6$ are independently selected from the group consisting of hydrogen, halogen, nitro, cyano, O—R$^7$, NR$^8$R$^9$, SR$^7$, S(O)R$^7$, SO$_2$R$^7$, SO$_3$R$^7$, SO$_2$NR$^8$R$^9$, C$_2$R$^7$, C(O)NR$^8$R$^9$, C(O)alkyl, C(O)substituted alkyl, alkyl, substituted alkyl, alkenyl, substituted alkenyl, alkynyl and substituted alkynyl;
$R^7$, $R^{10}$, and $R^{11}$, are independently selected from the group consisting of hydrogen, alkyl, substituted alkyl, alkenyl, alkynyl, cycloalkyl, substituted cycloalkyl, C(O)alkyl, C(O)substituted alkyl, C(O)cycloalkyl, C(O) substituted cycloalkyl, C(O)aryl, C(O)substituted aryl, C(O) Oalkyl, C(O)Osubstituted alkyl, C(O)heterocycloalkyl, C(O)heteroaryl, aryl, substituted aryl, heterocycloalkyl and heteroaryl;
$R^8$ and $R^9$ are independently selected from the group consisting of hydrogen, alkyl, substituted alkyl, cycloalkyl, substituted cycloalkyl, alkenyl, alkynyl, C(O)alkyl, C(O) substituted alkyl, C(O)cycloalkyl, C(O)substituted cycloalkyl, C(O)aryl, C(O)substituted aryl, C(O)Oalkyl, C(O)Osubstituted alkyl, C(O)heterocycloalkyl, C(O) heteroaryl, aryl, substituted aryl, heterocycloalkyl, and heteroaryl or $R^8$ and $R^9$ taken together with the nitrogen atom to which they are attached complete a heterocycloalkyl or heteroaryl ring;

$R^3$ and $R^1$ may be taken together with the carbon atoms to which they are attached to form a monocyclic or substituted monocyclic ring system of 5 or 6 carbon atoms; and $R^4$ and $R^5$ may be joined together by the chain —O—CH$_2$—O— or —O—CH$_2$—CH$_2$—O—;
with the following provisos:
(a) when $X^1$ is C=O, $X^2$ is CR$^3$, $X^3$ is NH, $X^4$ is CR$^4$, $X^5$ is CR$^5$, $X^6$ is CR$^6$, $R^1$ is substituted or meta unsubstituted phenyl, $R^3$ is H, $R^4$ is H, $R^5$ is H and $R^6$ is H, then $R^2$ is not PhCONH,

(b) when $X^1$ is C=O, $X^2$ is CR$^3$, $X^3$ is NH, $X^4$ is CR$^4$, $X^5$ is CR$^5$, $X^6$ is CR$^6$, $R^1$ is phenyl substituted with H, F, Cl, Br, I, CH$_3$, CF$_3$, OH, OCH$_3$, OCF$_3$, OCH$_2$CH$_3$, NH$_2$, NHCH$_3$, N(CH$_3$)$_2$, O-benzyl, —C(=O)—R$_0$, or —C(=O)—OR$_0$ and R$_0$ is a lower alkyl group, $R^3$ is H, $R^4$ is H, $R^5$ is H and $R^6$ is H, then $R^2$ is not

where Y is CH$_2$, O or S, m and n are each greater than 1, and the sum of m and n is between 3 and 6; and
(c) when $R^2$ is heteroaryl, at least one of the heteroatoms must be O;

[11] In a preferred embodiment, the present invention provides a compound of formula (II)

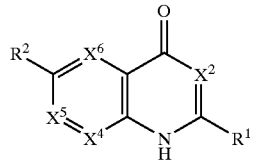
(II)

including isomers, enantiomers, diastereomers, tautomers, pharmaceutically acceptable salts, prodrugs and solvates thereof wherein:
$R^2$ is a monocyclic substituted or unsubstituted heteroaryl group.

[12] In a more preferred embodiment, the present invention provides a compound of formula (III)

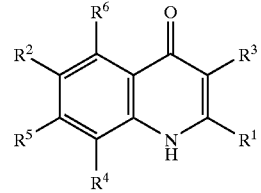
(III)

including isomers, enantiomers, diastereomers, tautomers, pharmaceutically acceptable salts, prodrugs and solvates thereof wherein:
$R^2$ is 4-oxazolyl, substituted 4-oxazolyl, 5-oxazolyl, or substituted 5-oxazolyl;
$R^3$ is hydrogen, hydroxy, NR$^8$R$^9$, alkyl of 1 to 4 carbons, alkenyl of 2 to 4 carbons, alkynyl of 2 to 4 carbons, substituted alkyl of 1 to 4 carbons, phenyl, substituted phenyl, cycloalkyl of 5 to 7 carbons, substituted cycloalkyl of 5 to 7 carbons, monocyclic heterocycloalkyl and monocyclic heteroaryl;

$R^4$ is hydrogen, halogen, nitro, hydroxy, alkyl of 1 to 4 carbons, cyano, $CF_3$, $OCF_3$, $OCH_3$, $SCH_3$, $S(O)CH_3$, or $S(O)_2CH_3$;

$R^5$ is hydrogen, halogen, nitro, hydroxy, alkyl of 1 to 4 carbons, cyano, vinyl, $CF_3$, $CF_2CF_3$, $CH=CF_2$, $OCH_3$, $OCF_3$, $OCHF_2$, $SCH_3$, $S(O)CH_3$, or $S(O)_2CH_3$; and $R^6$ is hydrogen, halogen, nitro, hydroxy, alkyl of 1 to 4 carbons, cyano, $CF_3$, $OCH_3$, $OCF_3$, $SCH_3$, $S(O)CH_3$, and $S(O)_2CH_3$.

[13] In an even more preferred embodiment, the present invention provides a compound including isomers, enantiomers, diastereomers, tautomers, pharmaceutically acceptable salts, prodrugs and solvates
wherein:

$R^2$ is 4-oxazolyl, substituted 4-oxazolyl, 5-oxazolyl, substituted 5-oxazolyl or heteroaryl;

$R^3$ is hydrogen, hydroxy, halogen, methyl or $NR^8R^9$;

$R^4$ is hydrogen;

$R^5$ is halogen, methyl, ethyl, substituted alkenyl, alkyne, OMe or $OCF_3$; and $R^6$ is hydrogen.

[14] In another even more preferred embodiment, the present invention provides a compound including isomers, enantiomers, diastereomers, tautomers, pharmaceutically acceptable salts, prodrugs and solvates wherein:

$R^2$ is 4-oxazolyl, substituted 4-oxazolyl, 5-oxazolyl or substituted 5-oxazolyl;

$R^3$ is hydrogen, hydroxy, halogen or methyl;

$R^4$ is hydrogen;

$R^5$ is halogen, methyl or OMe; and $R^6$ is hydrogen.

[15] In another even more preferred embodiment, the present invention provides a compound of formula (V)

(V)

including isomers, enantiomers, diastereomers, tautomers, pharmaceutically acceptable salts, prodrugs and solvates selected from:

a compound of formula (V) wherein:
$R^1$ is and $R^3$ is hydrogen;

a compound of formula (V) wherein:

and $R^3$ is hydrogen;
a compound of formula (V) wherein:

and $R^3$ is hydrogen;
a compound of formula (V) wherein:
$R^1$ is $CH_3$ and $R^3$ is hydrogen;
a compound of formula (V) wherein:

and $R^3$ is $CH_3$;
a compound of formula (V) wherein:
$R^1$ is and $R^3$ is hydrogen;
a compound of formula (V) wherein:
$R^1$ is and $R^3$ is hydrogen;
a compound of formula (V) wherein:
$R^1$ is and $R^3$ is hydrogen;

a compound of formula (V) wherein:

R$^1$ is

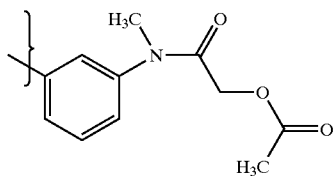

and R$^3$ is hydrogen;

a compound of formula (V) wherein:

R$^1$ is

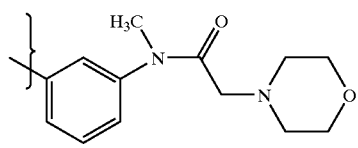

and R$^3$ is hydrogen;

a compound of formula (V) wherein:

R$^1$ is

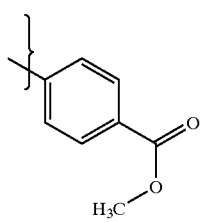

and R$^3$ is hydrogen; ps a compound of formula (V) wherein:

R$^1$ is

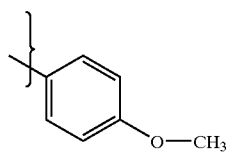

and R$^3$ is hydrogen;

a compound of formula (V) wherein:

R$^1$ is

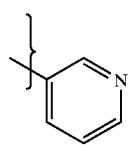

and R$^3$ is hydrogen;

a compound of formula (V) wherein:

R$^1$ is

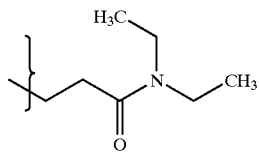

and R$^3$ is hydrogen;

a compound of formula (V) wherein:

R$^1$ is

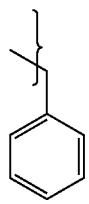

and R$^3$ is hydrogen;

a compound of formula (V) wherein:

R$^1$ is

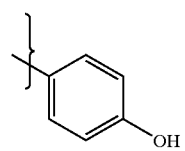

and R$^3$ is hydrogen;

a compound of formula (V) wherein:

R$^1$ is

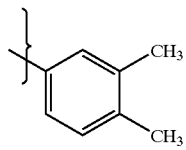

and R$^3$ is hydrogen;

a compound of formula (V) wherein:

R$^1$ is

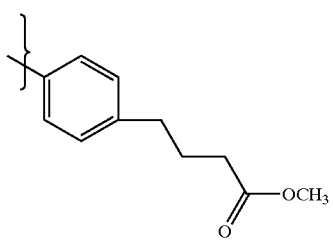

and R$^3$ is hydrogen;

a compound of formula (V) wherein:

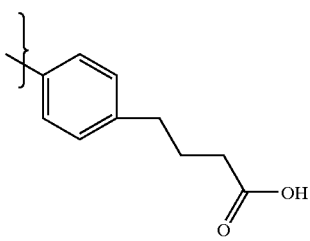

and R³ is hydrogen;

a compound of formula (V) wherein:
R¹ is

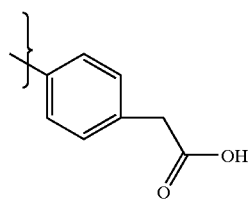

and R³ is hydrogen;

a compound of formula (V) wherein:
R¹ is

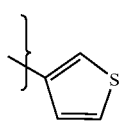

and R³ is hydrogen;

a compound of formula (V) wherein:
R¹ is

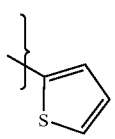

and R³ is hydrogen;

a compound of formula (V) wherein:
R¹ is

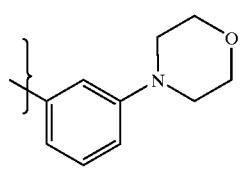

and R³ is hydrogen;

a compound of formula (V) wherein:
R¹ is

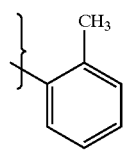

and R³ is hydrogen;

a compound of formula (V) wherein:
R¹ is

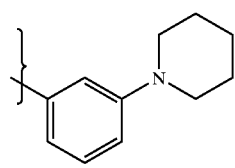

and R³ is hydrogen;

a compound of formula (V) wherein:
R¹ is

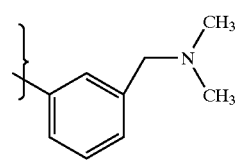

and R³ is hydrogen;

a compound of formula (V) wherein:
R¹ is

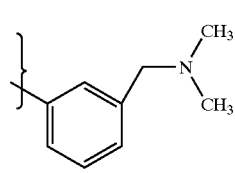

and R³ is Br;

a compound of formula (V) wherein:
R¹ is

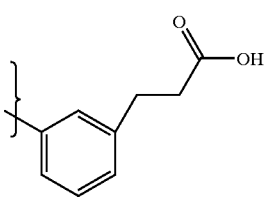

and R³ is hydrogen;

a compound of formula (V) wherein:
R¹ is

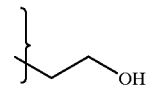

and R³ is hydrogen;

a compound of formula (V) wherein:

R$^1$ is

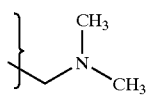

and R$^3$ is hydrogen;

a compound of formula (V) wherein:

R$^1$ is

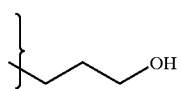

and R$^3$ is hydrogen;

a compound of formula (V) wherein:

R$^1$ is

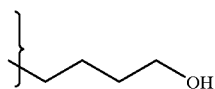

and R$^3$ is hydrogen;

a compound of formula (V) wherein:

R$^1$ is

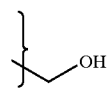

and R$^3$ is hydrogen;

a compound of formula (V) wherein:

R$^1$ is

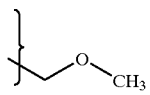

and R$^3$ is hydrogen;

a compound of formula (V) wherein:

R$^1$ is

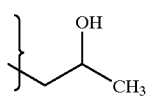

and R$^3$ is hydrogen;

a compound of formula (V) wherein:

R$^1$ is

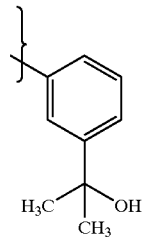

and R$^3$ is hydrogen;

a compound of formula (V) wherein:

R$^1$ is

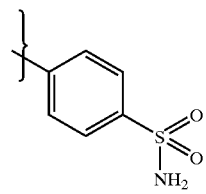

and R$^3$ is hydrogen;

a compound of formula (V) wherein:

R$^1$ is

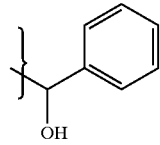

and R$^3$ is hydrogen;

a compound of formula (V) wherein:

R$^1$ is

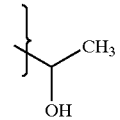

and R$^3$ is hydrogen;

a compound of formula (V) wherein:

R$^1$ is

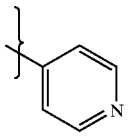

and R$^3$ is hydrogen;

a compound of formula (V) wherein:

R¹ is

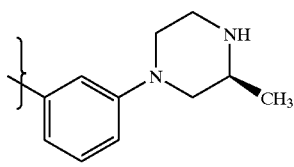

and R³ is hydrogen;

a compound of formula (V) wherein:

R¹ is

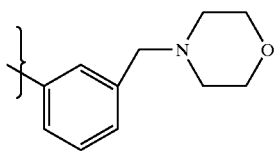

and R³ is hydrogen;

a compound of formula (V) wherein:

R¹ is

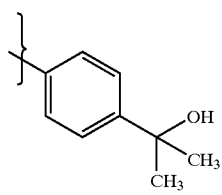

and R³ is hydrogen;

a compound of formula (V) wherein:

R¹ is

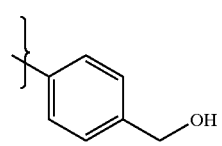

and R³ is hydrogen;

a compound of formula (V) wherein:

R¹ is

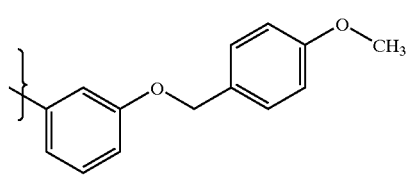

and R³ is hydrogen;

a compound of formula (V) wherein:

R¹ is

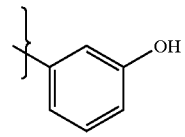

and R³ is hydrogen;

a compound of formula (V) wherein:

R¹ is

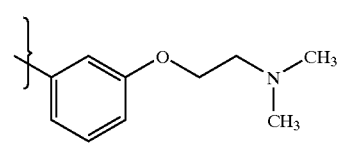

and R³ is hydrogen;

a compound of formula (V) wherein:

R¹ is

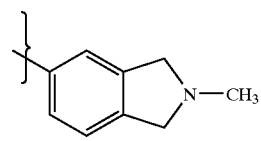

and R³ is hydrogen;

a compound of formula (V) wherein:

R¹ is

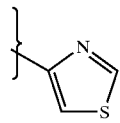

and R³ is hydrogen;

a compound of formula (V) wherein:

R¹ is

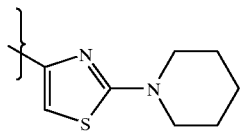

and R³ is hydrogen;

a compound of formula (V) wherein:

R¹ is

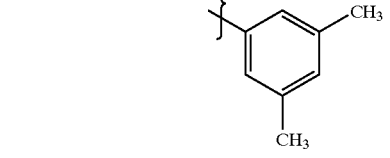

and R³ is hydrogen;

a compound of formula (V) wherein:

R¹ is

[structure: 3-(methylthio)phenyl]

and R³ is hydrogen;

a compound of formula (V) wherein:

R¹ is

[structure: 3-(methylsulfonyl)phenyl]

and R³ is hydrogen;

a compound of formula (V) wherein:

R¹ is

[structure: 3-[4-(2-methoxyethyl)piperazin-1-yl]phenyl]

and R³ is hydrogen;

a compound of formula (V) wherein:

R¹ is

[structure: 3-(2,6-dimethylmorpholin-4-yl)phenyl]

and R³ is hydrogen;

a compound of formula (V) wherein:

R¹ is

[structure: 3-bromo-4-methylphenyl]

and R³ is hydrogen;

a compound of formula (V) wherein:

R¹ is

[structure: 3-[(tetrahydrofuran-2-ylmethyl)amino]phenyl]

and R³ is hydrogen;

a compound of formula (V) wherein:

R¹ is

[structure: 3-[3-(dimethylamino)pyrrolidin-1-yl]phenyl]

and R³ is hydrogen;

a compound of formula (V) wherein:

R¹ is

[structure: 2-methyl-5-(morpholin-4-yl)phenyl]

and R³ is hydrogen;

a compound of formula (V) wherein:

R¹ is

[structure: 2-methyl-5-(4-methylpiperazin-1-yl)phenyl]

and R³ is hydrogen;

a compound of formula (V) wherein:

R¹ is

[structure: 3-[4-(tert-butoxycarbonyl)piperazin-1-yl]phenyl]

and R³ is hydrogen;

a compound of formula (V) wherein:
  R¹ is

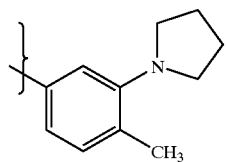

and R³ is hydrogen;
a compound of formula (V) wherein:
  R¹ is

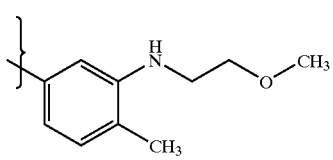

and R³ is hydrogen;
a compound of formula (V) wherein:
  R¹ is

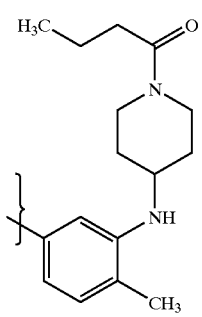

and R³ is hydrogen;
a compound of formula (V) wherein:
  R¹ is

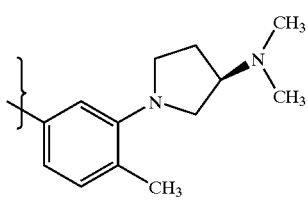

and R³ is hydrogen;
a compound of formula (V) wherein:
  R¹ is

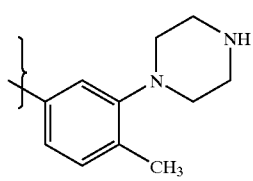

and R³ is hydrogen;

a compound of formula (V) wherein:
  R¹ is

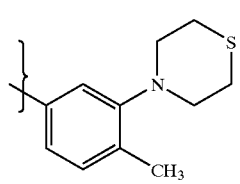

and R³ is hydrogen;
a compound of formula (V) wherein:
  R¹ is

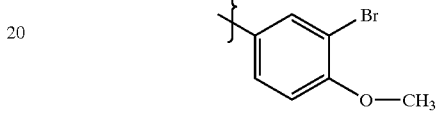

and R³ is hydrogen;
a compound of formula (V) wherein:
  R¹ is

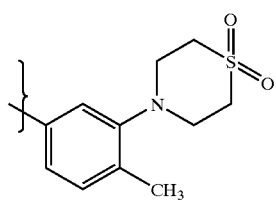

and R³ is hydrogen;
a compound of formula (V) wherein:
  R¹ is

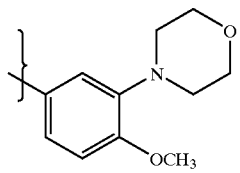

and R³ is hydrogen;
a compound of formula (V) wherein:
  R¹ is

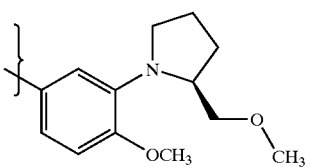

and R³ is hydrogen;

a compound of formula (V) wherein:
R¹ is

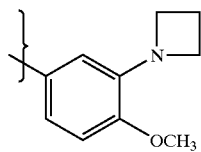

and R³ is hydrogen;
a compound of formula (V) wherein:
R¹ is

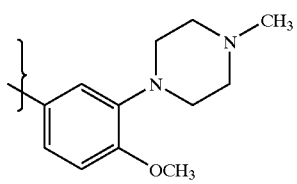

and R³ is hydrogen;
a compound of formula (V) wherein:
R¹ is

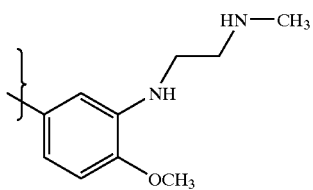

and R³ is hydrogen;
a compound of formula (V) wherein:
R¹ is

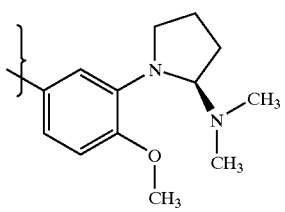

and R³ is hydrogen;
a compound of formula (V) wherein:
R¹ is

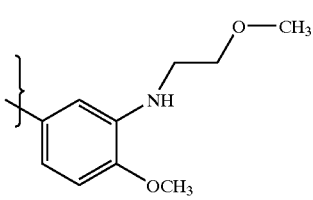

and R³ is hydrogen;

a compound of formula (V) wherein:
R¹ is

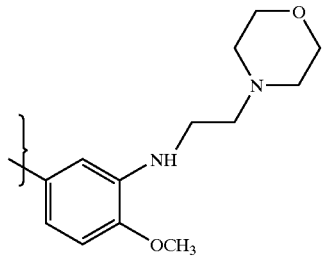

and R³ is hydrogen;
a compound of formula (V) wherein:
R¹ is

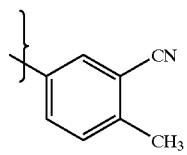

and R³ is hydrogen;
a compound of formula (V) wherein:
R¹ is

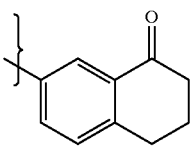

and R³ is hydrogen;
a compound of formula (V) wherein:
R¹ is

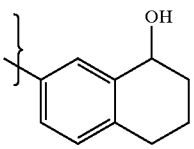

and R³ is hydrogen;
a compound of formula (V) wherein:
R¹ is

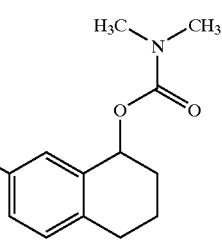

and R³ is hydrogen;

a compound of formula (V) wherein:
R¹ is

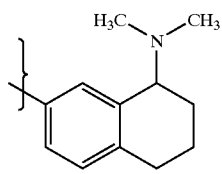

and R³ is hydrogen;
a compound of formula (V) wherein:
R¹ is

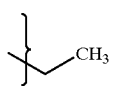

and R³ is hydrogen;
a compound of formula (V) wherein:
R¹ is

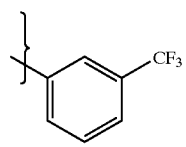

and R³ is hydrogen;
a compound of formula (V) wherein:
R¹ is

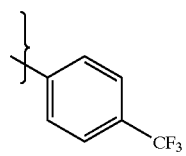

and R³ is hydrogen;
a compound of formula (V) wherein:
R¹ is

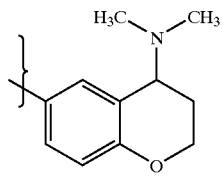

and R³ is hydrogen;
a compound of formula (V) wherein:
R¹ is

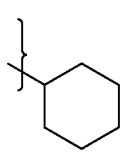

and R³ is hydrogen;

a compound of formula (V) wherein:
R¹ is

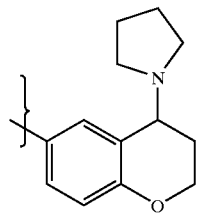

and R³ is hydrogen;
a compound of formula (V) wherein:
R¹ is

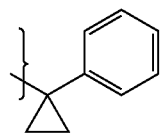

and R³ is hydrogen;
a compound of formula (V) wherein:
R¹ is

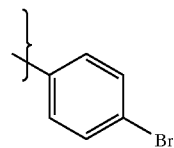

and R³ is hydrogen;
a compound of formula (V) wherein:
R¹ is

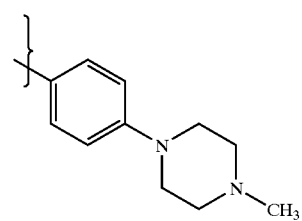

and R³ is hydrogen;
and a compound of formula (V) wherein:
R¹ is

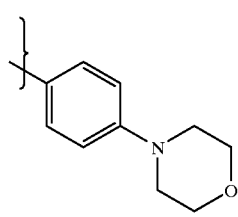

and R³ is hydrogen.

[16] In another even more preferred embodiment, the present invention provides a compound including isomers, enantiomers, diastereomers, tautomers, pharmaceutically acceptable salts, prodrugs and solvates thereof selected from:
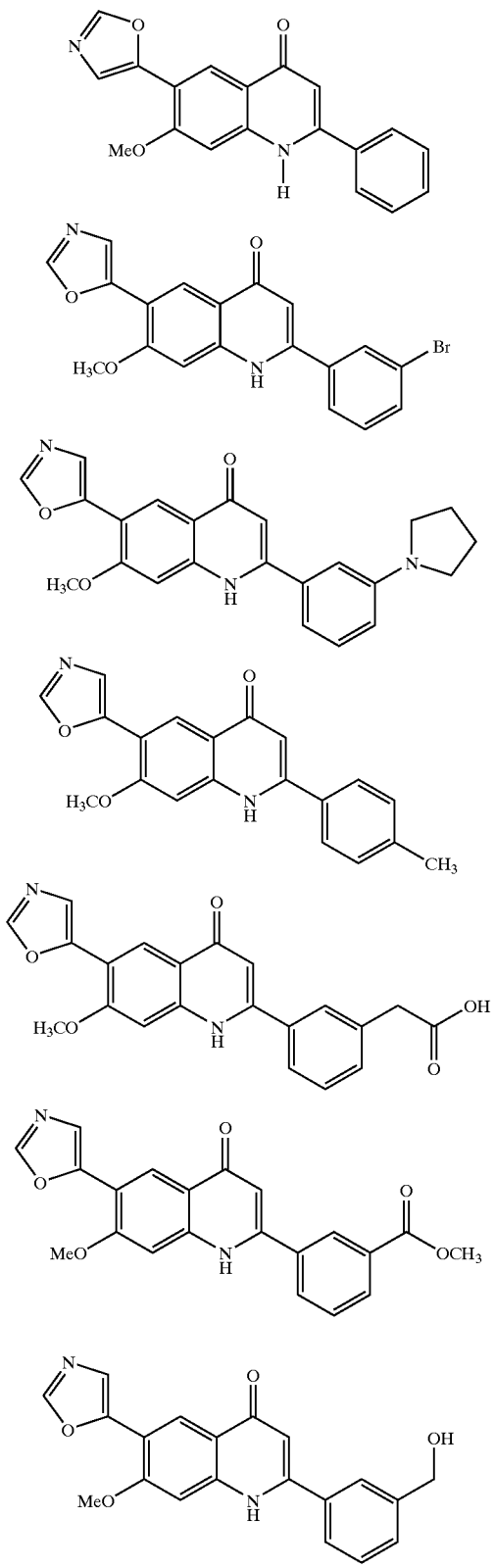
-continued
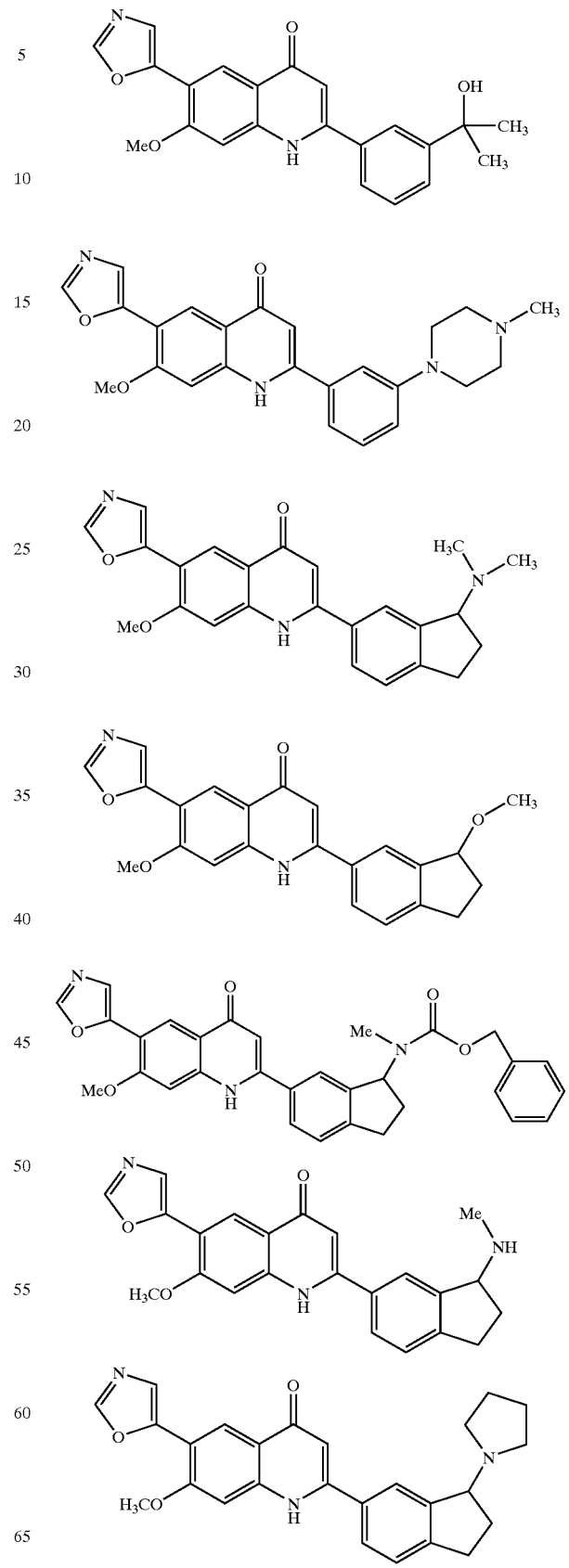

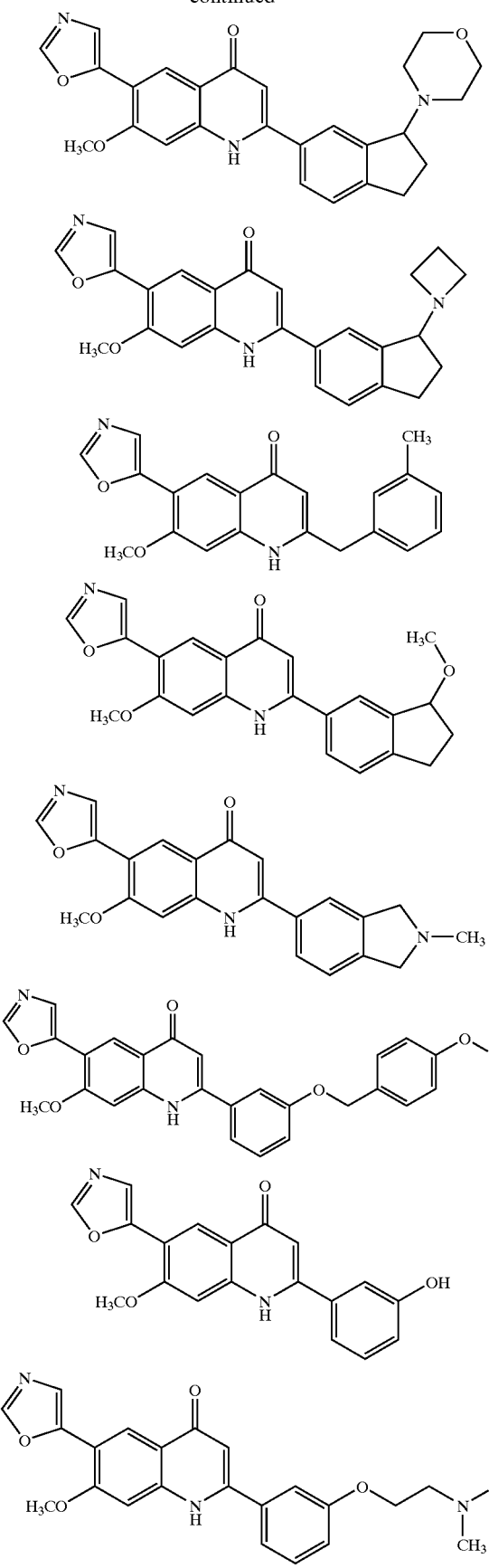
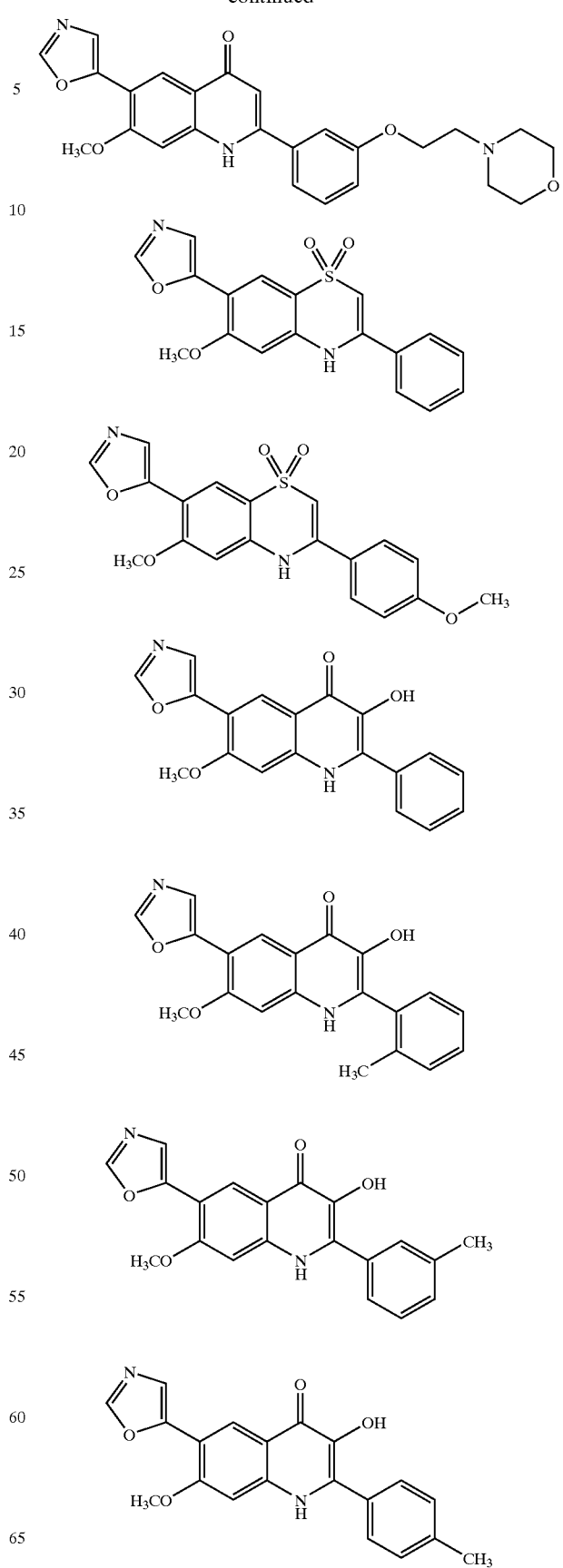

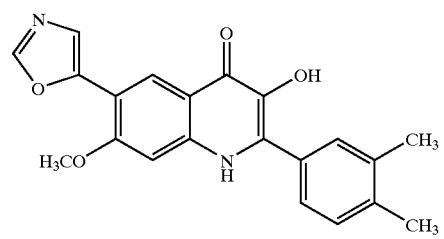
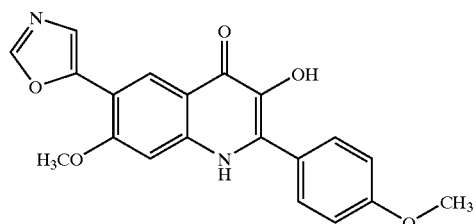
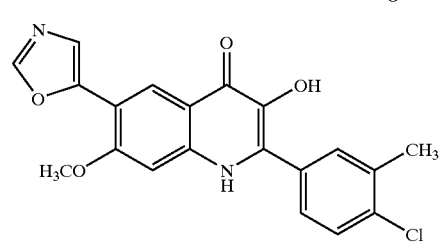
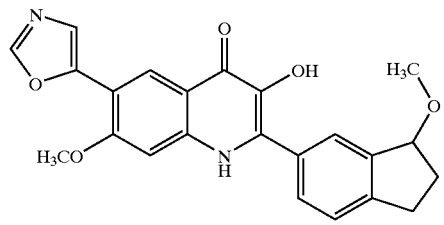
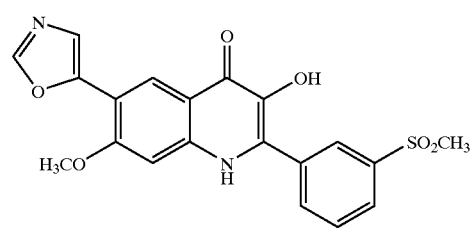
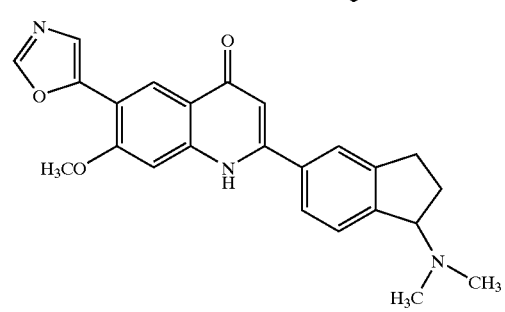
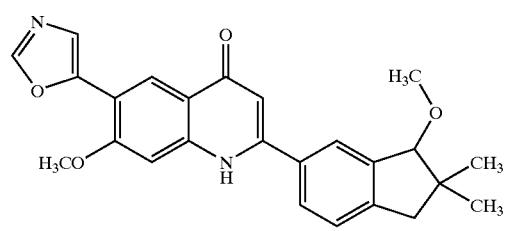
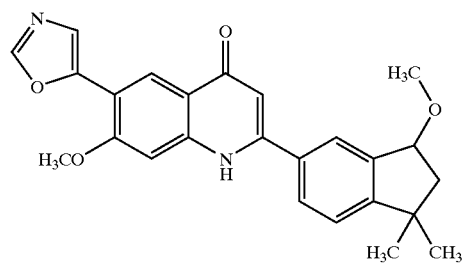
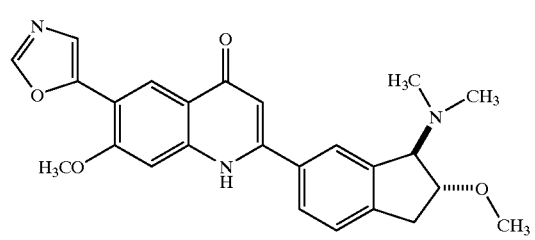
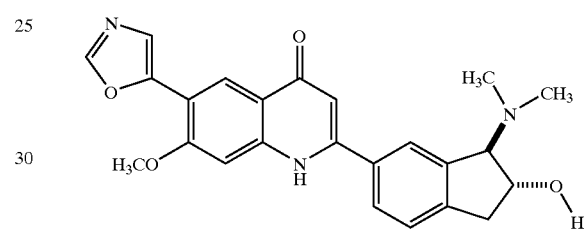
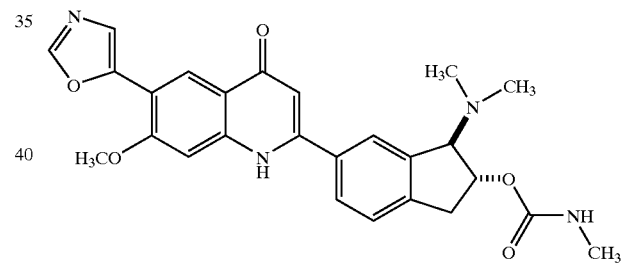
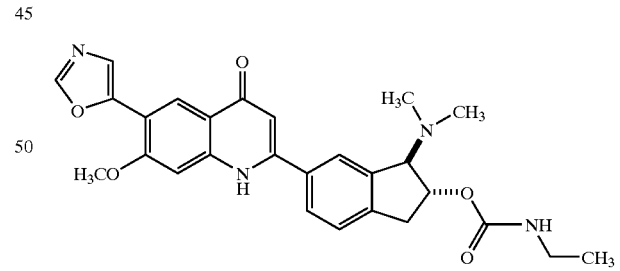
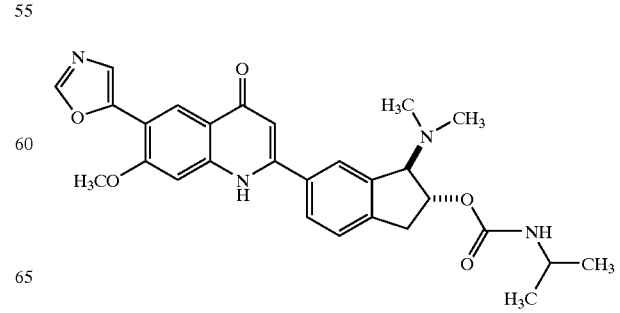

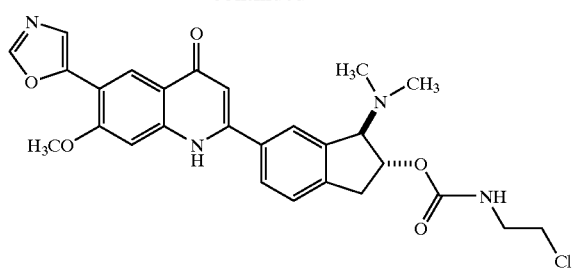
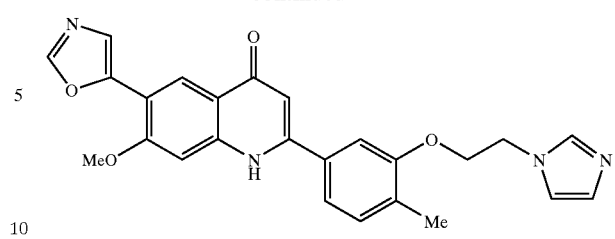
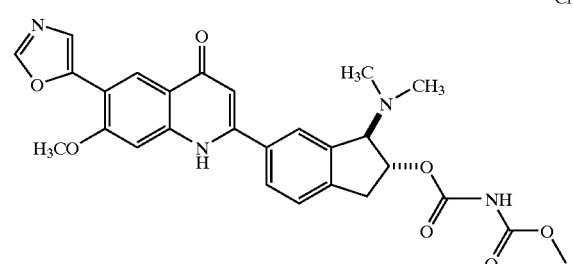
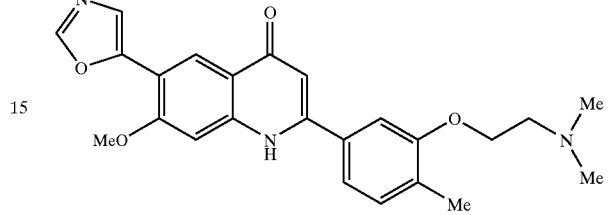
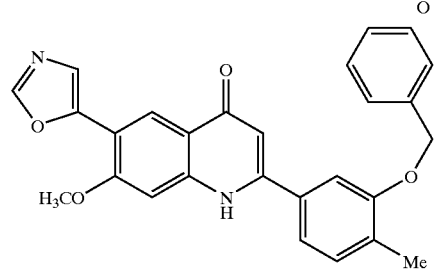
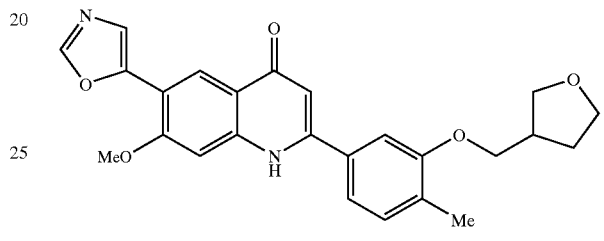
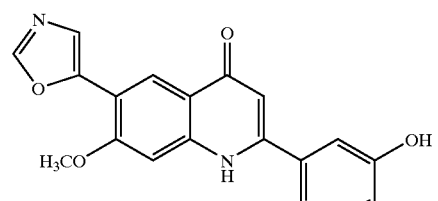
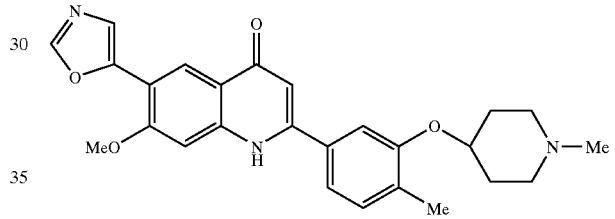
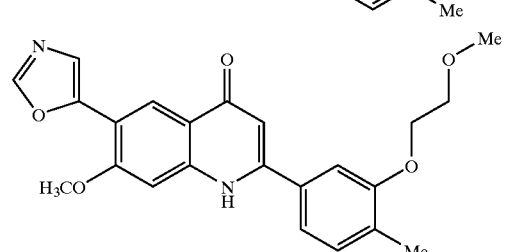
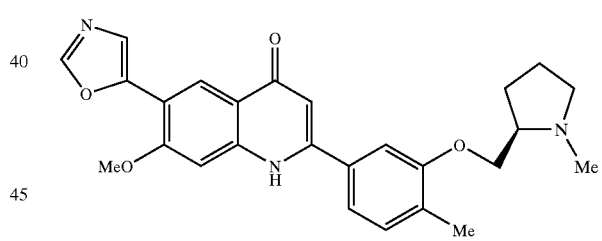
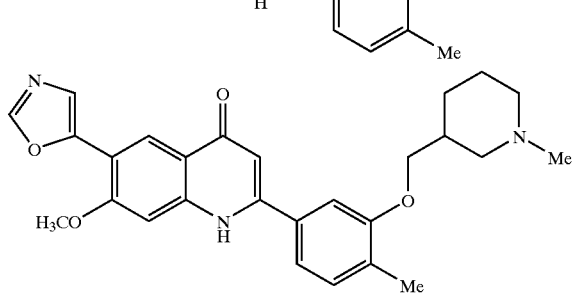
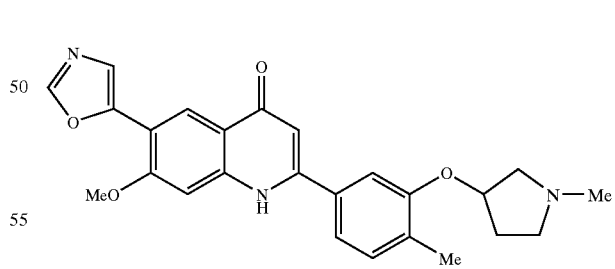
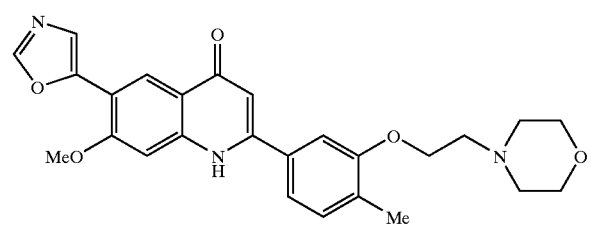
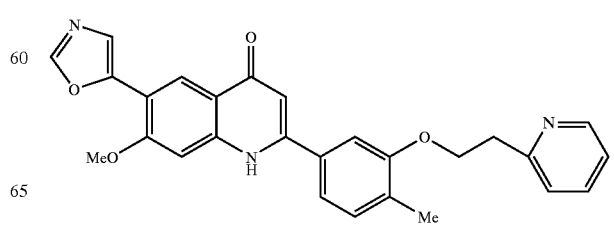

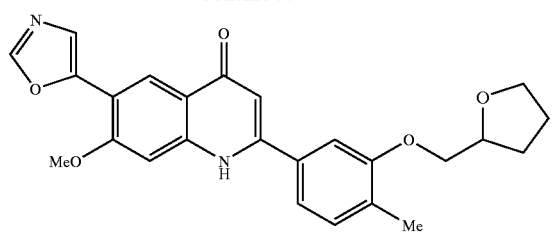
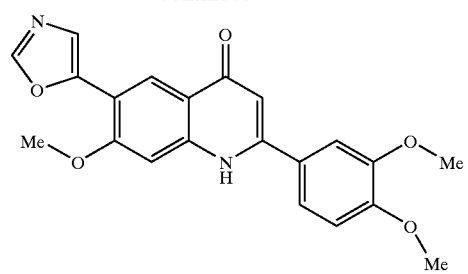
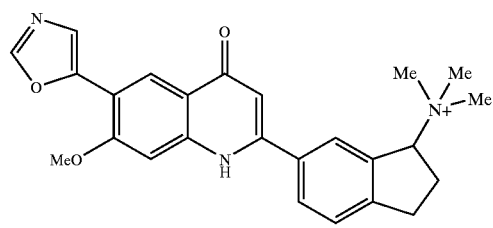
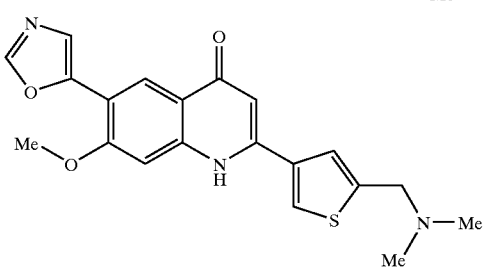
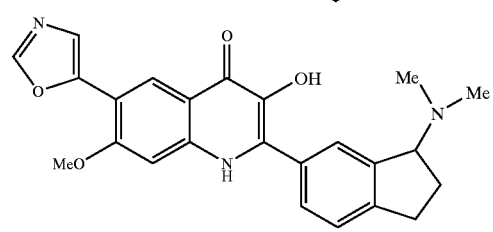
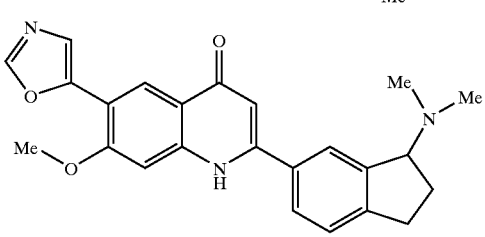
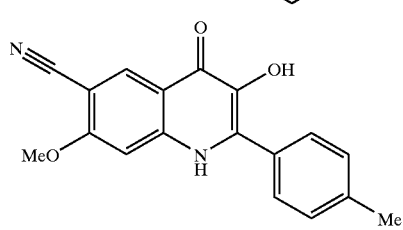
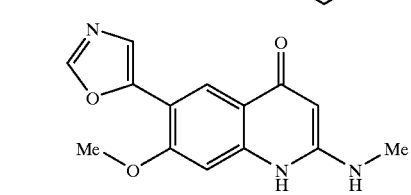
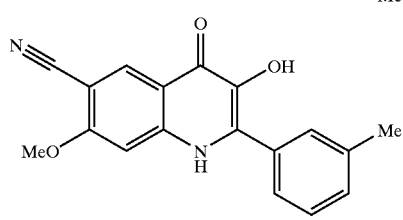
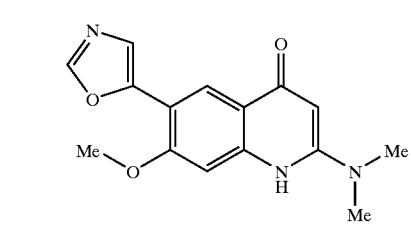
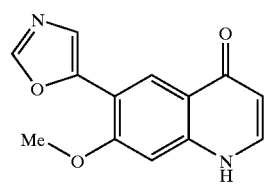
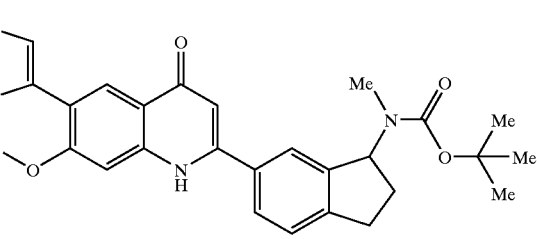
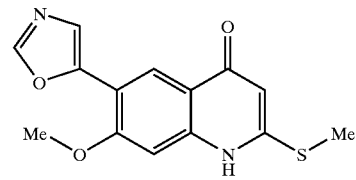
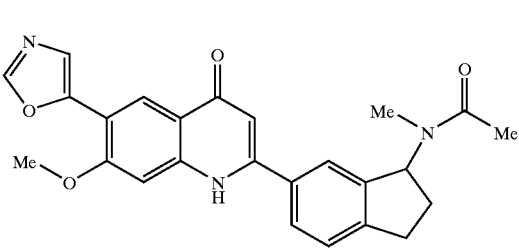
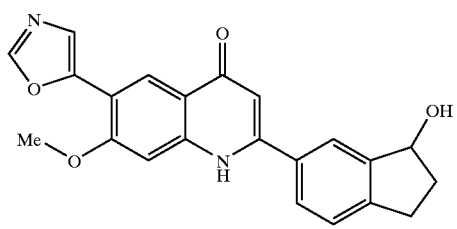

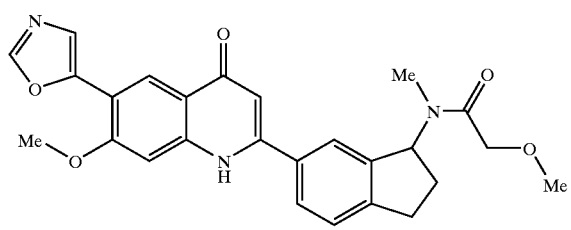
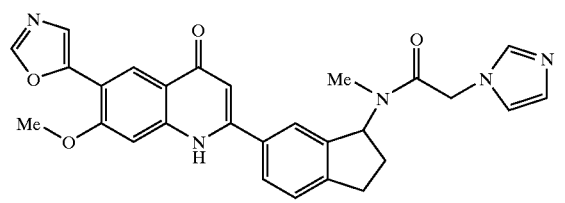
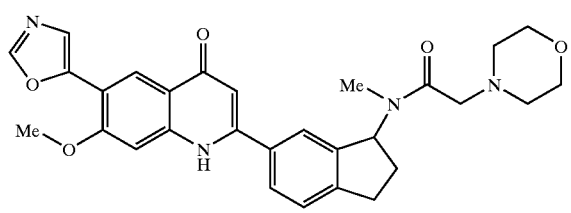
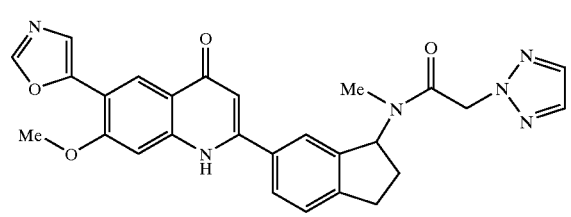
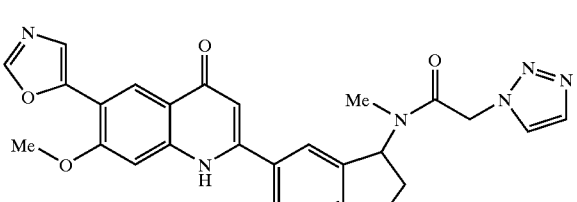

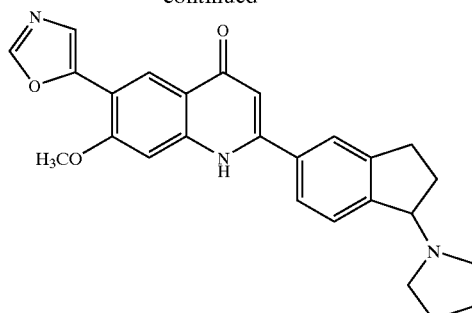
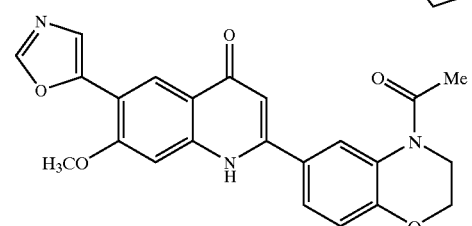
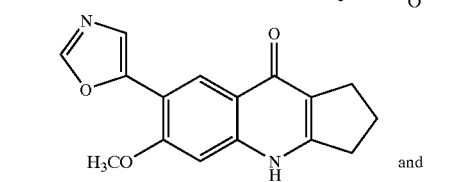

and

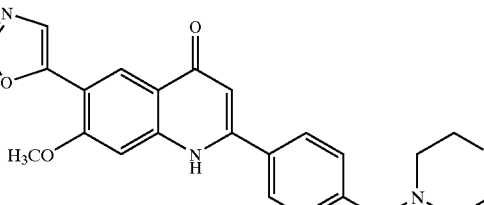

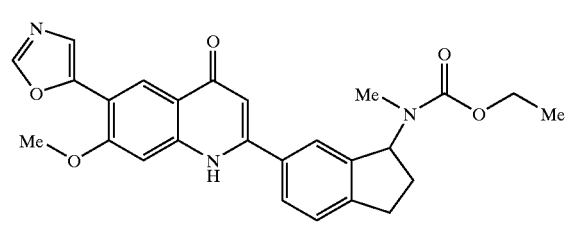
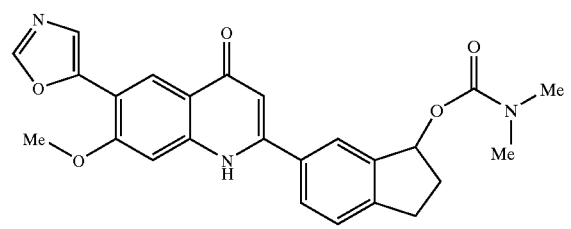

[17] In a third preferred embodiment, the present invention provides a pharmaceutical composition comprising: a compound of the invention and a pharmaceutically acceptable carrier.

[18] In another preferred embodiment, the present invention provides a method of treating inosine monophosphate dehydrogenase associated disorders comprising: administering an effective amount of the pharmaceutical composition of the invention.

[19] In another preferred embodiment, the present invention provides a method of treating inosine monophosphate dehydrogenase associated disorders comprising: administering an effective amount of the pharmaceutical composition of the invention and another agent known to be useful in treatment of such disorders.

[20] In another preferred embodiment, the present invention provides a method of treating inosine monophosphate dehydrogenase associated disorders comprising: administering a therapeutically effective amount of the pharmaceutical composition of the invention and a phosphodiesterase Type 4 inhibitor.

[21] In a another preferred embodiment, the present invention provides a method for the treatment or prevention of allograft rejection comprising: administering a therapeutically effective amount of the pharmaceutical composition of the invention and a phosphodiesterase Type 4 inhibitor.

The following are definitions of the terms as used throughout this specification and claims. The initial definition provided for a group or term herein applies to that group or term throughout the present specification, individually or as part of another group, unless otherwise indicated.

The term "alkyl" refers to straight or branched chain hydrocarbon groups having 1 to 12 carbons atoms, preferably 1 to 8 carbon atoms, and most preferably 1 to 4 carbon atoms.

The term "substituted alkyl" refers to an alkyl group as defined above having one, two, or three substituents selected from the group consisting of halo, cyano, O—$R^7$, S—$R^7$, $NR^8R^9$, nitro, cycloalkyl, substituted cycloalkyl, oxo, aryl, substituted aryl, heterocycloalkyl, heteroaryl, $CO_2R^7$, S(O)$R^7$, $SO_2R^7$, $SO_3R^7$, $SO_2NR^8R^9$, C(O)$NR^8R^9$, C(O)alkyl, and C(O)H.

The term "alkenyl" refers to straight or branched chain hydrocarbon groups having 2 to 12 carbon atoms and one, two or three double bonds, preferably 2 to 6 carbon atoms and one double bond.

The term "substituted alkenyl" refers to an alkenyl group as defined above having one, two, or three substituents selected from the group consisting of halo, cyano, O—$R^7$, S—$R^7$, $NR^8R^9$ nitro, cycloalkyl, substituted cycloalkyl, oxo, aryl, substituted aryl, heterocycloalkyl, heteroaryl, $CO_2R^7$, S(O)$R^7$, $SO_2R^7$, $SO_3R^7$, $SO_2NR^8R^9$, C(O)alkyl, and C(O)H.

The term "alkynyl" refers to straight or branched chain hydrocarbon group having 2 to 12 carbon atoms and one, two or three triple bonds, preferably 2 to 6 carbon atoms and one triple bond.

The term "substituted alkynyl" refers to an alkynyl group as defined above having one, two, or three substituents selected from the group consisting of halo, cyano, O—$R^7$, S—$R^7$, $NR^8R^9$, nitro, cycloalkyl, substituted cycloalkyl, oxo, aryl, substituted aryl, heterocycloalkyl, heteroaryl, $CO_2R^7$, S(O)$R^7$, $SO_2R^7$, $SO_3R^7$, $SO_2NR^8R^9$, C(O)$NR^8R^9$, C(O)alkyl, and C(O)H.

The term "halo" refers to chloro, bromo, fluoro, and iodo.

The term "cycloalkyl" refers to fully saturated and partially unsaturated monocyclic hydrocarbon rings of 3 to 9, preferably 3 to 7 carbon atoms. Also included in this definition are bicyclic rings where the cycloalkyl ring as defined above has a fused aryl, substituted aryl, cycloalkyl, substituted cycloalkyl, heterocycloalkyl, or heteroaryl ring provided that the point of attachment is in the cycloalkyl ring, i.e.

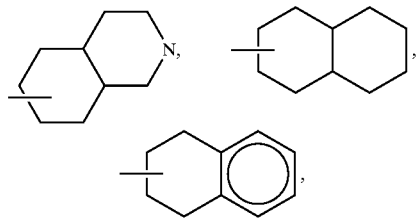

etc., as well as a cycloalkyl ring as defined above having a two or three carbon bridge or a spirocycloalkyl in which a carbon atom of the cycloallkyl ring has a carbon atom in common with a second cycloalkyl, substituted cycloalkyl, or heterocycloalkyl ring again provided that the point of attachment is in the

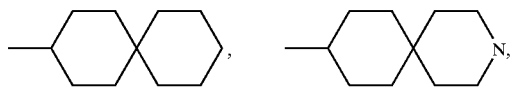

etc,

The term "substituted cycloalkyl" refers to such cycloalkyl group as defined above having one, two or three substituents selected from the group consisting of halogen, nitro, alkyl, substituted alkyl, alkenyl, cyano, cycloalkyl, substituted cycloalkyl, aryl, substituted aryl, heterocycloalkyl, heteroaryl, oxo, $OR^7$, $CO_2R^7$, C(O)$NR^8R^9$, OC(O)$R^7$, OC(O)O$R^7$, OC(O)$NR^8R^9$, $OCH_2CO_2R^7$, C(O)$R^7$, $NR^8R^9$, $NR^{10}C(O)R^7$, $NR^{10}C(O)OR^7$, $NR^{10}C(O)C(O)OR^7$, $NR^{10}C(O)C(O)NR^8R^9$, $NR^{10}C(O)C(O)$alkyl, $NR^{10}C(NCN)OR^7$, $NR^{10}C(O)NR^8R^9$, $NR^{10}C(NCN)NR^8R^9$, $NR^{10}C(NR^{11})NR^8R^9$, $NR^{10}SO_2NR^8R^9$, $NR^{10}SO_2R^7$, $SR^7$, S(O)$R^7$, $SO_2R^7$, $SO_3R^7$, $SO_2NR^8R^9$, $NHOR^7$, $NR^{10}NR^8R^9$, N(COR$^7$)OR$^{10}$, N(CO$_2$R$^7$)OR$^{10}$, C(O)NR$^{10}$(CR$^{12}$R$^{13}$)$_r$R$_7$, CO (CR$^{12}$R$^{13}$) pO(CR$^{14}$R$^{15}$)qCO$_2$R$_7$, CO(CR$^{12}$R$^{13}$) rOR$^7$, CO(CR$^{12}$R$^{13}$) pO(CR$^{14}$R$^{15}$)qR$^7$, CO(CR$^{12}$R$^{13}$)rNR$^8$R$^9$, OC(O)O (CR$^{12}$R$^{13}$)mNR$^8$R$^9$, OC(O)N(CR$^{12}$R$^{13}$)rR$^7$, O(CR$^{12}$R$^{13}$) mNR$^8$ R$^9$, NR$^{10}$C(O) (CR$^{12}$R$^{13}$)rR$^7$, NR$^{10}$C(O) (CR$^{12}$R$^{13}$) rOR$^7$, NR$^{10}$C(=NC) (CR$^{12}$R$^{13}$) rR$^7$, NR$^{10}$CO(CR$_{12}$R$_{13}$) rNR$^8$R$^9$, NR$^{10}$(CR$^{12}$R$^{13}$)mNR$^7$, NR$^{10}$(CR$^{12}$R$^{13}$)rCO$_2$R$_7$, NR$^{10}$(CR$^{12}$R$^{13}$)mNR$^8$R$^9$, NR$^{10}$(CR$^{12}$R$^{13}$)nSO$_2$(CR$^{14}$R$^{15}$) qR$^7$, CONR$^{10}$(CR$^{12}$R$^{13}$)nSO$_2$(CR$^{14}$R$^{15}$)qR$^7$, SO$_2$NR$^{10}$ (CR$^{12}$R$^{13}$)nCO(CR$^{14}$R$^{15}$)qR$^7$, and SO$_2$NR$^{10}$(CR$^{12}$R$^{13}$) nOR$^7$.

The term "aryl" refers to the phenyl, 1-naphthyl, and 2-naphthyl, preferably phenyl, as well as an aryl ring having a fused cycloalkyl, substituted cycloalkyl, heterocycloalkyl, or heteroaryl ring provided that the point of attachment is in the aryl ring, i.e.

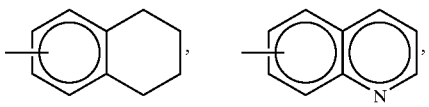

The term "substituted aryl" refers to such aryl groups as defined above having one, two, or three substituents selected from the group consisting of halogen, nitro, alkyl, substituted alkyl, alkenyl, cyano, cycloalkyl, substituted cycloalkyl, aryl, substituted aryl, heterocycloalkyl, heteroaryl, $OR^7$, $CO_2R^7$, C(O)$NR^8R^9$, OC(O)$R^7$, OC(O) $OR^7$, OC(O)$NR^8R^9$, $OCH_2CO_2R^7$, C(O)$R^7$, $NR^8R^9$, $NR^{10}C(O)R^7$, $NR^{10}C(O)OR^7$, $NR^{10}C(O)C(O)OR^7$, $NR^{10}C(O)C(O)NR^8R^9$, $NR^{10}C(O)C(O)$alkyl, $NR^{10}C(NCN)OR^7$, $NR^{10}C(O)NR^8R^9$, $NR^{10}C(NCN)NR^8R^9$, $NR^{10}C(NR^{11})NR^8R^9$, $NR^{10}SO_2NR^8R^9$, $NR^{10}SO_2R^7$, $SR^7$, S(O)$R^7$, $SO_2R^7$, $SO_3R^7$, $SO_2NR^8R^9$, $NHOR^7$, $NR^{10}NR^8R^9$, N(COR$^7$)OR$^{10}$, N(CO$_2$R$^7$)OR$^{10}$, C(O)NR$^{10}$(CR$^{12}$R$^{13}$)$_r$R$^7$, CO(CR$^{12}$R$^{13}$)pO(CR$^{14}$R$^{15}$)qCO$_2$R$^7$, CO(CR$^{12}$R$^{13}$)rOR$^7$, CO(CR$^{12}$R$^{13}$)pO(CR$^{14}$R$^{15}$)qR$^7$, CO(CR$^{12}$R$^{13}$)rNR$^8$R$^9$, OC(O)O(CR$^{12}$R$^{13}$) mNR$^8$R$^9$, OC(O) N(CR$^{12}$R$^{13}$)rR$^7$, O(CR$^{12}$R$^{13}$)mNR$^8$R$^9$, NR$^{10}$C(O) (CR$^{12}$R$^{13}$)rR$^7$, NR$^{10}$C(O) (CR$^{12}$R$^{13}$)rOR$^7$, NR$^{10}$C(=NC)(CR$^{12}$R$^{13}$)rR$^7$, NR$^{10}$CO (CR$^{12}$R$^{13}$)rNR$^8$R$^9$, NR$^{10}$CR$^{12}$R$^{13}$)mOR$^7$, NR$^{10}$(CR$^{12}$R$^{13}$) rCO$_2$R$_7$, NR$^{10}$(CR$^{12}$R$^{13}$)mNR$^8$R$^9$, NR$^{10}$(CR$^{10}$R$^{13}$)nSO$_2$ (CR$^{14}$R$^{15}$)qR$^7$, CONR$^{10}$(CR$^{12}$R$^{13}$ )nSO$_2$ (CR$^{14}$R$^{15}$ )qR$^7$, SO$_2$NR$^{10}$(CR$^{12}$R$^{13}$)nCO(CR$^{14}$R$^{15}$)qR$^7$, and SO$_2$NR$^{10}$ (CR$^{12}$R$^{13}$)mOR$^7$ as well as pentafluorophenyl.

The term "substituted monocyclic ring system of 5 or 6 carbon atoms" refers to one, two or three substituents selected from the group consisting of halogen, nitro, alkyl, substituted alkyl, alkenyl, cyano, oxo, $OR^7$ cycloalkyl, substituted cycloalkyl, aryl, substituted aryl, heterocycloalkyl, heteroaryl, $CO_2R^7$, $C(O)NR^8R^9$, $OC(O)R^7$, $OC(O)OR^7$, $OC(O)NR^8R^9$, $OCH_2CO_2R^7$, $C(O)R^7$, $NR^8$ $R^9$, $NR^{10}C(O)R^7$, $NR^{10}C(O)OR^7$, $NR^{10}C(O)C(O)OR^7$, $NR^{10}C(O)C(O)NR^8R^9$, $NR^{10}C(O)C(O)alkyl$, $NR^{10}C(NCN)OR^7$, $NR^{10}C(O)NR^8R^9$, $NR^{10}$ $C(NCN)NR^8R^9$, $NR^{10}C(NR^{11})NR^8R^9$, $NR^{10}SO_2,NR^8R^9$, $NR^{10}SO_2R^7$, $SR^7$, $S(O)R^7$, $SO_2R^7$, $SO_3R^7$, $SO_2NR^8R^9$, $NHOR^7$, $NR^{10}NR^8R^9$, $N(COR^7)OR^{10}$, $N(CO_2R^7)OR^{10}$, $C(O)NR^{10}(CR^{12}R^{13}),R^7$, $CO(CR^{12}R^{13})pO(CR^{14}R^{15})qCO_2R_7$, $CO(CR^{12}R^{13})rOR^7$, $CO(CR^{12}R^{13})pO(CR^{14}R^{15})qR^7$, $CO(CR^{12}R^{13})rNR^8R^9$, $OC(O)O(CR^{12}R^{13})mNR^8R^9$, $OC(O)N(CR^{12}R^{13})rR^7$, $O(CR^{12}R^{13})mNR^8R^9$, $NR^{10}C(O)$ $(CR^{12}R^{13})rR^7$, $NR^{10}C(O)$ $(CR^{12}R^{13})rOR^7$, $NR^{10}C(=NC)$ $(CR^{12}R^{13})rR^7$, $NR^{10}CO(CR^{12}R^{13})rNR^8R^9$, $NR^{10}(CR^{12}R^{13})mOR^7$, $NR^{10}(CR^{12}R^{13})$ $rCO_2R_7$, $NR^{10}(CR^{12}R^{13})$ $mNR^8R^9$, $NR^{10}(CR^{12}R^{13})nSO_2$ $(CR^{14}R^{15})qR^7$, $CONR^{10}(CR^{12}R^{13})nSO_2$ $(CR^{14}R^{15})qR^7$, $SO_2NR^{10}(CR^{12}R^{13})nCO(CR^{14}R^{15})qR^7$, and $SO_2NR^{10}(CR^{12}R^{13})mOR^7$, The term "heterocycloalkyl" refers to substituted and unsubstituted saturated or partially saturated monocyclic rings of 3 to 7 members and bicyclic rings of 7 to 11 members having one or two O or S atoms and/or one to four N atoms provided that the total number of heteroatoms is four or less and that the heterocycloalkyl ring contains at least one carbon atom. The nitrogen and sulfur atoms may optionally be oxidized, and the nitrogen atoms may optionally be quaternized. The bicyclic heterocycloalkyl ring may also contain a two or three carbon bridge between available carbon or nitrogen atoms. The bicyclic heterocycloalkyl rings may also have a cycloalkyl, substituted cycloalkyl, aryl, substituted aryl, heterocycloalkyl, or heteroaryl ring fused to the monocyclic ring provided that the point of attachment is through an available carbon or nitrogen atom of the heterocycloalkyl ring. Also included are spiroheterocycloalkyl rings wherein a carbon atom of the heterocycloalkyl ring is in common with a second heterocycloalkyl ring, a cycloalkyl ring, or a substituted cycloalkyl ring again provided that the point of attachment is through an available carbon or nitrogen atom of the heterocycloalkyl ring. The heterocycloalkyl ring can have one, two or three substituents on available carbon or nitrogen atoms selected from the group consisting of halogen, nitro, alkyl, substituted alkyl, alkenyl, cyano, cycloalkyl, substituted cycloalkyl, aryl, substituted aryl, heterocycloalkyl, heteroaryl, oxo, $OR^7$, $CO_2R^7$, $C(O)NR^8R^9$, $OC(O)R^7$, $OC(O)OR^7$, $OC(O)NR^8R^9$, $OCH_2CO_2R^7$, $C(O)R^7$, $NR^8R^9$, $NR^{10}C(O)R^7$ $NR^{10}C(O)OR^7$, $NR^{10}C(O)C(O)OR^7$, $NR^{10}C(O)C(O)NR^8R^9$, $NR^{10}C(O)C(O)alkyl$, $NR^{10}C(NCN)OR^7$, $NR^{10}C(O)NR^8R^9$, $NR^{10}C(NCN)NR^8R^9$, $NR^{10}C(NR^{11})NR^8R^9NR^{10}SO_2 NR^8R^9$, $NR^{10}SO_2R^7$, $SR^7$, $S(O)R^7$, $S_2R^7$ $SO_3R^7$, $SO_2NR^8R^9$, $NHOR^7$, $NR^{10}NR^8R^9$, $N(COR^7)OR^{10}$, $N(CO_2R^7)OR^{10}$, $C(O)NR^{10}(CR^{12}R^{13})rRO^7$, $CO(CR^{12}R^{13})pO(CR^{14}R^{15})qCO_2R_7$, $CO(CR^{12}R^{13})rOR^7$, $CO(CR^{12}R^{13})pO(CR^{14}R^{15})qR^7$, $CO(CR^{12}R^{13})rNR^8R^9$, $OC(O)O(CR^{12}R^{13})mNR^8R^9$, $OC(O)N(CR^{12}R^{13})rOR^7$, $O(CR^{12}R^{13})mNR^8R^9$, $NR^{10}C(O)$ $(CR^{12}R^{13})rR^7$, $NR^{10}C(O)$ $(CR^{12}R^{13})rOR^7$, $NR^{10}C(=NC)$ $(CR^{12}R^{13})rR^7$, $NR^{10}CO(CR^{12}R^{13})rNR^8R^9$, $NR^{10}(CR^{12}R^{13})mOR^7$, $NR^{10}(CR^{12}R^{13})rCO_2R_7$, $NR^{10}$ $(CR^{12}R^{13})mNR^8R^9$, $NR^{10}(CR^{12}R^{13})nSO_2(CR^{14}R^{15})qR^7$, $CONR^{10}(CR^{12}R^{13})nSO_2$ $(CR^{14}R^{15})qR^7$, $SO_2NR^{10}(CR^{12}R^{13})nCO(CR^{14}R^{15})qR^7$, and $SO_2NR^{10}(CR^{12}R^{13})mOR^7$.

Exemplary monocyclic heterocycloalkyl groups include pyrrolidinyl, pyrrolinyl, pyrazolinyl, pyrazolidinyl, oxetanyl, imidazolinyl, imidazolidinyl, oxazolidinyl, isothiazolidinyl, isoxazolinyl, thiazolidinyl, tetrahydrofuryl, piperidinyl, piperazinyl, tetrahydrothiopyranyl, tetrahydropyranyl, morpholinyl, thiamorpholinyl, thiamorpholinyl sulfoxide, thiamorpholinyl sulfone, tetrahydrothiopyranylsulfone, 1,3-dioxolanyl, tetrahydro-1, 1-dioxothienyl, dioxanyl, thietanyl, thiiranyl, triazolinyl, triazolidinyl, etc.

Exemplary bicyclic heterocycloalkyl groups include indolinyl, quinuclidinyl, tetrahydroisoquinolinyl, benzimidazolinyl, chromanyl, dihydrobenzofuran, dihydrofuro[3,4-b] pyridinyl, dihydroisoindolyl, dihydroquinazolinyl (such as 3,4-dihydro-4-oxo-quinazolinyl), benzofurazanyl, benzotriazolinyl, dihydrobenzofuryl, dihydrobenzothienyl, dihydrobenzothiopyranyl, dihydrobenzothiopyranyl sulfone, dihydrobenzopyranyl, isoindolinyl, isochromanyl, benzodioxolyl, tetrahydroquinolinyl, etc.

Exemplary spirocyclic heterocycloalkyl groups include 1-aza[4.5]spirodecane, 2-aza[4.5]spirodecane, 1-aza[5.5] spiroundecane, 2-aza[5.5]spiroundecane, 3-aza[5.5] spiroundecane, etc.

The term "heteroaryl" refers to substituted and unsubstituted aromatic 5 or 6 membered monocyclic groups and 9 or 10 membered bicyclic groups which have at least one heteroatom (O,S or N) in at least one of rings. Each ring of the heteroaryl groups containing a heteroatom can contain one or two O and S atoms and/or from one to four N atoms provided that the total number of heteroatoms in each ring is four or less. The bicyclic heteroaryl rings are formed by fusing a cycloalkyl, substituted cycloalkyl, aryl, substituted aryl, heterocycloalkyl, or heteroaryl group to the monocyclic heteroaryl ring as defined above. The heteroaryl group is attached via an available carbon or nitrogen in the aromatic heteroaryl ring. The nitrogen and sulfur atoms may optionally be oxidized and the nitrogen atoms may optionally be quaternized. The heteroaryl ring system may be substituted at an available carbon or nitrogen by one, two, or three substituents selected from the group consisting of halogen, nitro, alkyl, substituted alkyl, alkenyl, cyano, cycloalkyl, substituted cycloalkyl, aryl, substituted aryl, heterocycloalkyl, heteroaryl, $OR^7$, $CO_2R^7$, $C(O)NR^8R^9$, $OC(O)R^7$, $OC(O)OR^7$, $OC(O)NR^8R^9$, $OCH_2CO_2R^7$, $C(O)R^7$, $NR^8R^9$, $NR^{10}C(O)R^7$, $NR^{10}C(O)OR^7$, $NR^{10}C(O)C(O)OR^7$, $NR^{10}C(O)C(O)NR^8R^9$, $NR^{10}C(O)C(O)alkyl$, $NR^{10}C(NCN)OR^7$, $NR^{10}C(O)NR^8R^9$, $NR^{10}C(NCN)NR^8R^9$, $NR^{10}C(NR^{11})NR^8R^9$, $NR^{10}SO_2NR^8R^9$, $NR^{10}SO_2R^7$, $SR^7$, $S(O)R^7$, $SO_2R^7$, $SO_3R^7$, $SO_2NR^8R^9NHOR^7NR^{10}NR^8R^9$, $N(COR^7)OR^{10}$, $N(CO_2R^7)OR^{10}$, $C(O)NR^{10}(CR^{12}R^{13}),R^7$, $CO(CR^{12}R^{13})pO(CR^{14}R^{15})qCO_2R_7$, $CO$ $(CR^{12}R^{13})rOR^7$, $CO(CR^{12}R^{13})pO$ $(CR^{14}R^{15})qR^7$, $CO$ $(CR^{12}R^{13})rNR^8R^9$, $OC(O)O(CR^{12}R^{13})mNR^8R^9$, $OC(O)N(CR^{12}R^{13})rR^7$, $O(CR^{12}R^{13})mNR^8R^9$, $NR^{10}C(O)(CR^{12}R^{13})rR^7$, $NR^{10}C(O)(CR^{12}R^{13})rOR^7$, $NR^{10}C(=NC)$ $(CR^{12}R^{13})rR^7$, $NR^{10}CO(CR^{12}R^{13})rNR^8R^9$, $NR^{10}(CR^{12}R^{13})mOR^7$, $NR^{10}(CR^{12}R^{13})rCO_2R_7$, $NR^{10}(CR^{12}R^{13})mNR^8R^9$, $NR^{10}(CR^{12}R^{13})nSO_2(CR^{14}R^{15})qR^7$, $CONR^{10}(CR^{12}R^{13})nSO_2(CR^{14}R^{15})qR^7$, $SO_2NR^{10}(CR^{12}R^{13})nCO(CR^{14}R^{15})qR^7$, and $SO_2NR^{10}(CR^{12}R^{13})mOR^7$.

Exemplary monocyclic heteroaryl groups include pyrrolyl, pyrazolyl, imidazolyl, oxazolyl, isoxazolyl, thiazolyl, thiadiazolyl, isothiazolyl, pyridinyl, furyl, thienyl, oxadiazolyl, 2-oxazepinyl, azepinyl, pyrazinyl, pyrimidinyl, pyridazinyl, triazinyl, triazolyl, etc.

Exemplary bicyclic heteroaryl groups include benzothiazolyl, benzoxazolyl, benzothienyl, benzofuryl, quinolinyl, quinolinyl-N-oxide, isoquinolinyl, benzimidazolyl, benzopyranyl, indolizinyl,cinnolinyl, quinoxalinyl, indazolyl, pyrrolopyridyl, furopyridinyl (such as furo [2,3-c]pyridinyl, furo[3,1-b]pyridinyl or furo[2,3-b] pyridinyl), benzisothiazolyl, benzisoxazolyl, benzodiazinyl, benzothiopyranyl, benzotriazolyl, benzpyrazolyl, naphthyridinyl, phthalazinyl, purinyl, pyridopyridyl, quinazolinyl, thienofuryl, thienopyridyl, thienothienyl, etc.

$R^{12}$ and $R^{14}$ are independently selected from hydrogen and alkyl of 1 to 4 carbons.

$R^{13}$ and $R^{15}$ are independently selected from hydrogen, alkyl of 1 to 4 carbons, and substituted alkyl of 1 to 4 carbons.

n is zero or an integer from 1 to 4.

m is an integer from 2 to 6.

p is an integer from 1 to 3.

q is zero or an integer from 1 to 3.

r is zero or an integer from 1 to 6.

"IMPDH-associated disorders" refers to any disorder or disease state in which inhibition of the enzyme IMPDH (inosine monophosphate dehydrogenase, EC.1.1.205, of which there are presently two known isozymes referred to as IMPDH type 1 and IMPDH type 2) would modulate the activity of cells (such as lymphocytes or other cells) and thereby ameliorate or reduce the symptoms or modify the underlying cause(s) of that disorder or disease. There may or may not be present in the disorder or disease an abnormality associated directly with the IMPDH enzyme. Examples of IMPDH-associated disorders include transplant rejection and autoimmune disorders, such as rheumatoid arthritis, multiple sclerosis, juvenile diabetes, asthma, and inflammatory bowel disease, as well as inflammatory disorders, cancer and tumor disorders, T-cell mediated hypersensitivity diseases, ischemic or reperfusion injury, viral replication diseases, proliferative disorders and vascular diseases.

As used herein the term "treating" includes prophylactic and therapeutic uses, and refers to the alleviation of symptoms of a particular disorder in a patient, the improvement of an ascertainable measurement associated with a particular disorder, or the prevention of a particular immune response (such as transplant rejection). The term "patient" refers to a mammal, preferably a human.

The compounds of this invention may contain one or more asymmetric carbon atoms and thus may occur as racemates and racemic mixtures, single enantiomers, diastereomeric mixtures and individual diastereomers. All such isomers of the compounds disclosed herein are expressly included within the scope of the present invention. Each stereogenic carbon may be of the R or S configuration.

Combinations of substituents and variables thereof that result in stable compounds are also contemplated within the present invention. The term "stable" as used herein refers to compounds which possess stability sufficient to allow manufacture and which maintain their integrity for a sufficient period of time to be useful as a therapeutic or diagnostic agent.

As used herein, the compounds of this invention are defined to include pharmaceutically acceptable derivatives and prodrugs thereof. A "pharmaceutically acceptable derivative or prodrug" includes any pharmaceutically acceptable salt, ester, salt of an ester, or other derivative of a compound of the present invention which, upon administration to a subject, is capable of providing (directly or indirectly) a compound of the invention. Particularly favored derivatives and prodrugs are those that increase the bioavailability of the compounds of the present invention when such compound is administered to a subject (e.g., by allowing an orally administered compound to be more readily absorbed into the blood) or which enhance delivery of the parent compound to a biological compartment (e.g., the brain or lymphatic system) relative to the parent species. Preferred prodrugs include derivatives where a group that enhances aqueous solubility or active transport through the gut membrane is appended to a compound of the present invention.

Pharmaceutically acceptable salts of the compounds disclosed herein include those derived from pharmaceutically acceptable inorganic and organic acids and bases known to those skilled in the art. Examples of suitable acid salts include, but are not limited to, the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, inalonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, trifluoroacetic, tosylate and undecanoate. Other acids, for example oxalic, while not in themselves pharmaceutically acceptable, may be employed in the preparation of salts useful as intermediates in obtaining the compounds of the present invention and their pharmaceutically acceptable acid additional salts.

Salts derived from appropriate bases include, but are not limited to, the following: alkali metal (e.g., sodium), alkaline earth metal (e.g., magnesium), ammonium and $N-(C_{1-4}\ alkyl)_4+$ salts. The present invention also envisions the quaternization of any basic nitrogen-containing groups of the compounds disclosed herein. Water- or oil-soluble or dispersible products may be obtained by such quaternization.

METHODS OF PREPARATION

The compounds of the present invention may be synthesized using conventional techniques known in the art. Advantageously, these compounds are conveniently synthesized from readily available starting materials. Following are general synthetic schemes for manufacturing compounds of the present invention. These schemes are illustrative and are not meant to limit the possible techniques one skilled in the art may use to manufacture compounds disclosed herein. Different methods will be evident to those skilled in the art. Additionally, the various steps in the synthesis may be performed in an alternate sequence or order to give the desired compound(s). All documents cited herein are incorporated herein by reference in their entirety.

Compounds of the present invention can be made by many methods, which will be known to one skilled in the art of organic chemistry. In general, the time taken to complete a reaction procedure will be judged by the person performing the procedure, preferably with the aid of information obtained by monitoring the reaction by methods such as HPLC or TLC. A reaction does not have to go to completion to be useful to this invention. The preparation of heterocycles useful to this invention are described in the series of books: "Comprehensive Heterocyclic Chemistry, The Structure, Reactions, Synthesis and Uses, of Heterocyclic Compounds" Katritzky, A. R., Rees, C. W. Eds Pergamon Press New York, First edition 1984, and "Comprehensive Heterocyclic Chemistry II, A Review of the Literature 1982–1995. The Structure, Reactions, Synthesis and Uses, of Heterocyclic Compounds" Katritzky, A. R., Rees, C. W. and Scriven, E., F. Eds Pergamon Press New York, 1996.

Amines such as anilines or heterocyclic amines, useful for the preparation of compounds useful to this invention may be commercially available or readily prepared by many methods known to one skilled in the art of organic chemistry, and are described in "Comprehensive Organic Transformations A Guide to Functional Group Preparation" pp 385–439. Richard C. Larock 1989 VCH Publishers, Inc. Examples include but are not limited to reduction of a nitro group, and reduction of an azide. Methods for the production of amines useful to this invention are outlined in Schemes 1a-1f.

A general method for the synthesis of the anilines such as (1a.4) useful in this invention can be performed by metal catalyzed cross coupling methods known in the literature. The simplest case is a Suzuki type cross coupling (Miyaura, N., Yanagi, T. Suzuki, A., Synth. Comm. 11(7):513–519 (1981); A. Suzuki et. al., J. Am. Chem. Soc. 111:513 (1989); and V. N. Kalinin, Russ. Chem. Rev. 60:173 (1991)) of an aryl boronic acid or ester (1a.1) (as shown below) with an appropriate bromoheterocycle in the presence of a suitable catalyst such as tetrakis (triphenylphosphine) palladium. After the cross coupling has been performed the product may-be deprotected. The choice of protecting group and its method of removal will be readily apparent to one skilled in the art of organic chemistry. Such considerations and methods are, for example, described by Greene, Theodora W. and Wuts, Peter G. M. in "Protective Groups in Organic Synthesis." 2nd Ed., (1991) Publisher: (John Wiley and Sons, Inc., New York, N.Y. For example, if the protecting group is acetyl the product may be deprotected by treatment with aqueous potassium hydroxide at a concentration of 0.5N to 5 N at room temperature to 100° C. for a period between 0.5h and 24h.

For example aryl boronic acid (1a.5) may react with the known 5-bromothiazole (1a.6) in the presence of tetrakis (triphenylphosphine) palladium (0), to provide (1a.7) which may be deprotected by an appropriate method.

Scheme 1a

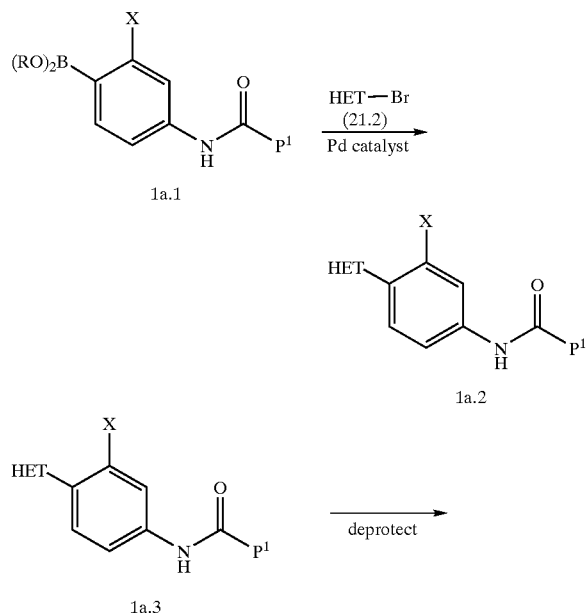

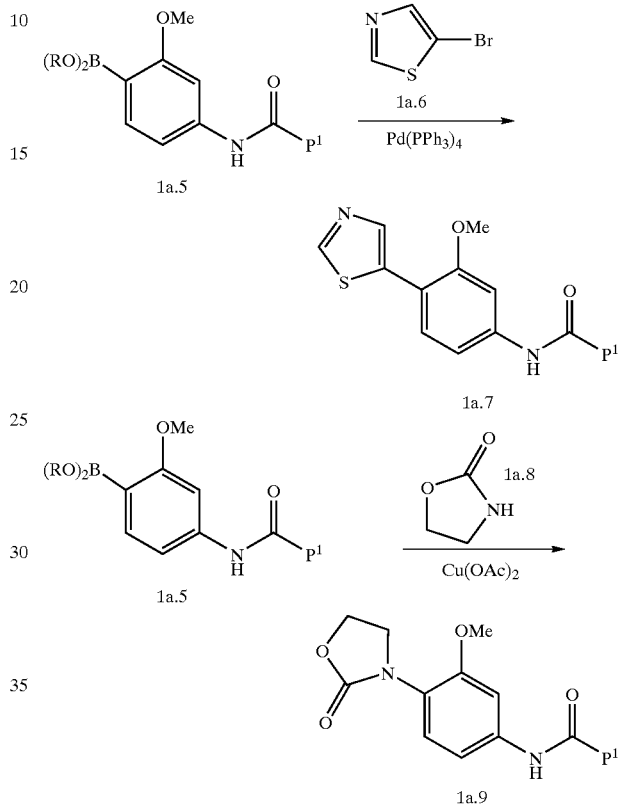

R = H, Alkyl
X = H, OMe, etc.
HET = a 5 or 6 membered ring containing at least one O, N, S atom with an unsaturated bond directly attached to the bromine
P$^1$ = alkyl, O-benzyl, O-tertbutyl, ect.

Copper has been recently been shown to be an effective catalyst for cross coupling of aryl boronic acids to N-unsubstituted heterocycles as described by Chan et al., Tetrahed. Lett. 39:2933–2936 (1998); and Lam et al., Tetrahed. Lett. 39:2941–2944 (1998). This results in compounds in which the heterocycle is attached to the aryl ring through nitrogen rather than carbon. For example aryl boronic acid (1a.5) may react with oxazolone (1a.8) in the presence of copper (II) acetate in the presence of an amine base such as pyridine to provide intermediate (la.9) which may be deprotected by an appropriate method In general aryl boronic acids and esters, 1b.3, where X is not Br or I, may be prepared as shown in Scheme Ib, from the corresponding arylbromide (1b.1) by treatment with a palladium catalyst such as [1,1'-Bis(diphenylphosphino)-ferrocene] dichloropalladium (II) and bis(pinacolato) diboron, (1b.2), as reported by Ishayama et al., J. Org. Chem., (1995) 7508–7510. Aryl boronic esters may be converted to the corresponding boronic acid by several methods including treatment with aqueous HCl. In a variation of the synthesis, the nitrogen may be masked as a nitro group and later reduced by several means including metal reductions, such as by treatment with tin chloride in HCl or by refluxing the nitro compound with zinc in the presence of CaCl$_2$ in a solvent such as ethanol, or in certain cases the nitro group may be reduced by catalytic hydrogenation in the presence of catalysts such as palladium on carbon. The conditions for the reduction of nitro groups are detailed in several references including Hudlicky, M., "Reductions in Organic Chemistry", 2nd Ed., ACS Monograph 188, 1996, pp 91–101, American Chemical Society, Washington, DC. A second variation of the synthesis allows the aryl bromide to remain through the entire synthesis and elaborated to the boronic acid at the end. This may eliminate the need for a protecting group.

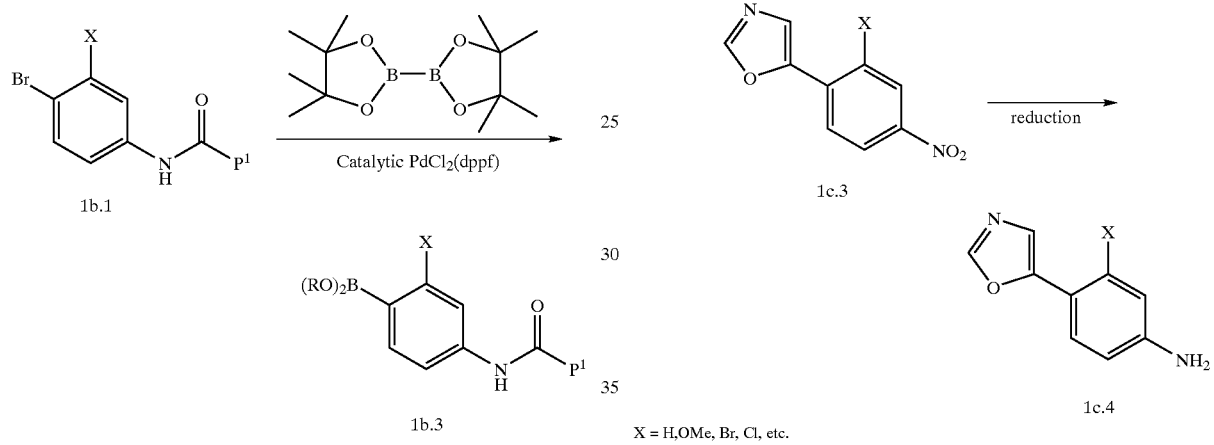

X = H, OMe, Cl, etc.
P1 = alkyl Obenzyl, Oterbutyl, etc.

In certain cases it may be more expedient to construct the heterocyclic ring by other methods. A general method for the synthesis of 5-membered heterocycles includes the 1,3-dipolar cycloaddition reaction, which is well known to one skilled in the art of organic chemistry and is described by Padwa, Albert, Editor in " 1,3-Dipolar Cycloaddition Chemistry, Vol. 2" (1984) John Wiley and Sons, New York, N.Y.; and Padwa, Albert; Editor. in "1,3-Dipolar Cycloaddition Chemistry, Vol. 1" (1984) John Wiley and Sons, New York, N.Y. For example oxazoles may be prepared by 1,3 dipolar cycloaddtion of the corrosponding aldehyde (1c.1) and (p-tolylsulfonyl)methyl isocyanate (TOSMIC) (1c.2) as shown in scheme Ic. The aldehyde may be commercially available or prepared from the corresponding methyl group by oxidation with reagents such as CrO$_3$, MnO$_2$, and ammonium cerium (IV) nitrate by methods well known to one skilled in the art of organic chemistry and is described in Hudlicky, M., "Oxidations in Organic Chemistry", ACS Monograph 186 (1990), American Chemical Society, Washington, DC. The nitro group in intermediate (1c.3), is reduced to an amine (1c.4), as discussed above.

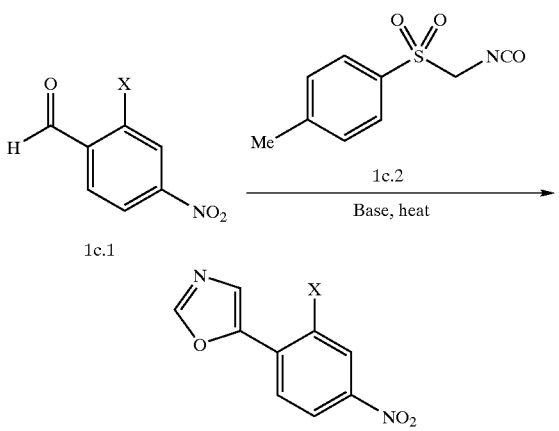

X = H, OMe, Br, Cl, etc.

An alternative method of producing amines useful to this invention is by nucleophilic attack on an electron deficient ring system as outlined in Scheme 1d. Halonitrobenzenes (1d.1), are either commercially available or readily prepared by methods known to one skilled in the art of organic synthesis. Displacement with a variety of nucleophiles produce compounds of structure (1d.2). In one example heating (1d.3) with a nucleophilic heterocycle such as triazole with or without the addition of a base provides the intermediate nitro compound which may be reduced as previously described to provide amines (1d.4). Alternatively simple organic nucleophiles such as cyanide can be reacted with halonitrobenzene (1d.5) to provide an intermediate nitro-compound which can be reduced by many methods to an amine (1d.6).

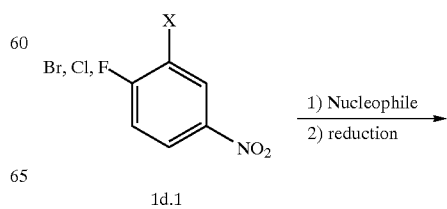

-continued

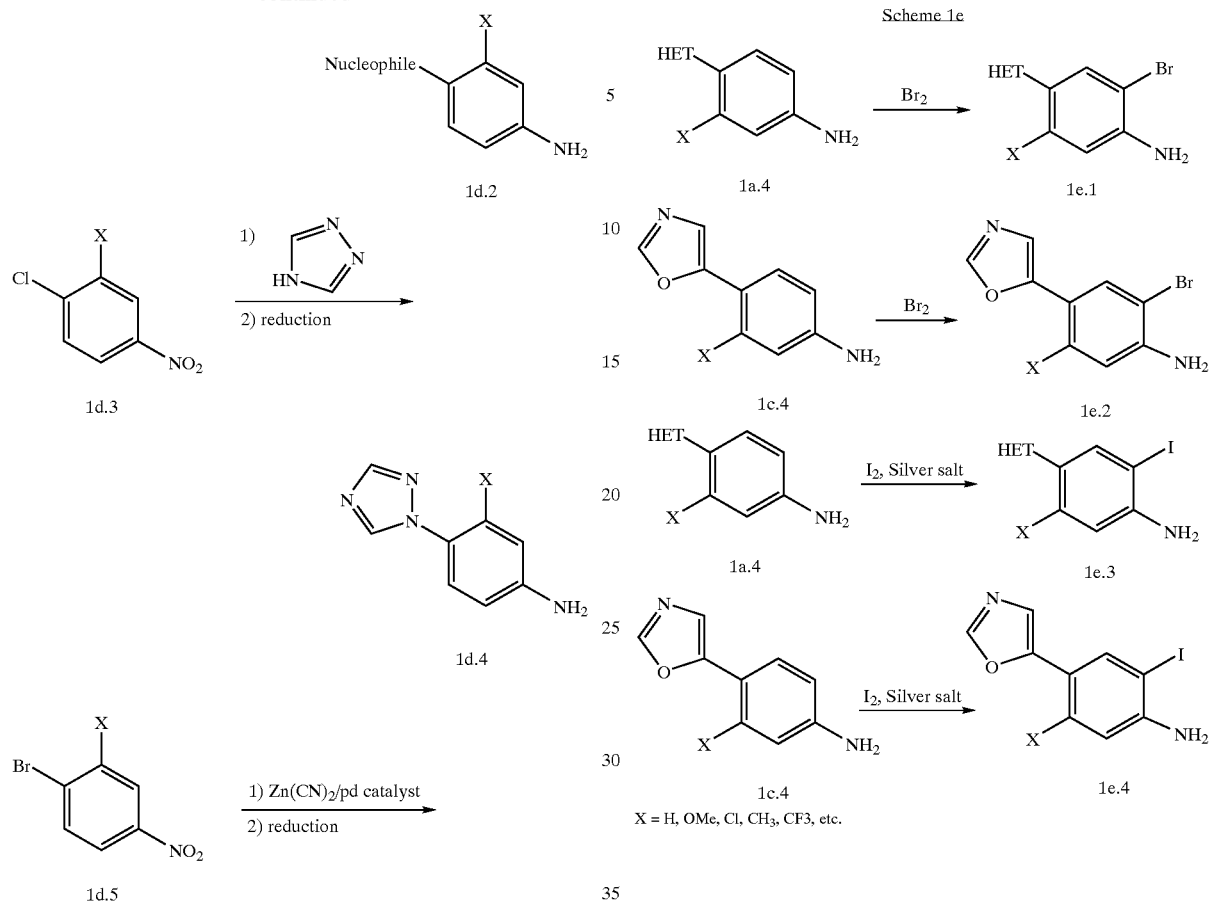

In some cases it will be useful to have an ortho-bromo or ortho-iodo aniline as an intermediate for the synthesis of heterocycles useful for this invention as described in scheme Ie. Bromination of anilines may be accomplished in many cases by simply dissolving the aniline, such as (1a.4) and (1c.4), in a suitable solvent such as methylene chloride, chloroform, acetic acid or hydrochloric acid, and treating with one equivalent of bromine, at a temperature from −78 to 40° C. to provide aniline (1e.1 and 1e.2). In some cases the aniline may be protected with a group such as acetate. In this case the bromination can often be accomplished by the addition of a Lewis acid catalyst such as iron, or $FeBr_3$. Iodination can be effected in a manner analogous to that described for bromine, but may also benefit from the addition of silver salts such as silver benzoate, silver triflate, silver trifluoroacetate, or periodic acid, to provide aniline (1e.3) and (1e.4).

The synthesis of useful aniline intermediates which contain an ortho keto group (1f.3) is depicted in Scheme 1f. They may be prepared from anilines (1e.1) and (1e.2, shown) by palladium mediated couping with an appropriate alkoxyvinyl stannane (1f.1) to produce the enol-ether (1f.2). Hydrolysis of the enol-ether with dilute acid provides the ketone (1f.3)

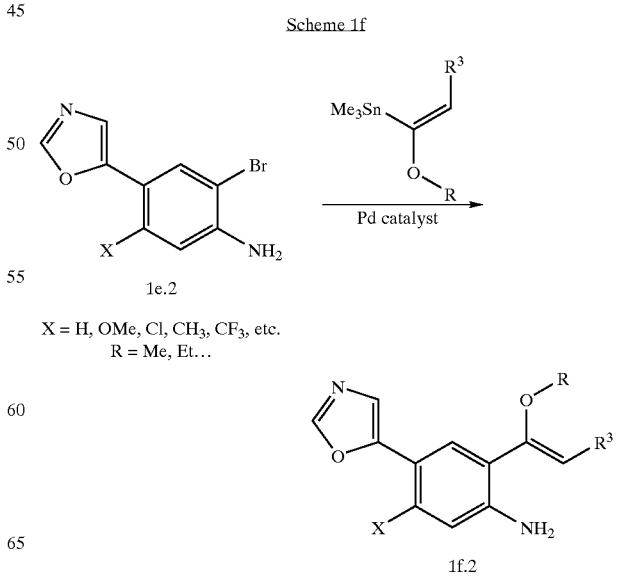

-continued

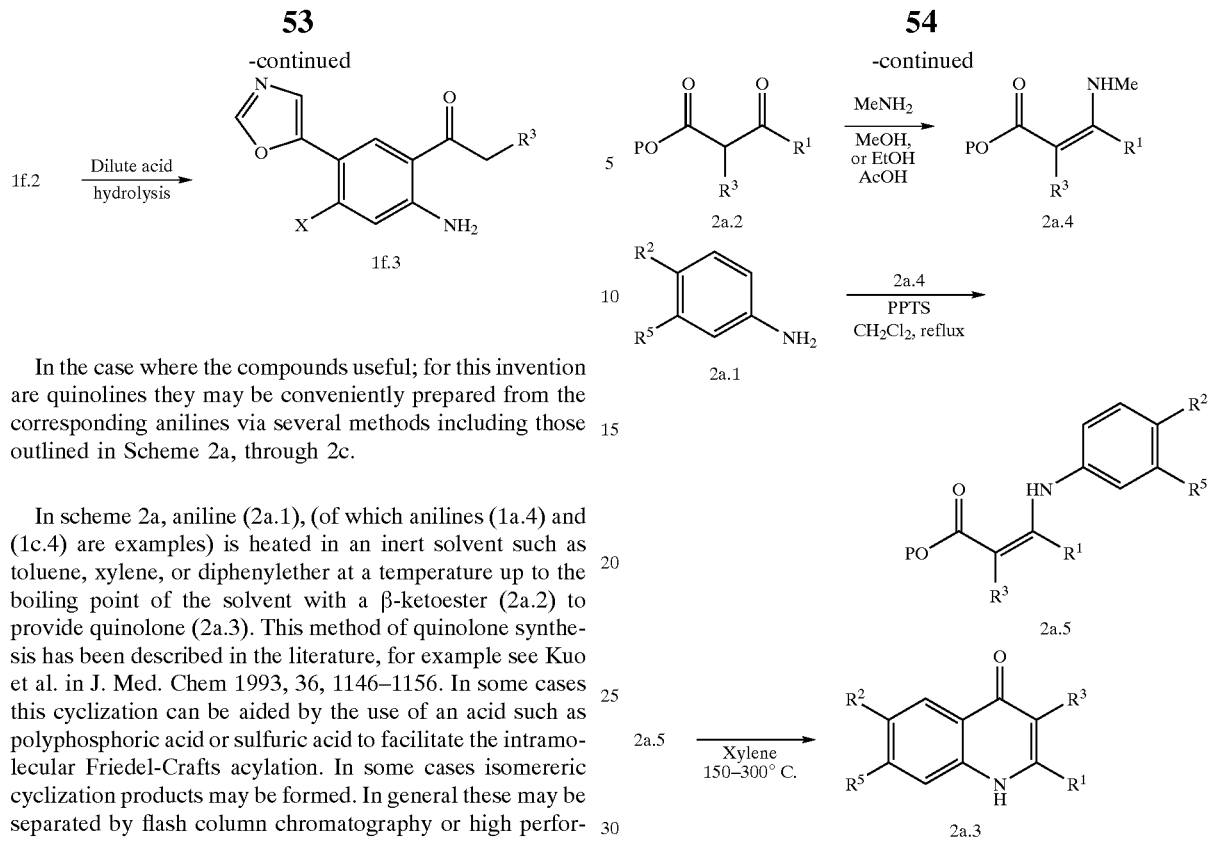

In the case where the compounds useful; for this invention are quinolines they may be conveniently prepared from the corresponding anilines via several methods including those outlined in Scheme 2a, through 2c.

In scheme 2a, aniline (2a.1), (of which anilines (1a.4) and (1c.4) are examples) is heated in an inert solvent such as toluene, xylene, or diphenylether at a temperature up to the boiling point of the solvent with a β-ketoester (2a.2) to provide quinolone (2a.3). This method of quinolone synthesis has been described in the literature, for example see Kuo et al. in J. Med. Chem 1993, 36, 1146–1156. In some cases this cyclization can be aided by the use of an acid such as polyphosphoric acid or sulfuric acid to facilitate the intramolecular Friedel-Crafts acylation. In some cases isomereric cyclization products may be formed. In general these may be separated by flash column chromatography or high performance liquid chromatography.

A modification of the above the synthesis has been reported by Toda, J. et al. in Heterocycles 1994, 38, 2091–2097. In this method the beta keto ester (2a.2) is converted to an enamine (2a.4) by refluxing with an amine such as methylamine in an alcoholic solvent in the presence of acetic acid. The enamine (2a.4) is then reacted with an aniline such as (2a.1) in an inert solvent such as benzene, methylene chloride, or carbon tetrachloride in the presence of an equivalent of pyridinium p-toluenesulfonate (PPTS) to effect an N-N exchange reaction to produce enamine (2a.5). This can be cyclized to the quinolone by heating in an inert solvent such as xylene at a temperature between 150–300° C. In some cases, as mentioned above, an acid catalyst may be added to aid in the intramolecular Friedel-Crafts acylation.

Scheme 2a

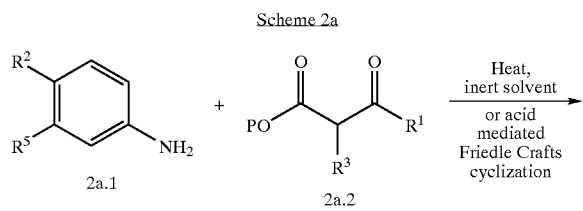

P = Me, Et, Pr, Bn...

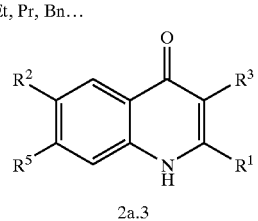

β-ketoesters such as (IIa.2) useful for this invention are either commercially available or readily prepared from the corresponding carboxylic acids or esters by several means including, that reported by Clay, R. J., et al., in Synthesis, 1993, 290–292, and those outlined in chapter 2 of "Advanced Organic Chemistry" $3^{rd}$ edition (1990) by Carey, F. A., and Sundberg R. J., Plenum Press, New York, N.Y.

An alternative quinolone synthesis starting from aniline (1e.3) (of which aniline 1e.4 is an example) is depicted in Scheme 2b. This method of quinolone synthesis has been described in the literature, for example see Kalinin, V. N., et. al. Tetrahedron Lett. 1992, 33, 373–376, and Torii, S., et. al. in Tetrahedron 1993, 42, 6773–6784. The aniline (1e.3) is heated between 60–160° C. in the presence of an acetylene (2d.1) and 0.1–5 mol % of a palladium catalyst such as tetrakistriphenylphosphine palladium (0),dichlorobis (triphenylphosphine)palladium (II), or dichloro(1,1'-bis (diphenylphosphino)ferrocene palladium(II), in an atmosphere of carbon monoxide (3–40 atmospheres) in a steel autoclave.

Scheme 2b

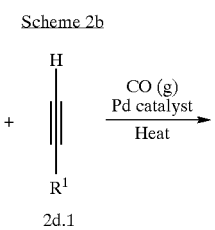

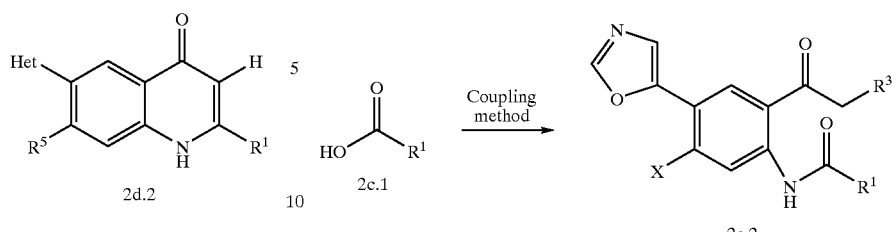

2d.2

Acetylenes 2d.1 are either commercially available or may be prepared by several methods including, palladium catalyzed coupling with an aryl or vinyl bromide or iodide with trimethylsilylacetylene as initially described by Takahashi, S. et. al. in Synthesis 1980, 627. The trimethylsilyl protecting group may be removed by treatment with aqueous base or with a fluoride source such as tetrabutylammonium fluoride. An alternative sythesis of terminal acetylenes is commonly known as the Corey-Fuchs sythesis, for examples see Wang, Z. et al. J. Org. Chem. 2000, 65, 1889–91, and references contained therein. The Corey-Fuchs syntheses and its modifications start with an appropriately substituted aldehyde. The aldehydes useful for this invention are either commercially available or readily prepared by oxidation of an alcohol by many methods as described by Hudlicky, M. "Oxidations in Organic Chemistry", ACS Monograph 186, 1990, American Chemical Society, Washington, D.C.

Another alternative synthesis of quinolones has been reported in the literature for example see, Li, L., et al. in J. Med. Chem. 1994, 37, 3400–3407, and is depicted in Scheme 2c. Aniline (1f.3) is coupled with an carboxylic acid (2c.1) to form an amide (2c.2). The coupling is carried out using any of the many methods for the formation of amide bonds known to one skilled in the art of organic synthesis. These methods include but are not limited to conversion of the acid to the corresponding acid chloride, or use of standard coupling procedures such as the azide method, mixed carbonic acid anhydride (isobutyl chloroformate) method, carbodiimide (dicyclohexylcarbodiimide, diisopropylcarbodiimide, or water-soluble carbodiimides) method, active ester (p-nitrophenyl ester, N-hydroxysuccinic imido ester) method, carbonyldiimidazole method, phosphorus reagents such as BOP-Cl. Some of these methods (especially the carbodiimide) can be enhanced by the addition of 1-hydroxybenzotriazole. The amide (2c.2) is then treated with a base such as potassium tert-butoxide to effect cyclization to the quinolone (2c.3).

Scheme 2c

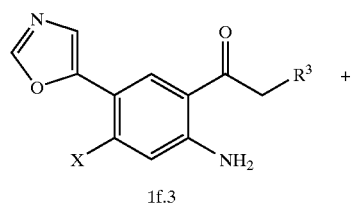

1f.3

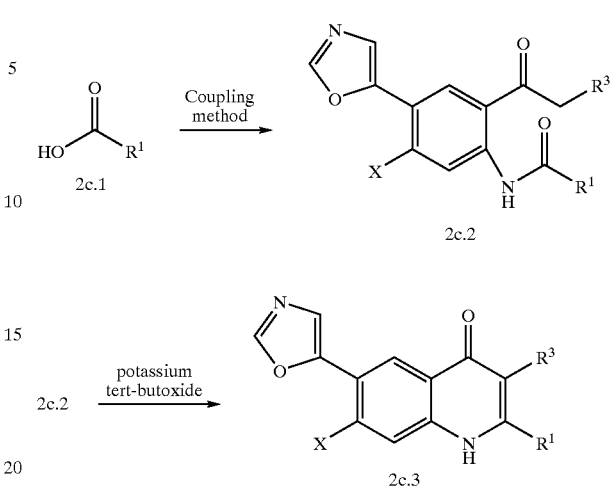

Scheme 3a

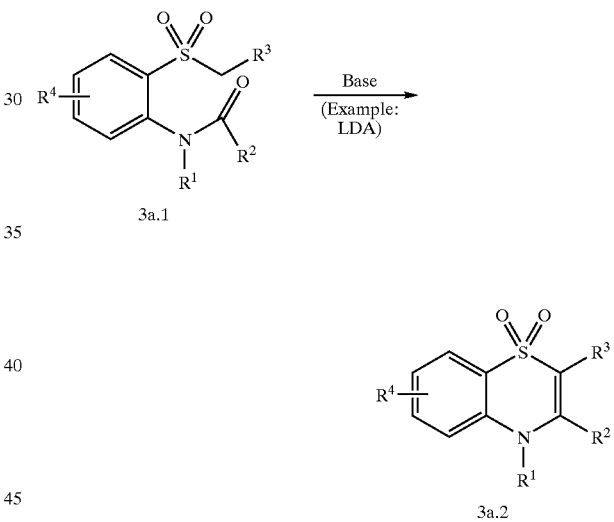

The the synthesis of dioxides of benzothiazines (3a.2) has been reported in the literature, for example see, Florio at al. in J. Chem. Soc. Perkin Trans. I. 1984, 1899–1903. This chemistry is depicted in scheme 3a.

Scheme 3b

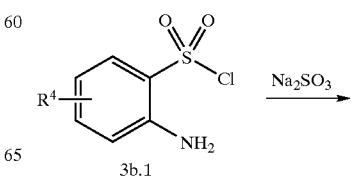

3b.1

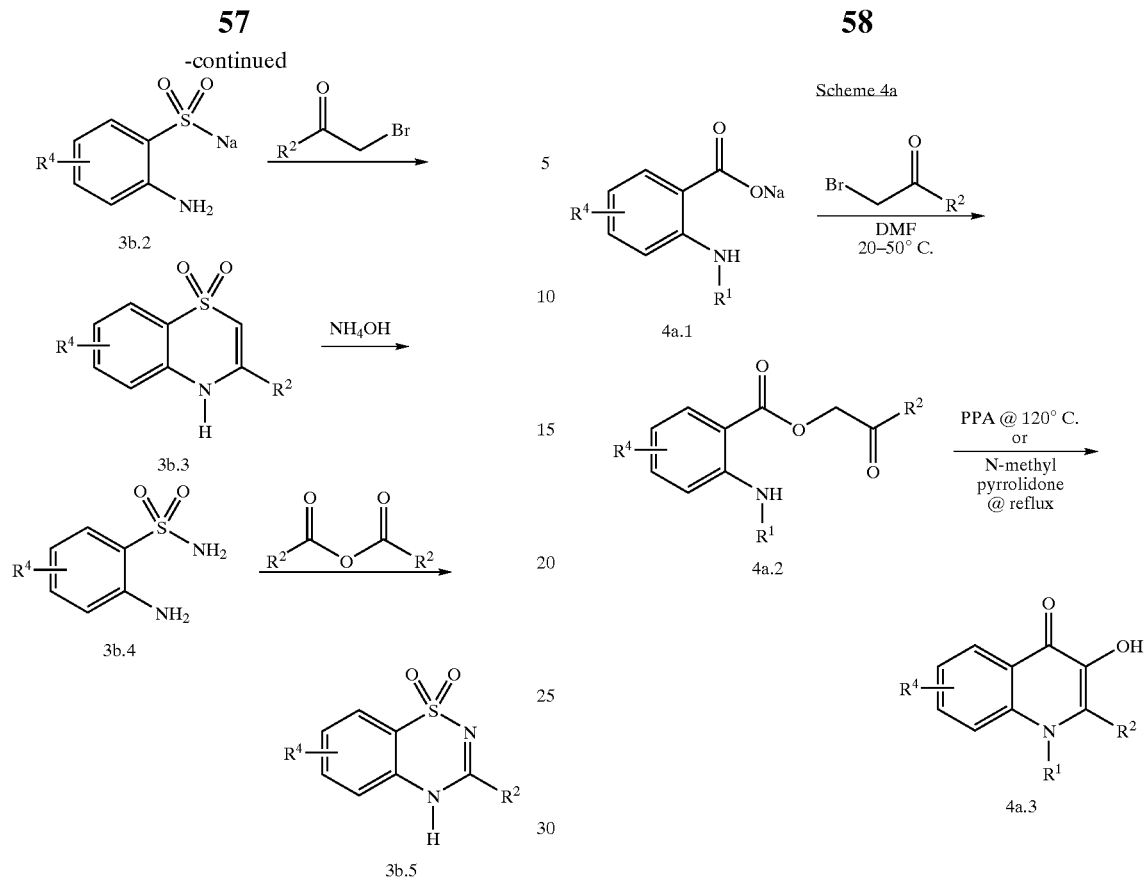

An alternative synthesis of benzothiazines (3b.3) and benzothiadiazines (3b.5) has been reported in the literature, for example, Vysokov et al. in Russian J. of Org. Chem. 1998, 34, 428–433. This chemistry is depicted in scheme 3b.

The synthesis of substituted-3-hydroxy quinolinones (4a.3) has been reported in the literature, for example, Hradil et al. J. Heterocyclic Chem. 1999, 36, 141–144. This chemistry is depicted in scheme 4a.

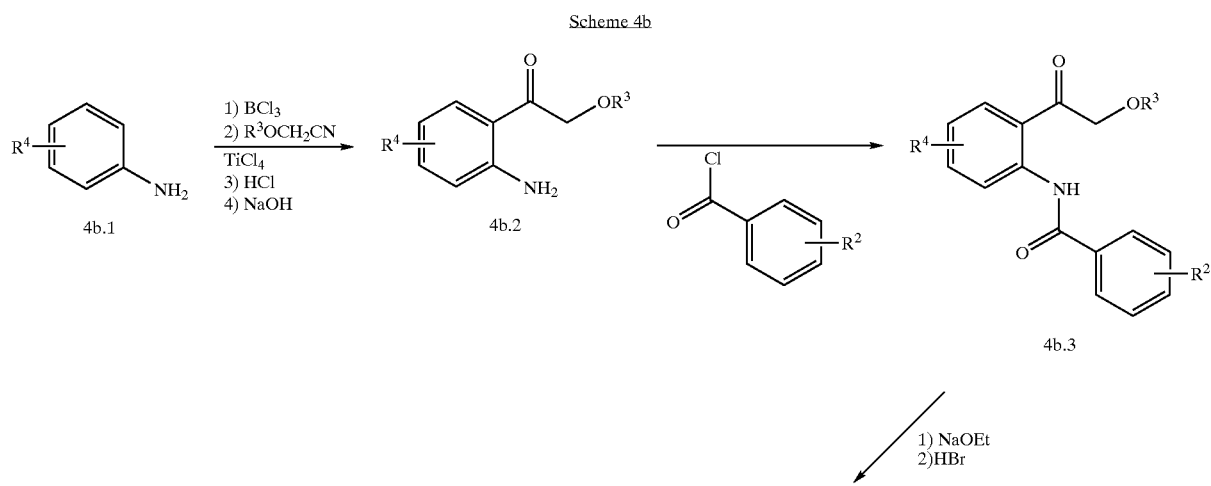

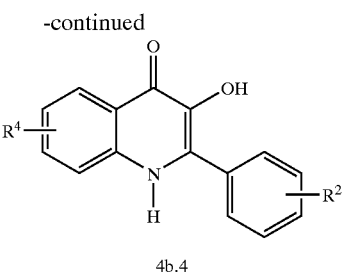

4b.4

An alternative synthesis of substituted-3-hydroxy quinolinones (4b.4) has been reported in the literature, for example, Sui et al. Eur. J. Chem. 1999, 34, 381–387. This chemistry is depicted in scheme 4b. A direct conversion of 4-quinolones into 3-hydroxy-4-quinolones has been reported in the liturature, for example, Behrman et al, J. Chem Research 1995, 164–165.

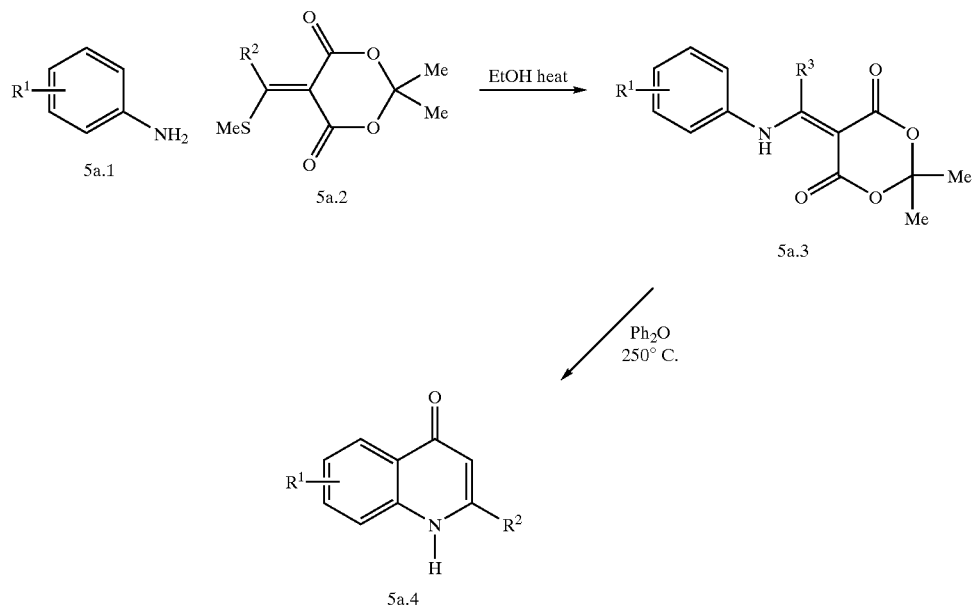

A versatile synthesis of quinolones was reported in the literature, by Chen et al, Synthesis, 1987, 482–483. The chemistry is shown in scheme 5a. Examples described herein such as Example 160 were prepared by a similar route.

Acids (2c.1) useful for this invention in their own right or for the preparation of beta ketoesters such as (2a.2) are either commercially available or readily prepared by a number of methods known to one skilled in the art of orgainic chemistry including, oxidation of an alcohol or hydrolysis of an ester. Transformations that produce acids from commercially available reagents are described by Larock, R. C. in "Comprehensive Organic Transformations: a Guide to Functional Group Preparations." 1989, VCH Publishers, N.Y., N.Y.

The compounds of the present invention may be modified by appending appropriate functionalities to enhance selective biological properties. Such modifications are known in the art and include those which increase biological penetration into a given biological compartment (e.g., blood, lymphatic system, central nervous system), increase oral availability, increase solubility to allow administration by injection, alter metabolism and alter rate of excretion.

Utility

The compounds of the present invention inhibit IMPDH enzyme, and are thus useful in the treatment, including prevention and therapy of disorders which are mediated or effected by cells which are sensitive to IMPDH inhibition, as described previously. The present invention thus provides methods for the treatment of IMPDH-associated disorders, comprising the step of administering to a subject in need thereof at least one compound of the formula I, preferably at least one compound represented by formulas II and/or III, in an amount effective therefor. Other therapeutic agents, such as those described below, may be employed with the inventive compounds in the present methods. In the methods of the present invention, such other therapeutic agent(s) may be administered prior to, simultaneously with or following the administration of the compound(s) of the present invention.

The compounds of the present invention can be used in treating a range of disorders exemplified by, but not limited to, disorders such as: the treatment of transplant rejection (e.g., kidney, liver, heart, lung, pancreas (e.g., islet cells), bone marrow, cornea, small bowel, skin allografts, skin homografts (such as employed in burn treatment), heart valve xenografts, serum sickness, and graft vs. host disease, in the treatment of autoimmune diseases, such as rheumatoid arthritis, psoriatic arthritis, multiple sclerosis, juvenile diabetes, asthma, inflammatory bowel disease (such as Crohn's disease and ulcerative colitus), pyoderma gangrenum, lupus (systemic lupus erythematosis), myasthenia gravis, psoriasis, dermatitis, dermatomyositis; eczema, seborrhoea, pulmonary inflammation, eye uveitis, hepatitis, Grave's disease, Hashimoto's thyroiditis, autoimmune thyroiditis, Behcet's or Sjorgen's syndrome (dry eyes/ mouth), pernicious or immunohaemolytic anaemia, Addison's disease (autoimmune disease of the adrenal glands), idiopathic adrenal insufficiency, autoimmune polyglandular disease (also known as autoimmune polyglandular syndrome), glomerulonephritis, scleroderma, morphea, lichen planus, viteligo (depigmentation of the skin), alopecia areata, autoimmune alopecia, autoimmune hypopituatarism, Guillain-Barre syndrome, and alveolitis; in the treatment of T-cell mediated hypersensitivity diseases, including contact hypersensitivity, delayed-type hypersensitivity, contact dermatitis (including that due to poison ivy), uticaria, skin allergies, respiratory allergies (hayfever, allergic rhinitis) and gluten-sensitive enteropathy (Celiac disease); in the treatment of inflammatory diseases such as osteoarthritis, acute pancreatitis, chronic pancreatitis, asthma, acute respiratory distress syndrome, Sezary's syndrome and vascular diseases which have an inflammatory and or a proliferatory component such as restenosis, stenosis and artherosclerosis; in the treatment of cancer and tumor disorders, such as solid tumors, lymphomas and leukemia; in the treatment of fungal infections such as mycosis fungoides; in protection from ischemic or reperfusion injury such as ischemic or reperfusion injury that may have been incurred during organ transplantation, myocardial infarction, stroke or other causes; and in the treatment of DNA and RNA viral replication diseases, such herpes simplex type 1 (HSV-1), herpes simplex type 2 (HSV-2), hepatitis (including hepatitis B and hepatitis C), cytomegalovirus, Epstein-Barr, and human immunodeficiency virus (HIV).

Additionally, IMPDH is also known to be present in bacteria and thus may regulate bacterial growth. As such, the IMPDH-inhibitor compounds of the present invention may be useful in treatment or prevention of bacterial infection, alone or in combination with other antibiotic agents.

In a particular embodiment, the compounds of the present invention are useful for the treatment of the aforementioned exemplary disorders irrespective of their etiology, for example, for the treatment of transplant rejection, rheumatoid arthritis, inflammatory bowel disease, and viral infections.

The present invention also provides pharmaceutical compositions comprising at least one of the compounds of formula I, preferably at least one of the compounds of formulas II and/or III, or a salt thereof, capable of treating an IMPDH-associated disorder in an amount effective therefor, alone or in combination with at least one additional therapeutic agent, and any pharmaceutically acceptable carrier, adjuvant or vehicle. "Additional therapeutic agents" encompasses, but is not limited to, an agent or agents selected from the group consisting of an immunosuppressant, an anti-cancer agent, an anti-viral agent, an anti-inflammatory agent, an anti-fungal agent, an antibiotic, or an anti-vascular hyperproliferation compound.

The term "pharmaceutically acceptable carrier, adjuvant or vehicle" refers to a carrier, adjuvant or vehicle that may be administered to a subject, together with a compound of the present invention, and which does not destroy the pharmacological activity thereof. Pharmaceutically acceptable carriers, adjuvants and vehicles that may be used in the pharmaceutical compositions of the present invention include, but are not limited to, the following: ion exchangers, alumina, aluminum stearate, lecithin, self-emulsifying drug delivery systems ("SEDDS") such as d(-tocopherol polyethyleneglycol 1000 succinate), surfactants used in pharmaceutical dosage forms such as Tweens or other similar polymeric delivery matrices, serum proteins such as human serum albumin, buffer substances such as phosphates, glycine, sorbic acid, potassium sorbate, partial glyceride mixtures of saturated vegetable fatty acids, water, salts or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as $\alpha$-, $\beta$- and $\gamma$-cyclodextrin, or chemically modified derivatives such as hydroxyalkylcyclodextrins, including 2- and 3-hydroxypropyl-$\beta$-cyclodextrins, or other solubilized derivatives may also be used to enhance delivery of the compounds of the present invention.

The compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The compounds of the formula I may be administered by any suitable means, for example, orally, such as in the form of tablets, capsules, granules or powders; sublingually; buccally; parenterally, such as by subcutaneous, intravenous, intramuscular, or intrasternal injection or infusion techniques (e.g., as sterile injectable aqueous or non-aqueous solutions or suspensions); nasally such as by inhalation spray; topically, such as in the form of a cream or ointment; or rectally such as in the form of suppositories; in dosage unit formulations containing non-toxic, pharmaceutically acceptable vehicles or diluents. The present compounds may, for example, be administered in a form suitable for immediate release or extended release. Immediate release or extended release may be achieved by the use of suitable pharmaceutical compositions comprising the present compounds, or, particularly in the case of extended release, by the use of devices such as subcutaneous implants or osmotic pumps. The present compounds may also be administered liposomally.

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The present compounds may also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel). or polyethylene glycols (PEG). Such formulations may also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g., Carbopol 934). Lubricants, glidants, flavors, coloring agents and stabilizers may also be added for ease of fabrication and use.

Exemplary compositions for nasal aerosol or inhalation administration include solutions in saline which may contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid. The term "parenteral" as used herein includes subcutaneous, intracutaneous, intravenous, intramuscular, intraarticular, intraarterial, intrasynovial, intrasternal, intrathecal, intralesional and intracranial injection or infusion techniques.

Exemplary compositions for rectal administration include suppositories which may contain, for example, a suitable non-irritating excipient, such as cocoa butter, synthetic glyceride esters or polyethylene glycols, which are solid at ordinary temperatures, but liquify and/or dissolve in the rectal cavity to release the drug.

Exemplary compositions for topical administration include a topical carrier such as Plastibase (mineral oil gelled with polyethylene).

The effective amount of a compound of the present invention may be determined by one of ordinary skill in the art, and includes exemplary dosage amounts for an adult human of from about 0.1 to 500 mg/kg of body weight of active compound per day, which may be administered in a single dose or in the form of individual divided doses, such as from 1 to 5 times per day. It will be understood that the specific dose level and frequency of dosage for any particular subject may be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats and the like, subject to IMPDH-associated disorders.

The compounds of the present invention may be employed alone or in combination with each other and/or other suitable therapeutic agents useful in the treatment of IMPDH-associated disorders, such as IMPDH inhibitors other than those of the present invention, immunosuppressants, anti-cancer agents, anti-viral agents, anti-inflammatory agents, anti-fungal agents, antibiotics, or anti-vascular hyperproliferation agents.

Exemplary such other therapeutic agents include the following: cyclosporins (e.g., cyclosporin A), CTLA4-Ig, antibodies such as anti-ICAM-3, anti-IL-2 receptor (Anti-Tac), anti-CD45RB, anti-CD2, anti-CD3 (OKT-3), anti-CD4, anti-CD80, anti-CD86, monoclonal antibody OKT3, agents blocking the interaction between CD40 and CD154 (a.k.a. "gp39"), such as antibodies specific for CD40 and/or CD154, fusion proteins constructed from CD40 and/or CD154/gp39 (e.g., CD4Ig and CD8gp39), inhibitors, such as nuclear translocation inhibitors, of NF-kappa B function, such as deoxyspergualin (DSG), non-steroidal antiinflammatory drugs (NSAIDs) such as ibuprofen, celecoxib and rofecoxib, steroids such as prednisone or dexamethasone, gold compounds, antiviral agents such as abacavir, antiproliferative agents such as methotrexate, leflunomide, FK506 (tacrolimus, Prograf), cytotoxic drugs such as azathiprine and cyclophosphamide, TNF-α inhibitors such as tenidap, anti-TNF antibodies or soluble TNF receptor, and rapamycin (sirolimus or Rapamune) or derivatives thereof.

The above other therapeutic agents, when employed in combination with the compounds of the present invention, may be used, for example, in those amounts indicated in the Physicians' Desk Reference (PDR) or as otherwise determined by one of ordinary skill in the art.

The compounds disclosed herein are capable of targeting and inhibiting IMPDH enzyme. Inhibition can be measured by various methods, including, for example, IMP dehydrogenase HPLC assays (measuring enzymatic production of XMP and NADH from IMP and NAD) and IMP dehydrogenase spectrophotometric assays (measuring enzymatic production of NADH from NAD). See, e.g., Montero et al., *Clinica Chimica Acta* 238:169–178 (1995). Additional assays known in the art can be used in ascertaining the degree of activity of a compound ("test compound") as an IMPDH inhibitor. The inventors used the following assay to determine the degree of activity of the compounds disclosed herein as IMPDH inhibitors:

Activity of IMPDH I and IMPDH II was measured following an adaptation of the method described in WO 97/40028. The reaction mixture was prepared containing 0.1M Tris pH 8.0, 0.1 M KCl, 3 mM EDTA, 2 mM DTT, 0.4 mM IMP and 40 nM enzyme (IMPDH I or IMPDH II). The reaction was started by the addition of NAD to a final concentration of 0.4 mM. The enzymatic reaction was followed by measuring the increase in absorbance at 340 nM that results from the formation of NADH. For the analysis of potential inhibitors of the enzyme, compounds were dissolved in DMSO to a final concentration of 10 mM and added to the assay mixture such that the final concentration of DMSO was 2.5%. The assay was carried out in a 96-well plate format, with a final reaction volume of 200 □1.

The compounds disclosed herein are capable of inhibiting the enzyme IMPDH at a measurable level, under the above-described assay or an assay which can determine an effect of inhibition of the enzyme IMPDH.

The following examples illustrate preferred embodiments of the present invention and do not limit the scope of the present invention which is defined in the claims. Abbreviations employed in the Examples are defined below. Compounds of the Examples are identified by the example and step in which they are prepared (e.g., "1A" denotes the title compound of step A of Example 1), or by the example only where the compound is the title compound of the example (for example, "2" denotes the title compound of Example 2).

| Abbreviations | |
|---|---|
| Ac | Acetyl |
| AcOH | Acetic acid |
| aq. | Aqueous |
| CDI | Carbonyldiimidazole |
| Bn | Benzyl |
| Boc | tert-butoxycarbonyl |
| DMAP | Dimethylaminopyridine |
| DMF | dimethylformamide |
| DMSO | Dimethylsulfoxide |
| EDC | 1-(3-Dimethylaminopropyl)-3-ethylcarbodiimide hydrochloride |
| EtOAc | Ethyl acetate |
| Et | Ethyl |
| EtOH | Ethanol |
| h | Hours |
| i | iso |
| HPLC | High pressure liquid chromatography |
| HOAc | Acetic acid |
| THF | Tetrahydrofuran |
| Lawesson's Reagent | [2,4-bis(4-methoxyphenyl)-1,3-dithia-2,4-diphosphetane-2-4-disufide |
| LC | liquid chromatography |
| Me | Methyl |
| MeOH | Methanol |
| min. | Minutes |
| M+ | $(M + H)^+$ |
| M+1 | $(M + H)^+$ |
| MS | Mass spectrometry |
| n | normal |
| Pd/C | Palladium on carbon |
| Ph | Phenyl |
| PPTS | Pyridinium p-toluenesulfonate |
| Pr | Propyl |
| p-TsOH | para-Toluenesulonic acid |
| Ret Time | Retention time |
| rt or RT | Room temperature |
| sat. | Saturated |
| TFA | Trifluoroacetic acid |
| THF | Tetrahydrofuran |
| TOSMIC | Tosylmethyl isocyanide |
| YMC | YMC Inc, Wilmington, NC 28403 |

EXAMPLE 1

7-Methoxy-6-(5-oxazolyl)-2-phenyl-4(1H)-quinolinone

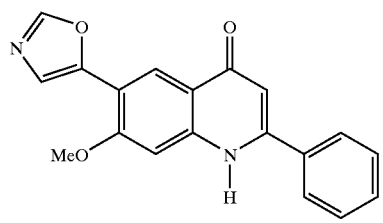

Example 1 Part A

4-Nitro-2-methoxy-(α,α bisacetoxy)toluene

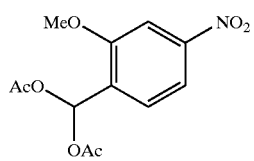

1A

To a 5 L three necked round bottom flask equipped with a mechanical stirrer was added 4-nitro-2-methoxytoluene (150.0 g, 0.8973 mol), HOAc (900 mL) and Ac$_2$O (900 mL). The mixture was stirred and cooled to 8° C. with an acetone/ice bath. Concentrated H$_2$SO$_4$ (136 mL) was carefully added while keeping the reaction temperature below 19° C. After cooling to 0° C., CrO$_3$ (252.6 g, 2.526 mol, 2.815 equiv.) was added portion-wise over 1 hour while maintaining the reaction temperature between 0–10° C. After the addition, the mixture was stirred at 0° C. for 30 minutes at which time the reaction was complete. The reaction mixture was then carefully poured into ice (1.5 kg) with stirring to give a slurry. The remaining black gummy residue was rinsed with HOAc (3×100 mL), and the washes were added to the slurry. After stirring for 10 minutes, the slurry was filtered. The cake was washed with water (3×400 mL) and suction dried for 17 hours to 1A (129.0 g, 51%). $^1$H NMR (CDCl$_3$) ☐ 8.02 (s, 1H), 7.89 (d, J=8.4 Hz, 1H), 7.77 (s, 1H), (d, 8.4 Hz, 1H), 3.98 (s, 3H), 2.16 (s, 6H).

Example 1, Part B

4-Nitro-2-methoxybenzaldehyde

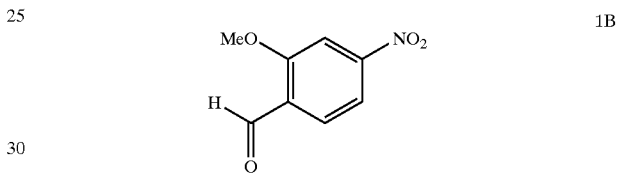

To a 2 L rounded bottom flask equipped with a condenser and a mechanical stirrer was placed 1A (250.7 g, 0.8851 mol), dioxane (300 mL) and concentrated HCl (60 mL). The reaction mixture was heated to reflux and stirred under N$_2$ for 20 hours. Water (250 mL) was added dropwise while maintaining the reaction mixture at reflux. After cooling to 0° C. with an ice/water bath, the resulting slurry was stirred for 30 minutes and then filtered. The cake was washed with water (4×200 mL) and suction dried for 17 hours to give 1B (146.3 g, 91%) as a yellow solid. $^1$H NMR (CDCl$_3$) ☐ 10.54 (s, 1H), 8.00 (d, J=8.3 Hz, 1H), 7.91 (s, 1H), 7.89 (d, J=8.3 Hz, 1H), 4.08 (s, 3H).

Example 1 Part C 5-(4-Nitro-2-methoxyphenyl)oxazole

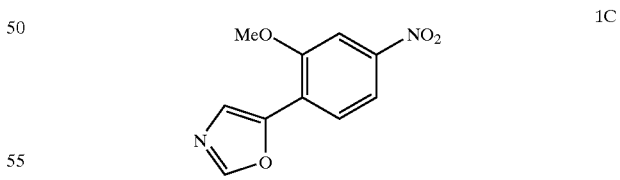

To a 5 L three necked round bottom flask equipped with a condenser and a mechanical stirrer was placed 1B (146.3 g, 0.8076 mol), TOSMIC (157.7 g, 0.8077 mol), K$_2$CO3 (116.6 g, 0.8075 mol) and MeOH (2.5 L). The mixture was heated to reflux under N$_2$ and stirred for 3 hours. Water (1.25 L) was added drop-wise while maintaining the pot temperature between 59–69° C. The resulting slurry was cooled to room temperature, and then to 5° C. with an ice-water bath. After stirring for 30 minutes at 5° C., the slurry was filtered. The resulting cake was washed with water (3×400 mL) and dried in a vacuum oven at 45° C. for 20 hours to 1C (148.5 g, 84%) as a yellow-reddish solid. ¹H NMR (CDCl₃) □ 8.02 (s, 1H), 7.97 (d, J=2 Hz, 1H), 7.95 (d, J 2 Hz, 1H), 7.86 (s, 1H), 7.78 (s, 1H), 4.11 (s, 3H).

Example 1, Part D 5-(4-Amino-2-methoxyphenyl)oxazole

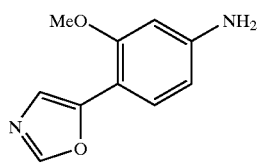

1D

In a 2 L hydrogenation flask was placed 1C (130.0 g, 0.6131mol), Pd/C (10%, 26.2 g) and absolute EtOH (1280 mL). The mixture was hydrogenated at 35–45psi H₂ until the reaction was complete. The mixture was filtered over a pad of celite (20 g) and the cake was washed with EtOH (3×100 mL). The filtrate was concentrated to a volume of 350 mL. Heptane (500 mL) was added to the resulting slurry. After stirring for 2 hours at room temperature, the slurry was filtered. The cake was washed with heptane (3×100 mL) and air-dried to give ID (80.0 g). A second portion of product (30.2 g) was recovered from the mother liquor affording a total yield of 95%. ¹H NMR (CDCl₃) □ 7.88 (s, 1H), 7.60 (d, J=8.4 Hz, 1H), 7.41 (s, 1H), 6.41 (dd, J=8.4,. 2.1 Hz, 1H), 3.34 (d, J=2.1 Hz, 1H), 3.98 (bs, 2H), 3.94 (s, 3H).

Example 1, Part E

3-[3-methoxy-4-(5-oxazolyl)phenyl]amino]-3-phenyl-2-propenoic acid Ethyl ester

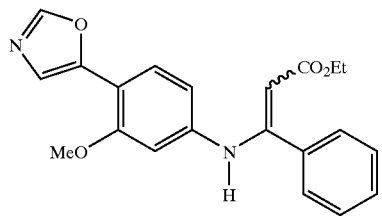

1E

A mixture of 3-methoxy-4-(5-oxazolyl)aniline, 1D, (1.00 g; 5.26 mmol), ethyl benzoylacetate (0.91 mL; 5.26 mmol), and p-toluenesulfonic acid (0.10 g; 0.526 mmol) in 55 mL of dry toluene was heated at reflux in a Dean-Stark apparatus overnight. During this time a precipitate formed. The reaction mixture was cooled to room temperature and filtered to give 1F and small amount of p-toluenesulfonic acid. The filtrate was concentrated under reduced pressure, diluted with dichloromethane, and washed with water. The organic layer was collected and dried over anhydrous sodium sulfate. The solvent was removed under reduced pressure, and the residue was purified by silica chromatography to provide 0.487 g of 1E as a pale yellow semi-solid. Analytical HPLC retention time=4.08 min. (Column: YMC S5 ODS 4.6×50 mm Ballistic; Solvent A=10% MeOH, 90% H₂O, 0.2% H₃PO₄; Solvent B=90% MeOH, 10% H₂O, 0.2% H₃PO₄) with a LC/MS M⁺¹=365.23.

Example 1, Part F

7-Methoxy-6-(5-oxazolyl)-2-phenyl-4(1H)-quinolinone 1E was heated in 4 mL of xylene in a sealed tube at 250° C. overnight. During this time, a precipitate was formed. The reaction mixture was cooled to room temperature, and the precipitate was collected by vacuum filtration, washed with dichloromethane, and dried thoroughly to give 281 mg of 1F as a white solid. The filtrate contained additional amounts of the product and starting material 1E. The product was 99% pure by nalytical HPLC with a retention time=2.71 min. (Column: YMC S5 ODS 4.6×50 mm Ballistic; Solvent A=10% MeOH, 90% H₂O, 0.2% H₃PO₄; Solvent B=90% MeOH, 10% H₂O, 0.2% H₃PO₄) and a LC/MS M⁺¹=319.14. ¹H-NMR (400 mHz, DMSO) □ 4.05 (s, 3H), 6.34 (s, 1H), 7.38 (s, 1H), 7.59–7.61 (m, 4H), 7.84–7.85 (m, 2H), 8.40 (s, 1H), 8.50 (s, 1H), and 11.72 (s, 1H).

Example 2

2-(3-Bromophenyl)-7-methoxy-6-(5-oxazolyl)-4(1H)-quinolinone

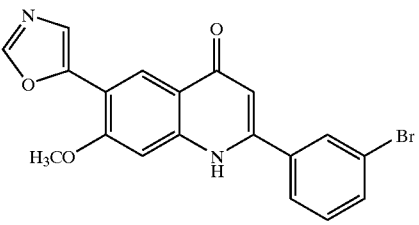

2

Example 2 Part A 3-(3-Bromophenyl)-3-oxopropanoic acid ethyl ester

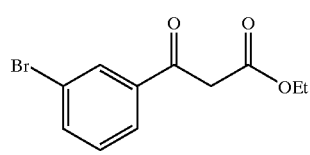

2A

To potassium ethyl malonate (3.25 g, 19.13 mmol) in acetonitrile (50 mL) was sequentially added triethyl amine (4.1 mL, 29.16 mmol) and magnesium chloride (2.16 g, 22.78 mmol) at room temperature. After stirring the reaction mixture at room temperature for 2 hours, 3-bromobenzoyl chloride (2.0 g, 9.11 mmol) was added and the mixture was heated at 60° C. for 18 hours, concentrated under reduced pressure and partitioned between ethyl acetate (100 mL) and 1N HCl (25 mL). The ethyl acetate layer was dried over sodium sulfate and concentrated under reduced pressure to yield the title compound (2.45 g, 99 %). ¹H NMR (CDCl₃): δ 8.1 (s, 1H), 7.85 (d, 1H), 7.7 (d, 1H), 7.35 (t, 1H), 4.3 (m, 2H), 3.4 (s, 1H), 1.3 (m, 3H).

Example 2 Part B 3-(3-Bromophenyl)-3-(methylamino)-2-propenoic acid ethyl ester

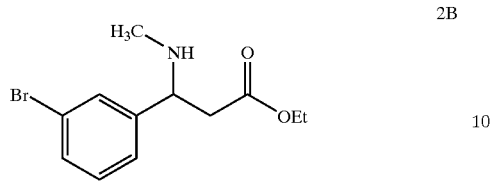

2B

To a solution of 2A (2.5 g, 9.22 mmol) in ethyl alcohol (15 mL) was added methyl amine (2.0M in methyl alcohol, 23 mL, 46.12 mmol) and acetic acid (2.63 mL, 46.12 mmol). The reaction mixture was heated under reflux for three hours, cooled to room temperature and partitioned between ethyl acetate (50 mL) and water (100 mL). The ethyl acetate layer was dried over sodium sulfate and concentrated under reduced pressure to yield the title compound (2.45 g, 93%) as an oil. $^1$H NMR (CDCl$_3$): δ 8.4 (brs, 1H), 7.4 (m, 2H), 7.2 (m, 2H), 4.6 (s, 1H), 4.2 (q, 2H), 2.8 (d, 3H), 1.2 (t, 3H).

Example 2, Part C

3-[3-methoxy-4-(5-oxazolyl)phenyl]amino]-3-phenyl-2-propenoic acid ethyl ester

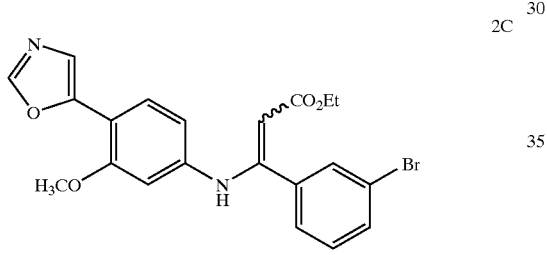

2C

To a solution of 2B (2.45 g, 8.68 mmol) in dichloromethane (50 mL) was added aniline 1D (1.5 g, 7.89 mmol) and pyridinium para-toluenesulfonate (2.2 g, 8.68 mmol). The reaction mixture was heated under reflux for 24 hours and stirred at room temperature for 40 hours. The solid that separates out was filtered and washed with dichloromethane (20 mL). The filtrate was concentrated under reduced pressure and purified by flash column chromatography employing hexane-ethyl acetate (6:4) as the eluent, to yield the title compound as a syrup (3.0 g, 85.7%). $^1$H NMR (CDCl$_3$): δ 10.3 (s, 1H), 7.8 (s, 1H), 7.6 (s, 1H), 7.5 (m, 2H), 7.4 (s, 1H), 7.25 (1H), 7.2 (m, 1H), 6.3 (d, 1H), 6.2 (s, 1H), 5.1 (s, 1H), 4.3 (q, 2H), 3.65 (s, 3H), 1.2 (t, 3H).

Example 2, Part D 2-(3-Bromophenyl)-7-methoxy-6-(5-oxazolyl)-4(1H)-quinolinone A solution of 2C (3.0 g, 6.77 mmol) in ortho-xylene (25 mL) was heated to 240° C. in a sealed tube for three hours. The reaction mixture was cooled to room temperature and the solid that separates out was filtered, washed with ethyl acetate (60 mL) and dried to yield the title compound as a solid (2.1 g, 78.1%). $^1$H NMR (DMSO): δ 8.6 (s, 1H)<8.5 (s, 1H), 8.1 (s, 1H), 7.9 (d, 1H), 7.8 (d, 1H), 7.6 (s, 1H), 7.5 (t, 1H), 7.4 (m,1H), 6.6 (s, 1H) 4.1 (s, 3H). LC/MS (retention time=3.11 min.; M$^+$398. Column: YMC ODSA S5 C18 4.6×50 mm (4 min. gradient. Solvent A=10% MeOH, 90% H$_2$O, 0.1% TFA; Solvent B=90% MeOH, 10% H$_2$O, 0.1% TFA).

Example 3

7-Methoxy-2-[3-(1-pyrrolidinyl)phenyl]-6-(5-oxazolyl)-4(1H)-quinolinone

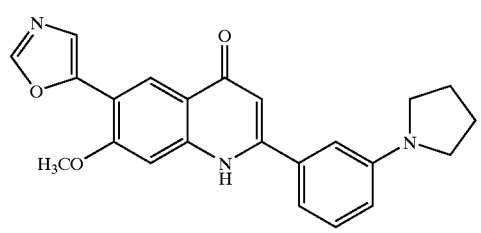

3

Example 3 Part A 2-(3-Bromophenyl)-7-methoxy-4-methoxymethoxy-6-(5-oxazolyl)quinoline

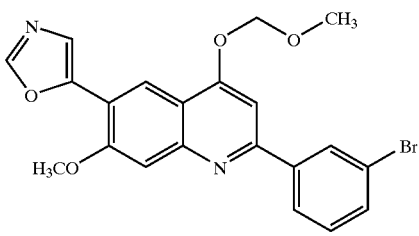

3A

Quinolone 2 (0.3 g, 0.75 mmol) in dimethylformamide (10 mL) was cooled to 0° C. and sodium hydride (0.023 g, 0.90 mmol) was added over a three minute period. The reaction mixture was stirred at 0° C. for twenty minutes and heated at 80° C. for twenty minutes. The mixture was bought to room temperature and chloromethyl methyl ether (68 μL, 0.90 mmol) was added over three minutes. The reaction mixture was heated at 80° C. for ten minutes and concentrated under reduced pressure. To the residue that was obtained, water (20 mL) was cautiously added and the solid that separates out was filtered and dried (0.33 g, 100%). LC/MS (retention time=3.03 min.; M$^+$441.21. Column: YMC ODSA S5 C18 4.6×50 mm (4 min. gradient. Solvent A=10% MeOH, 90% H$_2$O, 0.1% TFA; Solvent B=90% MeOH, 10% H$_2$O, 0.1% TFA).

Example 3 Part B

2-[3-(1-pyrrolidinyl)phenyl]-7-methoxy-4-methoxymethoxy-6-(5-oxazolyl)quinoline

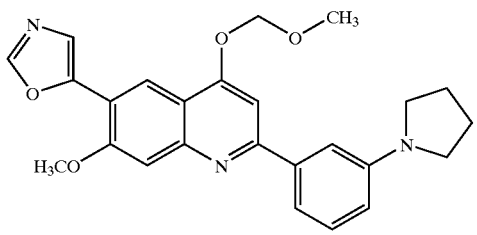
3B

To a solution of 3A (0.125 g, 0.28 mmol) in toluene (2 mL) was sequentially added tris(dibenzylideneacetone)dipalladium(0) (1 mg), S(–)BINAP (2 mg), cesium carbonate (0.129 g, 0.396 mmol) and pyrrolidine (71 μL, 0.85 mmol). The reaction mixture was heated at 100° C. for eighteen hours, cooled to room temperature, filtered over celite and the celite pad was washed with ethyl acetate (30 mL). The filtrate was concentrated under reduced pressure and purified by flash column chromatography using hexane-ethyl acetate (2:3) as the eluent to yield the title compound as an oil (0.04 g, 36.5%). $^1$H NMR (CDCl$_3$) : δ 8.6 (s, 1H), 8.0 (s, 1H), 7.7 (s, 1H), 7.5 (s, 1H), 7.2–7.4 (m, 4H), 6.8 (d, 1H), 5.5 (s, 2H), 4.1 (s, 3H), 3.6 (s, 3H), 3.4 (m, 4H), 2.1 (m, 4H).

Example 3 Part C

7-Methoxy-2-[3-(1-pyrrolidinyl)phenyl]-6-(5-oxazolyl)-4(1H)-quinolinone

To a solution of 3B (0.04 g, 0.1 mmol) in dichloromethane (1 mL) was added five drops of 4N HCl in dioxane. The reaction mixture was heated at 45° C. for thirty minutes, concentrated under reduced pressure and kept on the high vacuum pump for thirty minutes to yield the title compound as a solid (0.038 g). $^1$H NMR (CDCl$_3$): δ 8.6 (s, 1H), 8.5 (s, 1H), 8.1 (s, 1H), 7.8 (s, 1H), 7.5 (t, 2H), 7.3 (s, 1H), 7.1 (m, 2H), 6.8 (d, 2H), 4.1 (s, 3H), 3.4 (m, 4H), 2.0 (m, 4H). LC/MS (retention time=3.56 min.; M$^+$388.15. Column: YMC ODS-A S5 C18 4.6×50 mm (4 min. gradient. Solvent A=10% MeOH, 90% H$_2$O, 0.1% TFA; Solvent B=90% MeOH, 10% H$_2$O, 0.1% TFA).

Example 4

7-Methoxy-2-(4-methylphenyl)-6-(5-oxazolyl)-4(1H)-quinolinone

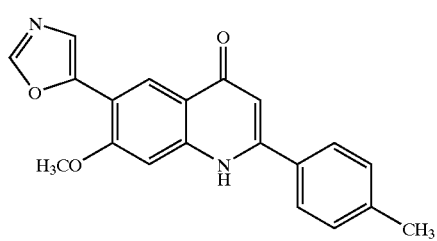
4

Example 4, Part A 5-(4-Amino-5-iodo-2-methoxyphenyl)oxazole

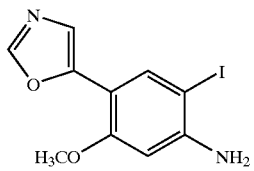
4A

To a solution of 1D (1.0 g, 5.26 mmol) in CH$_2$Cl$_2$ in a round bottom flask was placed in an ice water bath. Pyridine (0.44 ml, 5.44 mmol), iodine (1.38 g, 5.42 mmol) and AgSO$_3$CF$_3$ (1.39 g, 5.43 mmol) were added to the reaction mixture, which was stirred overnight at room temperature. The solid was removed with filtration and the solution was washed with two 30 ml potions of water, 30 ml of NaHSO$_3$, 30 ml of water, 30 ml of Brine, dried over Na$_2$SO$_4$. Filtration and removal of solvent afforded the title compound (1.20 g, 72%) . NMR (CD$_3$OD): □ 8.16 (1H, s), 7. 94 (1H, s), 7.32 (1H, 2), 6.60 (1H, s), 3.95 (3H, s); HPLC: 98%; LC-MS: m/z 317.04 (M+H)$^+$

Example 4, Part A

7-Methoxy-2-(4-methylphenyl)-6-(5-oxazolyl)-4(1H)-quinolinone

A small stainless steel bomb was charged with 4A, (100 mg, 0.3mmmol) dissolved in 2.5 ml of diethylamine. Hereto was added p-methyl-phenylacetylene (81.7 μL,0.6 mmol) and PdCl$_2$(PPh$_3$)$_2$ (19 mg, 5%). The stainless steel bomb was sealed and charged with carbon monoxide. The reaction was stirred for 4 hours at 119° C. with an internal pressure of ~ 40 psi. The reaction was cooled to room temperature and the reaction mixture transferred to a round bottom flask by dissolving it in methylene chloride. The mixture was evaporated in vacuo and the residue washed with warm methanol, and filtered. The filtrate was passed through a cation exchange plug, and the solvent was removed in vacuo to afford 25.4 mg of the desired product MW 332.36, yield 25.4%. The HPLC retention Time was 2.957 min (YMC S5 ODS 4.6×50 mm Ballistic; Solvent A=10% MeOH, 90% H$_2$O, 0.2% H$_3$PO$_4$; Solvent B=90% MeOH, 10% H$_2$O, 0.2% H$_3$PO$_4$) with a LC/MS [M+H]$^+$=333.

Example 5

3-[1,4-Dihydro-7-methoxy-6-(5-oxazaolyl)-4-oxo-2-quinolinyl]benzeneacetic acid

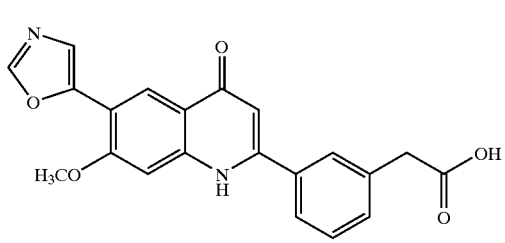
5

Example 5, Part A

3-Bromophenylacetic acid methyl ester

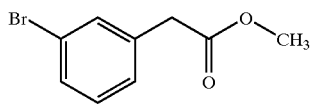

To a solution of 3-bromophenylacetic acid (1.0 g, 4.65 mmol), 1,3-dicyclohexylcarbodiimide (1.44 g, 6.98 mmol) and MeOH (149 mg, 4.65 mmol) in dichloromethane (40 ml) was added 4-dimethylaminopyridine (57 mg, 0.465 mmol). The reaction mixture was stirred at RT for 1 hr. The white solid was precipitated out which was removed with filtration. The reaction solution was concentrated to give a crude product which was purified on silica gel column with dichloromethane. The product was collected which contain a little amount of DCU (1.36 g). NMR (CDCl$_3$): ☐ 7.20–7.46 (4H, m), 3.72 (3H, s), 3.621(2H, s).

Example 5, Part B 3-(Trimethylsilylethynly)phenylacetic acid methyl ester

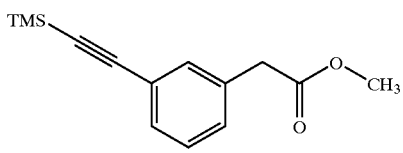

A mixture of 5A (1.36 g, 5.52 mmol), (trimethylsilyl) acetylene (0.90 g, 9.15 mmol), bis(triphenylphosphine) palladium(II) acetate (0.40 g, 0.539 mmol) and triethylamine (20 ml) in toluene (20 ml) was heated to 90–100° C. for 2 hrs. The catalyst was removed with filtration. The reaction mixture was concentrated to give a crude product which was dissolved in 150 ml of EtOAc. It was washed with 50 ml of NaHCO$_3$, 50 ml of brine, dried over Na$_2$SO$_4$. Filtration and removal of solvent afforded a crude product which was purified by flash chromatography (silica, Hexane/ CH$_2$Cl$_2$ 20/1) to give the title compound (0.88 g, 65%). NMR (CDCl$_3$): ☐ 6.96–7.22 (4H, m), 3.47 (3H, d, J=5.5Hz), 3.37 (2H, d, J=2.9Hz).

Example 5, Part C

3-Ethynlyphenylacetic acid

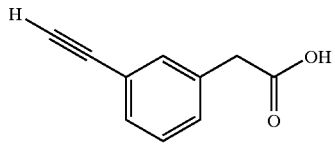

A solution of 5B (0.88 g, 3.84 mmol) in THF (40 ML) was treated with Bu4NF (4.5 mL 1M in THF) at ice water bath. The reaction mixture was warmed up to RT and stirred for 20 minutes which was concentrated to yield a crude product. It was dissolved in 150 ml of ethyl acetate was washed with 50 ml of water, 50 ml of brine, dried over K$_2$CO$_s$. Filtration and removal of solvent afforded a crude product which was dissolved in MeOH (40 ml) and water (15 mL). To this solution was added LiOH*H$_2$O (200 mg, 4.76 mmol) and stirred at RT for 1 hr. Filtration and removal of solvent afforded a crude product which was added water (50 ml). It was acidified with 1N HCl solution until PH<3. The water phase was extracted with three 50 ml portions of dichloromethane. The combined organic phase was washed with water (50 ml), brine (50 ml) and then dried over MgSO$_4$. Filtration and removal of solvent afforded a crude product which was purified by flash chromatography (silica, CH$_2$Cl$_2$/MeOH 20/1) to give the title compound (0.474 g, 77%). NMR (CDCl$_3$): ☐ 7.08–7.34 (4H, m), 3.52 (1H, s), 3.51 (2H, d).

Example 5, Part D

3-[1,4-Dihydro-7-methoxy-6-(5-oxazaolyl)-4-oxo-2-quinolinyl]benzeneacetic acid

A mixture of above 5C (96 mg, 0.6 mmol), 4A (100 mg, 0.3 mmol), diethylamine (2.5 ml) and bis(triphenylphosphine)palladium(II) chloride (13 mg, 0.019 mmol) in a stainless steel pressure reaction vessel was assembled and hooked up to a carbon monoxide tank. It was charged CO about 40 psi and heated to 120° C. for 20 minutes. The reaction mixture was added MeOH (20 ml). Filtration and removal of solvent afforded a crude product which was purified by flash prep-TLC plate (silica, 25% methanol in CH$_2$Cl$_2$) to give the title compound (36 mg, 32%). NMR (CD$_3$OD): ☐ 8.67 (1H, s), 8.34 (1H, s), 7.76 (1H, 2), 7.58–7.66 (2H, m), 7.44–7.55 (2H, m), 7.33 (1H, s), 6.57 (1H, s), 4.15 (3H, s), 3.61 (2H, s); HPLC:. 96.9%; LC-MS: m/z 377.12 (M+H)$^+$.

EXAMPLE 6

3-[1,4-Dihydro-7-methoxy-6-(5-oxazaolyl)-4-oxo-2-quinolinyl]benzoic acid methyl ester

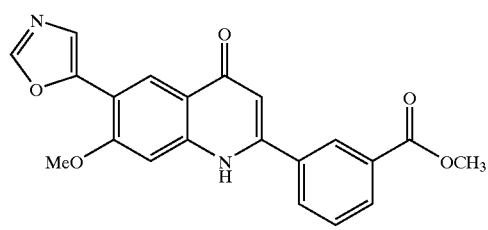

Example 6 Part A 3-(3-methoxycarbonylphenyl)-3-oxopropanoic acid ethyl ester

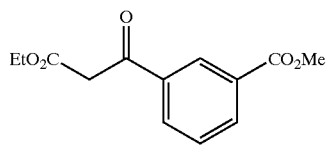

Monomethyl isophathalate (2.0 g, 11.1 mmol) was dissolved in a 1:3 mixture of tetrahydrofuran and dichloromethane. Carbonyldiimidazole (1.89 g, 11.7 mmol) was added slowly. The mixture was then stirred under nitrogen for 1 hr at room temperature. In a separate flask, ethyl malonate, potassium salt (3.96 g, 23.3 mmol) was dissolved in acetonitrile and magnesium chloride (2.64 g, 27.8 mmol) and triethylamine (4.95 ml, 35.5 mmol) was added to result in a heterogeneous suspension, which was stirred at room temperature for 1 h. The two reaction mixtures were mixed, and the resulting suspension was stirred @80° C. for 8 hours. 100 ml of a 2N aqueous HCl solution was added to the reaction mixture, which was subsequently extracted with dichloromethane. The organic layer was washed with 2N HCl twice and twice with water, dried ($MgSO_4$) and evaporated in vacuo to afford 4.0 g of an oil. Purification on silica gel using Biotage® eluting with 20% EtOAc in Hexanes, recovered 1.5 g of 6A as a clear oil. LC/MS: Retention Time=1.38 min (YMC S5 Turbopack 4.6×33mm, 2 min gradient; Solvent A=10% MeOH, 90% $H_2O$, 0.1% TFA; Solvent B=90% MeOH, 10% $H_2O$, 0.1% TFA) with a $(M+H)^+$=251.13. $^1$H-NMR (Joel 500 Hz/ $CDCl_3$) (1:2 mixture of enol and keto form) Keto: δ 1.17–1.21 (t, 3H, J=8.8 Hz), 3.89 (s, 3H), 3.96 (s, 2H), 4.12–4.18 (q, 2H, J=8.8 Hz) 5.67(s, 1H); 7.50–7.54 (t, 1H, J=9.3 Hz), 8.07–8.09 (d, 1H, J=9.9 Hz), 8.19–8.21 (d, 1H, J=9.9 Hz), 8.5 (d, 1H, J=2.2 Hz)

Example 6 Part B 3-(3-Methoxycarbonylphenyl)-3-(methylamino)-2-propenoic acid ethyl ester

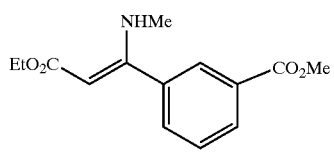

6B

A mixture of 6A (0.730 g, 2.92 mmol), methylamine (7.29 mL, 14.6 mmol of a 2.0 M solution in methanol), and acetic acid (0.84 mL, 14.6 mmol) in 14 mL of ethanol was heated a approximately 80° overnight. The solvent was removed under reduced pressure, and the residue was dissolved in dichloromethane and washed three times with a saturated aqueous brine solution. The organic layer was dried over anhydrous sodium sulfate and concentrated to give 0.766 g (99%) of 6B. $^1$H-NMR (400 mHz, $CDCl_3$) □ 1.26–1.30 (m, 3H), 2.75–2.77 (m, 2H), 3.94 (s, 3H), 4.12–4.18 (m, 2H), 4.60 (s, 1H), 7.49 (t, 1H, J=7.6 Hz), 7.55 (d, 1H, J=7.6 Hz), 8.04 (s, 1H), 8.08 (d, 1H, J=7.6 Hz), and 8.48 (brs, 1H).

Example 6, Part C

3-[3-Methoxy-4-(5-oxazolyl)phenyl]amino]-3-(3-methoxycarbonylphenyl)-2-propenoic acid ethyl ester

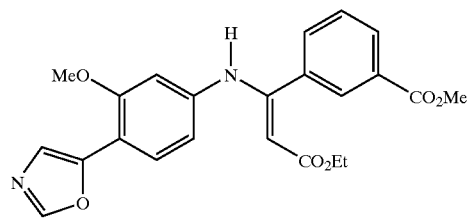

6C

A mixture of the 1D (0.496 g, 2.61 mmol), 6B (0.756 g, 2.87 mmol), and pyridinium p-toluenesulfonate (0.722 g, 2.87 mmol) in 22 mL of dry dichloromethane was heated at reflux overnight. The reaction mixture was filtered, and the filtrate was concentrated under reduced pressure and purified by silica gel chromatography to give 0.783 g (71%) of the 6C as a pale yellow semi-solid. The product had an analytical HPLC retention time 3.92 min. (Column: YMC S5 ODS 4.6×50 mm Ballistic; Solvent A=10% MeOH, 90% $H_2O$, 0.2% $H_3PO_4$; Solvent B=90% MeOH, 10% $H_2O$, 0.2% $H_3PO_4$) and a LC/MS $(M+1)^+$=423.26.

Example 6, Part D

3-[1,4-Dihydro-7-methoxy-6-(5-oxazaolyl)-4-oxo-2-quinolinyl]benzoic acid methyl ester A solution of 6C (0.783 g, 1.85 mmol) in approximately 10 mL of xylene was divided between two sealed tubes. The reaction mixtures were heated at 250° C. overnight. The resulting precipitate was collected via vacuum filtration to give 0.334 g (48%) of the 6 as a white solid. The filtrate was concentrated to provide recovered 6Calong with some additional quinolone 6. The product was 100% pure by analytical HPLC with a retention time=2.92 min. (Column: YMC S5 ODS 4.6×50 mm Ballistic; Solvent A=10% MeOH, 90% $H_2O$, 0.2% $H_3PO_4$; Solvent B=90% MeOH, 10% $H_2O$, 0.2% $H_3PO_4$) and a LC/MS $M^{+1}$=377.28. $^1$H-NMR (400 mHz, DMSO) □ 3.93 (s, 3H), 4.06 (s, 3H), 6.37 (s, 1H), 7.39 (s, 1H), 7.61 (s, 1H), 7.73–7.77 (m, 1H), 8.12–8.16 (m, 2H), 8.41 (s, 2H), 8.49 (s, 1H), and 11.85 (s, 1H).

EXAMPLE 7

2-[3-(Hydroxymethyl)phenyl]-7-methoxy-6-(5-oxazaolyl)-4(1H)-quinolinone

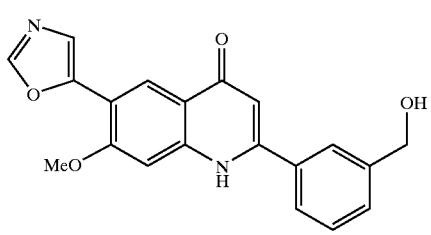

7

To 6 (0.100 g, 0.266 mmol) in 20 mL of anhydrous tetrahydrofuran and 20 mL of 1,4-dioxane was added lithium aluminum hydride (0.80 mL of a 1.0 M solution in tetrahydrofuran, 0.798 mmol) at room temperature. The reaction mixture was stirred for 1 h. To the mixture was added water (31.0 □L), followed by 15% aqueous sodium hydroxide (31.0 □L), and finally, additional water (93.0 □L). The mixture was stirred for 1 h. The solvent was removed under reduced pressure, and the residue was purified by silica gel chromatography to give 85 mg (91%) of the product as an off-white solid. The product was 100% pure by analytical HPLC with a retention time=2.52 min. (Column: YMC S5 ODS 4.6×50 mm Ballistic; Solvent A=10% MeOH, 90% $H_2O$, 0.2% $H_3PO_4$; Solvent B=90% MeOH, 10% $H_2O$, 0.2% $H_3PO_4$) and a LC/MS $M^{+1}$=349.16.

EXAMPLE 8

2-[3-(1-Hydroxy-1-methylethyl)phenyl]-7-methoxy-6-(5-oxazaolyl)-4(1H)-quinolinone

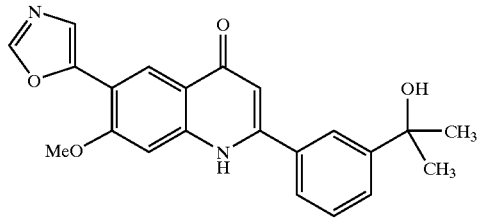

8

To 6 (0.015 g, 0.040 mmol) in 14 mL of anhydrous tetrahydrofuran at room temperature was added methyl magnesium bromide (80.0 mL of a 3.0 M solution in tetrahydrofuran, 0.239 mmol). The reaction mixture was stirred for 30 min. and then quenched with a small amount of a saturated aqueous solution of ammonium chloride. The mixture was filtered, and the solvent was removed under reduced pressure. The resulting crude product was purified by preparative HPLC to afford 6.0 mg of the product as a off-white solid. The product was 96% pure by analytical HPLC with a retention time=2.77 min. (Column: YMC S5 ODS 4.6×50 mm Ballistic; Solvent A=10% MeOH, 90% $H_2O$, 0.2% $H_3PO_4$; Solvent B=90% MeOH, 10% $H_2O$, 0.2% $H_3PO_4$) and a LC/MS $M^{+1}$=377.22.

Example 9

7-Methoxy-2-[3-(4-methyl-1-piperazinyl)phenyl]-6-(5-oxazaolyl)-4(1H)-quinolinone

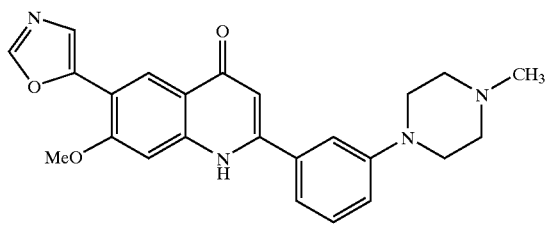

9

Example 9, Part A

2-[3-(4-methyl-1-piperazinyl)phenyl]-7-methoxy-4-methoxymethoxy-6-(5-oxazolyl)quinoline

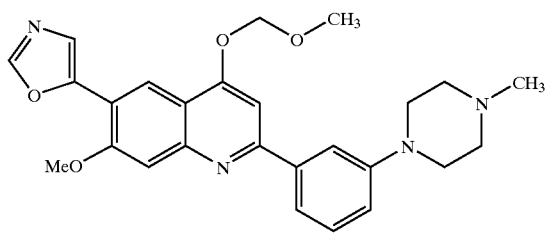

9A 9A was prepared from 3A by a route analogous to that used for the preparation of 3B, except in the purification step: the reaction mixture was concentrated in vacuo and carried to the next step without further purification.

Example 9, Part B

7-Methoxy-2-[3-(4-methyl-1-piperazinyl)phenyl]-6-(5-oxazaolyl)-4(1H)-quinolinone To a solution of crude 9A (43 mg, 0.098 mmol) in dichloromethane (0.4 mL) was added 1 mL TFA dropwise and stirred at room temperature for 30 minutes. The reaction mixture was then concentrated in vacuo and subject to preparative HPLC (Preparative HPLC Conditions: YMC S5 ODS 20×100 mm column, start % B=0, final % B=100, gradient time=10 min, wavelength=254, solvent A=10% MeOH, 90% $H_2O$, 0.1% TFA, solvent B=90% MeOH, 10% $H_2O$, 0.1% TFA). to give 12 mg of 9 as yellow solid (TFA salt). LC/MS (retention time=2.393 min.; $M^+$417. Column: YMC ODS-A S5 C18 4.6×50 mm (4 min. gradient. Solvent A=10% MeOH, 90% $H_2$, 0.1% TFA; Solvent B=90% MeOH, 10% $H_2O$, 0.1% TFA).

Example 10

2-[2,3-Dihydro-3-(dimethylamino)-1H-inden-5-yl]-7-methoxy-6-(5-oxazolyl)-4(1H)-quinolinone

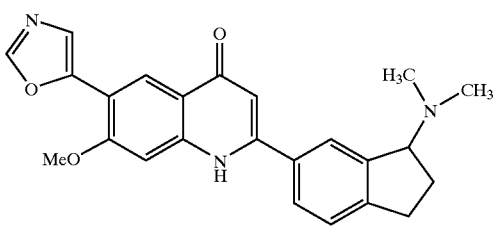

10

Example 10 Part A

6-Bromo-2,3-dihydro-1H-inden-1-ol

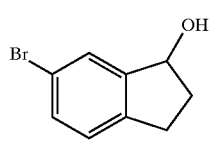

10A

To a solution of 6-bromo-1-indanone (prepared as described by Cornelius, Lyndon A. M. and Combs, Donald W. Synth. Commun. (1994), 24(19), 2777–88) (1.4 g, 6.57 mmol) in 20 mL of methanol was added sodium borohydride (0.087 g, 2.3 mmol) over a period of five minutes at room temperature. The reaction mixture was stirred for two hours at room temperature, concentrated under pressure and partitioned between ethyl acetate (50 mL) and 1N HCl (20 mL). The ethyl acetate layer was dried over sodium sulfate and concentrated under reduced pressure to yield the title compound as a solid (1.4 g, 99%). $^1$H NMR (CDCl$_3$): δ 7.45 (s, 1H), 7.3 (d, 1H), 7.0 (d, 1H), 5.2 (t, 1H), 2.9 (m, 1H), 2.7 (m, 1H), 2.4 (m, 1H), 1.9 (m, 2H).

Example 10 Part B

6-Bromo-1-(dimethylamino)-2,3-dihydro-1H-indene

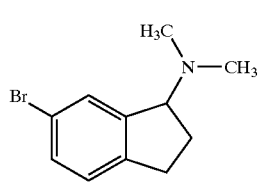

10B

To a solution of 10A (0.767 g, 3.56 mmol) in anhydrous toluene (10 mL) was added thionyl chloride (0.4 mL, 5.34 mmol) at room temperature. The reaction mixture was stirred at room temperature for twenty minutes and heated at 50° C. for one hour. The reaction mixture was concentrated under reduced pressure and partitioned between dichloromethane (20 mL) and water (20 mL). The dichloromethane layer is dried over sodium sulfate and concentrated under reduced pressure to yield a liquid (0.641 g), which was used as such for the subsequent step without further purification.

To the liquid obtained above (0.641 g) was added dimethylamine (2 mL of a 33% solution in ethyl alcohol) and the contents were heated in a sealed tube at 90° C. for eighteen hours. The reaction mixture was cooled to room temperature, concentrated under reduced pressure and purified by flash column chromatography using dichloromethane-methanol (18:1) as the eluent to yield the title compound as an oil (0.362 g, 42% over two steps). $^1$H NMR (CDCl$_3$): δ 7.45 (s, 1H), 7.3 (d, 1H), 7.0 (d, 1H), 4.2 (t, 1H), 2.9 (m, 1H), 2.8 (m, 1H), 2.2 (s, 6H), 1.95 (m, 2H).

Example 10, Part C

1-(Dimethylamino)-2,3-dihydro-6-[(trimethylsilyl)ethynyl]-1H-indene

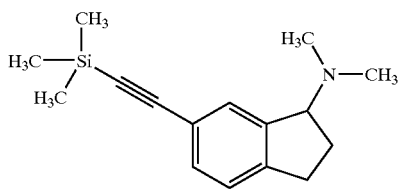

10C

To 10B (0.29 g, 1.21 mmol), under a nitrogen atmosphere was sequentially added triethylamine (0.37 mL, 2.66 mmol), copper(I)iodide (0.018 g, 0.0968 mmol), bis(triphenylphosphine)palladium(II)dichloride (0.034 g, 0.0484 mmol) and trimethylsilyl acetylene (0.2 mL, 1.45 mmol). The reaction mixture was heated at 80° C. for two hours. The reaction mixture was cooled to room temperature, dichloromethane (20 mL) was added and the contents filtered over a thin pad of celite. The filtrate is concentrated under reduced pressure and purified by flash column chromatography using dichloromethane-methanol (18:1) as the eluent to yield the title compound as an oil (0.300 g, 96%). $^1$H NMR (CDCl$_3$): δ 7.5 (s, 1H), 7.3 (d, 1H), 7.1 (d, 1H), 4.3 (t, 1H), 2.9 (m, 1H), 2.8 (m, 1H), 2.2 (s, 6H), 2.1 (m, 2H), 0.2 (s, 9H).

Example 10, Part D

1-(Dimethylamino)-6-ethynyl-2,3-dihydro-1H-indene

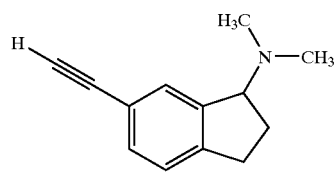

10D

To a solution of XC (0.3 g, 1.16 mmol) in anhydrous THF (5 mL) was added tetrabutylammonium fluoride (1.4 mL, 1.39 mmol of a 1.0M solution in THF) at room temperature. The reaction mixture was stirred at room temperature for two hours, concentrated under reduced pressure and purified by flash column chromatography using dichloromethane-methanol (18:1) as the eluent to yield the title compound as an oil (0.18 g, 83%). $^1$H NMR (CDCl$_3$): δ 7.45 (s, 1H), 7.3 (d, 1H), 7.1 (d, 1H), 4.2 (t, 1H), 2.95 (s, 1H), 2.9 (m, 1H), 2.8 (m, 1H), 2.2 (s, 6H), 2.0 (m, 2H).

Example 10, Part E

2-[2,3-Dihydro-3-(dimethylamino)-1H-inden-5-yl]-7-methoxy-6-(5-oxazolyl)-4(1H)-quinolinone 4A 0.15 g (0.47 mmol), 0.18 g (0.94 mmol) of 10D, 0.02 g (0.028 mmol) of bis(triphenylphosphine)palladium(II) dichloride and diethylamine (5 mL) were reacted in a similar manner to Example 5, part D. The reaction was conducted at 120° C. for 30 minutes and then cooled to room temperature. Methanol (60 mL) was added and the contents filtered. The residue was concentrated under reduced pressure and purified by flash column chromatography using dichloromethane-methanol (7:3) as the eluent to yield the title compound as a solid (0.135 g, 71%). LC/MS (retention time=2.31 min.; M$^+$ 402.24. Column: YMC ODSA 5u C18 4.6×50 mm (4 min. gradient. Solvent A=10% MeOH, 90% H$_2$O, 0.1% TFA; Solvent B=90% MeOH, 10% H$_2$O, 0.1% TFA).

EXAMPLE 11

2-(2,3-Dihydro-3-methoxy-1H-inden-5-yl)-7-methoxy-6-(5-oxazolyl)-4(1H)-quinolinone

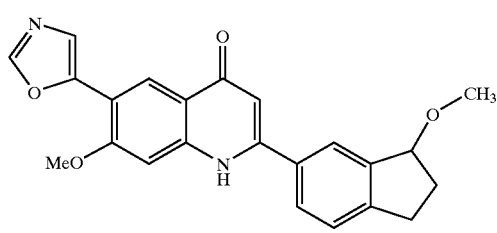

11

Example 11, Part A

6-Bromo-2,3-dihydro-1-methoxy-1H-indene

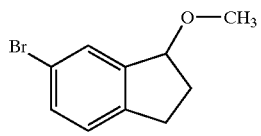
11A

To a solution of 10A (0.51 g, 2.4 mmol) in 10 mL of anhydrous THF was added sodium hydride (0.097 g, 3.84 mmol) over a period of 5 minutes at room temperature. After stirring the reaction mixture for fifteen minutes at room temperature, methyl iodide (0.22 mL, 3.6 mmol) was added and the contents stirred at room temperature for thirty minutes. The reaction mixture was concentrated and partitioned between ethyl acetate (20 mL) and water (20 mL). The ethyl acetate layer was washed with 1N HCl (20 mL), brine (20 mL), dried over sodium sulfate and concentrated to yield the title compound as a liquid (0.485 g, 89%). $^1$H NMR (CDCl$_3$): δ 7.45 (s, 1H), 7.3 (d, 1H), 7.0 (d, 1H), 4.7 (m, 1H), 3.3 (s, 3H), 2.9 (m, 1H), 2.8 (m, 1H), 2.3 (m, 1H), 2.0 (m, 1H).

Example 11, Part B 2,3-Dihydro-1-methoxy-6-[(trimethylsilyl)ethynyl]-1H-indene

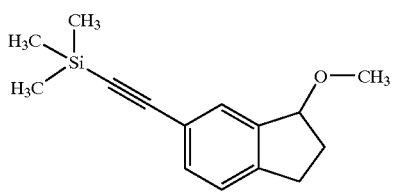
11B 11A 0.485 g (2.14 mmol), 0.36 mL (2.56 mmol) of trimethylsilyl acetylene, 0.06 g (0.085 mmol) of bis(triphenylphosphine)palladium(II)dichloride, 0.032 g (0.171 mmol) of copper(I)iodide and 0.65 mL (4.7 mmol) of triethylamine were reacted in a similar manner to Example 10, part C, to yield the title compound as an oil (0.5 g, 96%). $^1$H NMR (CDCl$_3$): δ 7.3 (s, 1H), 7.2 (d, 1H), 7.0 (d, 1H), 4.6 (m, 1H), 3.2 (s, 3H), 2.9 (m, 1H), 2.6 (m, 1H), 2.2 (m, 1H), 1.95 (m, 1H). 0.1 (s, 3H).

Example 11, Part C

6-Ethynyl-2,3-dihydro-1-methoxy-1H-indene

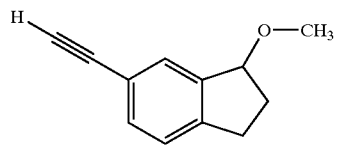
11C 11B, 0.5 g (2.05 mmol) and 2.46 mL (2.46 mmol of 1.0M solution in THF) of tetrabutylammonium flouride were reacted in a similar manner to example 10, part D, to yield the title compound as an oil (0.5 g, 99%). $^1$H NMR (CDCl$_3$) δ 7.45 (s, 1H), 7.3 (d, 1H), 7.1 (d, 1H), 4.8 (m, 1H), 3.3 (s, 3H), 3.0 (m, 2H), 2.75 (m, 1H), 2.25 (m, 1H), 2.0 (m, 1H).

Example 11, Part D 2-(2,3-Dihydro-3-methoxy-1H-inden-5-yl)-7-methoxy-6-(5-oxazolyl)-4(1H)-quinolinone 4A, 0.15 g (0.47 mmol), 0.163 g (0.94 mmol) of 11D, 0.02 g (0.028 mmol) of bis(triphenylphosphine)palladium (II)dichloride and diethylamine (5 mL) were reacted in a similar manner were reacted in a similar manner to Example 5, part D to yield the title compound as a solid (0.04 g, 21%). $^1$H NMR (CDCl$_3$): δ 11.8 (S, 1H), 8.5 (s, 1H), 8.4 (s, 1H), 7.8 (s, 1H), 7.75 (d, 1H), 7.6 (s, 1H), 7.4 (d, 1H), 7.35 (s, 1H), 6.3 (s, 1H), 4.9 (m, 1H), 4.1 (s, 3H), 3.3 (s, 3H), 3.0 (m, 1H), 2.85 (m, 1H), 2.4 (m, 1H), 2.0 (m, 1H).

EXAMPLES 12 to 103

Examples 12 to 103 are prepared by several routes. The method to prepare a specific example is noted in table 1. Examples prepared in a manner analogous to Example 1 starting with aniline 1D and an appropriate beta-ketoester are designated as method A1. Examples prepared in a manner analogous to Example 2 starting with aniline 1D and a appropriate beta-ketoester, which may be obtained from commercially available acid chlorides, are designated as method A2. Example prepared from esters, which are readily converted to an acid by hydrolysis, or acids, followed by reaction of the acid with carbonyldiimidazole, and reacted with potassium ethyl malonate as described in Example 6, part A, are designated as method A3. Examples which starting with intermediate 3A, and react in a manner analogous to example 3, are designated as method B1. Compounds prepared in a manner analogous to Example 9 are designated as method B2 Examples which starting with intermediate 4A, and react it with a commercially available terminal alkyne, prepared in a manner analogous to example 4, are designated as method C1. Examples which starting with intermediate 4A, and react it with a terminal alkyne, which is prepared from a commercially available aryl halide and trimethylsilylacetylene as described in Example 5, Part B and Part C, and then reacted to form a quinolone in a manner analogous to example 4, are designated as method C2. Compounds prepared in a manner analogous to Example 7 are designated as method D1. Compounds prepared in a manner analogous to Example 8 are designated as method D2. The compounds of these examples have structures outlined in Table 1 below.

Column conditions A: YMC ODSA S5 C18 4.6×50 mm (4 min. gradient. Solvent A=10% MeOH, 90% H$_2$O, 0.1% TFA; Solvent B=90% MeOH, 10% H$_2$O, 0.1% TFA).

Column conditions B: Column: YMC S5 Turbopack Pro 4.6×33 mm (2 min. gradient. Solvent A=10% MeOH, 90% H$_2$O, 0.1% TFA; Solvent B=90% MeOH, 10% H$_2$O, 0.1% TFA).

Column conditions C: YMC ODSA 5μ C18 4.6×50 mm (4 min. gradient. Solvent A=10% MeOH, 90% H$_2$O, 0.1% TFA; Solvent B=90% MeOH, 10% H$_2$O, 0.1% TFA).

Column conditions D: YMC S5 CombiScreen 4.6×50 mm; Gradient time: 4 min; Flow rate=4 ml/min; Solvent A 10% MeOH, 90% Water, 0.2% H$_3$PO$_4$; Solvent B=90% MeOH, 10% water, 0.2% H$_3$PO$_4$ Start % B=0; Final % B=100;

Column conditions E: YMC S5 ODS 4.6×50 mm; Gradient time: 4 min; Flow rate=4 ml/min; Solvent A=10% MeOH, 90% Water, 0.2% H$_3$PO$_4$; Solvent B=90% MeOH, 10% water, 0.2% H$_3$PO$_4$ Start % B=0; Final % B=100;

Column condition F: YMC PRO S5 4.6×33 mm; Gradient time: 2 min; Flow rate=4 mL/min; Solvent A=10% MeOH, 90% H$_2$O, 0.1% TFA; Solvent B=90% MeOH, 10% H$_2$O, 0.1% TFA; Start % B=0; Final % B=100.

TABLE 1

| EX. No | R¹ | R³ | Compound Name | Method | HPLC Conditions/ time (min.) | M + H⁺ |
|---|---|---|---|---|---|---|
| 12 | 3-furanyl | H | 7-Methoxy-2-(3-furanyl)-6-(5-oxazolyl)-4(1H)-quinolinone | A1 | E/3.10 | 299.22 |
| 13 | 3-methylphenyl | H | 7-Methoxy-2-(3-methylphenyl)-6-(5-oxazolyl)-4(1H)-quinolinone | C1 | E/3.55 | 333.16 |
| 14 | 2-fluorophenyl | H | 2-(2-Fluorophenyl)-7-methoxy-6-(5-oxazolyl)-4(1H)-quinolinone | A1 | E/2.73 | 337.16 |
| 15 | Me | H | 7-Methoxy-2-methyl-6-(5-oxazolyl)-4(1H)-quinolinone | A1 | E/2.00 | 257.14 |
| 16 | phenyl | Me | 7-Methoxy-3-methyl-6-(5-oxazolyl)-2-phenyl-4(1H)-quinolinone | A1 | E/2.98 | 333.09 |
| 17 | 2-pyrrolidinyl | H | 7-Methoxy-6-(5-oxazolyl)-2-(2-pyrrolidinyl)-4(1H)-quinolinone | A1 | A/1.86 | 312.20 |
| 18 | N-Cbz-2-pyrrolidinyl | H | 2-[1,4-Dihydro-7-methoxy-6-(5-oxazolyl)-4-oxo-2-quinolinyl]-1-pyrrolidine-carboxylic acid phenylmethyl ester | A1 | A/2.71 | 446.14 |
| 19 | 3-(N-methyl-N-(2-hydroxyacetyl)amino)phenyl | H | N-[3-[1,4-Dihydro-7-methoxy-6-(5-oxazolyl)-4-oxo-2-quinolinyl]phenyl]-2-hydroxy-N-methylacetamide | C2 | D/2.44 | 448.14 |

TABLE 1-continued

| EX. No | R¹ | R³ | Compound Name | Method | HPLC Conditions/ time (min.) | M + H⁺ |
|---|---|---|---|---|---|---|
| 20 | H₃C-N(phenyl)-C(=O)-CH₂-O-C(=O)-CH₃ | H | 2-(Acetyloxy)-N-[3-[1,4-dihydro-7-methoxy-6-(5-oxazolyl)-4-oxo-2-quinolinyl]phenyl]-N-methylacetamide | C2 | D/2.64 | 406.12 |
| 21 | H₃C-N(phenyl)-C(=O)-CH₂-morpholine | H | N-[3-[1,4-Dihydro-7-methoxy-6-(5-oxazolyl)-4-oxo-2-quinolinyl]phenyl]-N-methyl-4-morpholineacetamide | C2 | D/1.97 | 475.42 |
| 22 | 4-(methoxycarbonyl)phenyl | H | 4-[1,4-Dihydro-7-methoxy-6-(5-oxazolyl)-4-oxo-2-quinolinyl]benzoic acid methyl ester | A2 | E/2.95 | 377.20 |
| 23 | 4-methoxyphenyl | H | 7-Methoxy-2-(4-methoxyphenyl)-6-(5-oxazolyl)-4(1H)-quinolinone | A1 | E/2.80 | 349.18 |
| 24 | 3-pyridinyl | H | 7-Methoxy-6-(5-oxazolyl)-2-(3-pyridinyl)-4(1H)-quinolinone | A1 | E/2.12 | 320.13 |
| 25 | (CH₃)₂C-CH₂-C(=O)-N(CH₂CH₃)₂ | H | N,N-Diethyl-1,4-dihydro-7-methoxy-6-(5-oxazolyl)-4-oxo-2-quinolinepropamide | C1 | D/2.42 | 370.38 |
| 26 | benzyl | H | 7-Methoxy-6-(5-oxazolyl)-2-(phenylmethyl)-4(1H)-quinolinone | A2 | E/2.68 | 333.16 |
| 27 | 4-hydroxyphenyl | H | 2-(4-Hydroxyphenyl)-7-methoxy-6-(5-oxazolyl)-4(1H)-quinolinone | A2 | 2.69 | 335.12 |

TABLE 1-continued

| EX. No | R¹ | R³ | Compound Name | Method | HPLC Conditions/ time (min.) | M + H⁺ |
|---|---|---|---|---|---|---|
| 28 | 3,4-dimethylphenyl | H | 2-(3,4-Dimethylphenyl)-7-methoxy-6-(5-oxazolyl)-4(1H)-quinolinone | A3 | E/3.17 | 347.19 |
| 29 | 4-(3-methoxycarbonylpropyl)phenyl | H | 4-[1,4-Dihydro-7-methoxy-6-(5-oxazolyl)-4-oxo-2-quinolinyl]benzene-butanoic acid methyl ester | C2 | D/3.17 | 419.1 |
| 30 | 4-(3-carboxypropyl)phenyl | H | 4-[1,4-Dihydro-7-methoxy-6-(5-oxazolyl)-4-oxo-2-quinolinyl]benzene-butanoic acid | C2 | D/2.94 | 405.11 |
| 31 | 4-(carboxymethyl)phenyl | H | 4-[1,4-Dihydro-7-methoxy-6-(5-oxazolyl)-4-oxo-2-quinolinyl]benzene-acetic acid | C2 | D/2.65 | 377.14 |
| 32 | 3-thienyl | H | 7-Methoxy-6-(5-oxazolyl)-2-(3-thienyl)-4(1H)-quinolinone | A1 | A/2.88 | 325.10 |
| 33 | 2-thienyl | H | 7-Methoxy-6-(5-oxazolyl)-2-(2-thienyl)-4(1H)-quinolinone | A1 | C/2.72 | 325.05 |
| 34 | 3-(4-morpholinyl)phenyl | H | 7-Methoxy-2-[3-(4-morpholinyl)phenyl]-6-(5-oxazolyl)-4(1H)-quinolinone | B1 | B/1.43 | 404.22 |
| 35 | 2-methylphenyl | H | 7-Methoxy-2-(2-methylphenyl)-6-(5-oxazolyl)-4(1H)-quinolinone | A3 | C/2.76 | 333.10 |

TABLE 1-continued

| EX. No | R¹ | R³ | Compound Name | Method | HPLC Conditions/ time (min.) | M + H⁺ |
|---|---|---|---|---|---|---|
| 36 | 3-(1-piperidinyl)phenyl | H | 7-Methoxy-2-[3-(1-piperidinyl)phenyl]-6-(5-oxazolyl)-4(1H)-quinolinone | B1 | A/2.32 | 402.36 |
| 37 | 3-[(Dimethylamino)methyl]phenyl | H | 2-[3-[(Dimethylamino)methyl]phenyl]-7-methoxy-6-(5-oxazolyl)-4(1H)-quinolinone | A3 | C/2.20 | 376.19 |
| 38 | 3-[(Dimethylamino)methyl]phenyl | Br | 3-Bromo-2-[3-[(dimethylamino)methyl]phenyl]-7-methoxy-6-(5-oxazolyl)-4(1H)-quinolinone | A3 | A/2.24 | 456.25 |
| 39 | 3-(2-carboxyethyl)phenyl | H | 3-[1,4-Dihydro-7-methoxy-6-(5-oxazolyl)-4-oxo-2-quinolinyl]benzenepropanoic acid | C2 | D/2.82 | 391.13 |
| 40 | -CH₂CH₂OH | H | 2-(2-Hydroxyethyl)-7-methoxy-6-(5-oxazolyl)-4(1H)-quinolinone | C1 | D/1.75 | 287.13 |
| 41 | -CH₂N(CH₃)₂ | H | 2-[(Dimethylamino)methyl]-7-methoxy-6-(5-oxazolyl)-4(1H)-quinolinone | C1 | D/1.18 | 300.16 |
| 42 | -CH₂CH₂CH₂OH | H | 2-(3-Hydroxypropyl)-7-methoxy-6-(5-oxazolyl)-4(1H)-quinolinone | C1 | D/1.94 | 301.15 |
| 43 | -CH₂CH₂CH₂CH₂OH | H | 2-(4-Hydroxybutyl)-7-methoxy-6-(5-oxazolyl)-4(1H)-quinolinone | C1 | D/2.06 | 315.16 |

TABLE 1-continued

| EX. No | R[1] | R[3] | Compound Name | Method | HPLC Conditions/ time (min.) | M + H[+] |
|---|---|---|---|---|---|---|
| 44 | 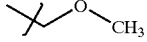 | H | 2-(Hydroxymethyl)-7-methoxy-6-(5-oxazolyl)-4(1H)-quinolinone | C1 | D/1.75 | 273.1 |
| 45 | 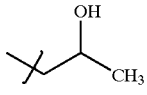 | H | 7-Methoxy-2-(methoxymethyl)-6-(5-oxazolyl)-4(1H)-quinolinone | C1 | D/2.09 | 287.12 |
| 46 | 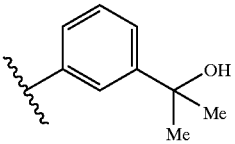 | H | 2-(2-Hydroxypropyl)-7-methoxy-6-(5-oxazolyl)-4(1H)-quinolinone | C1 | D/1.90 | 301.17 |
| 47 | 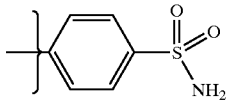 | H | 2-[3-(1-Hydroxy-1-methylethyl)phenyl]-7-methoxy-6-(5-oxazolyl)-4(1H)-quinolinone | A3 | E/2.77 | 377.22 |
| 48 | 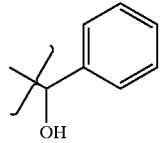 | H | 4-[1,4-Dihydro-7-methoxy-6-(5-oxazolyl)-4-oxo-2-quinolinyl]benzene-sulfonamide | A3 | E/2.35 | 398.16 |
| 49 | 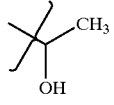 | H | 2-(Hydroxyphenylmethyl)-7-methoxy-6-(5-oxazolyl)-4(1H)-quinolinone | C1 | D/3.31 | 349.24 |
| 50 | 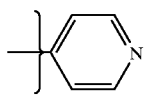 | H | 2-(1-Hydroxyethyl)-7-methoxy-6-(5-oxazolyl)-4(1H)-quinolinone | C1 | D/2.08 | 273.16 |
| 51 | 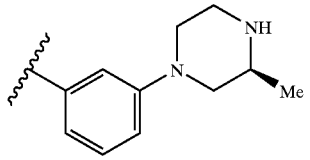 | H | 7-Methoxy-6-(5-oxazolyl)-2-(4-pyridinyl)-4(1H)-quinolinone | A3 | E/2.00 | 320.12 |
| 52 |  | H | 7-Methoxy-2-[3-[(3S)-3-methyl-1-piperazinyl]phenyl]-6-(5-oxazolyl)-4(1H)-quinolinone | B2 | D/2.833 | 417 |

TABLE 1-continued

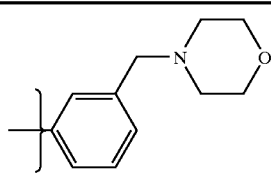

| EX. No | R¹ | R³ | Compound Name | Method | HPLC Conditions/ time (min.) | M + H⁺ |
|---|---|---|---|---|---|---|
| 53 | 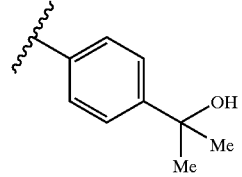 | H | 7-Methoxy-2-[3-(4-morpholinyl-methyl)phenyl]-6-(5-oxazolyl)-4(1H)-quinolinone | A3 | 1.92 | 418.20 |
| 54 | 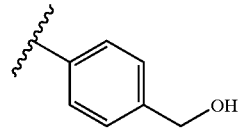 | H | 2-[4-(1-Hydroxy-1-methylethyl)phenyl]-7-methoxy-6-(5-oxazolyl)-4(1H)-quinolinone | D2 | 2.70 | 377.28 |
| 55 | 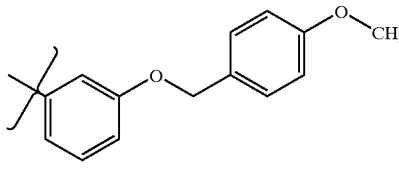 | H | 2-[4-(Hydroxy-methyl)phenyl]-7-methoxy-6-(5-oxazolyl)-4(1H)-quinolinone | D1 | 2.45 | 349.23 |
| 56 | 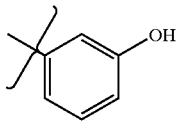 | H | 7-Methoxy-2-[3-[(4-methoxyphenyl)meth-oxy]phenyl]-6-(5-oxazolyl)-4(1H)-quinolinone | A3 | E/3.54 | 455.10 |
| 57 | 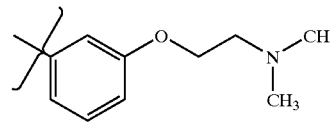 | H | 2-(3-Hydroxyphenyl)-7-methoxy-6-(5-oxazolyl)-4(1H)-quinolinone | A3 | E/2.76 | 355.10 |
| 58 | 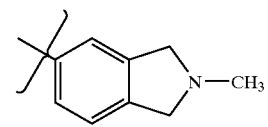 | H | 2-[3-[2-(Dimethyl-amino)ethoxy]phenyl]-7-methoxy-6-(5-oxazolyl)-4(1H)-quinolinone | A3 | E/2.28 | 406.37 |
| 59 | 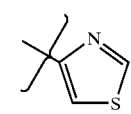 | H | 2-(2,3-Dihydro-1-methyl-1H-isoindol-5-yl)-7-methoxy-6-(5-oxazolyl)-4(1H)-quinolinone | C2 | E/2.18 | 374.16 |
| 60 | | H | 7-Methoxy-6-(5-oxazolyl)-2-(4-thiazolyl)-4(1H)-quinolinone | A3 | E/2.67 | 326.05 |

TABLE 1-continued

| EX. No | R¹ | R³ | Compound Name | Method | HPLC Conditions/ time (min.) | M + H⁺ |
|---|---|---|---|---|---|---|
| 61 | (4-tert-butyl-2-(1-piperidinyl)thiazolyl) | H | 7-Methoxy-6-(5-oxazolyl)-2-[2-(1-piperidinyl)-4-thiazolyl]-4(1H)-quinolinone | C2 | E/3.49 | 409.10 |
| 62 | (3,5-dimethylphenyl) | H | 2-(3,5-Dimethylphenyl)-7-methoxy-6-(5-oxazolyl)-4(1H)-quinolinone | C2 | E/3.36 | 347.15 |
| 63 | (3-(methylthio)phenyl) | H | 7-Methoxy-2-[3-(methylthio)phenyl]-6-(5-oxazolyl)-4(1H)-quinolinone | C2 | E/3.29 | 365.08 |
| 64 | (3-(methylsulfonyl)phenyl) | H | 7-Methoxy-2-[3-(methylsulfonyl)phenyl]-6-(5-oxazolyl)-4(1H)-quinolinone | C2 | E/2.47 | 397.07 |
| 65 | (3-[4-(2-methoxyethyl)-1-piperazinyl]phenyl) | H | 7-Methoxy-2-[3-[4-(2-methoxyethyl)-1-piperazinyl]phenyl]-6-(5-oxazolyl)-4(1H)-quinolinone | B2 | A/2.42 | 461.54 |
| 66 | (3-(2,6-dimethyl-4-morpholinyl)phenyl) | H | 2-[3-(2,6-Dimethyl-4-morpholinyl)phenyl]-7-methoxy-6-(5-oxazolyl)-4(1H)-quinolinone | B2 | A/3.11 | 432.23 |
| 67 | (3-bromo-4-methylphenyl) | H | 2-(3-Bromo-4-methylphenyl)-7-methoxy-6-(5-oxazolyl)-4(1H)-quinolinone | A1 | A/3.31 | 411.08 |

TABLE 1-continued

| EX. No | R¹ | R³ | Compound Name | Method | HPLC Conditions/ time (min.) | M + H⁺ |
|---|---|---|---|---|---|---|
| 68 | 3-[[(tetrahydro-2-furanyl)methyl]amino]phenyl | H | 7-Methoxy-6-(5-oxazolyl)-2-[3-[[(tetrahydro-2-furanyl)methyl]amino]phenyl]-4(1H)-quinolinone | B2 | A/2.91 | 418.23 |
| 69 | 3-[3-(dimethylamino)-1-pyrrolidinyl]phenyl | H | 2-[3-[3-(Dimethylamino)-1-pyrrolidinyl]phenyl]-7-methoxy-6-(5-oxazolyl)-4(1H)-quinolinone | B2 | A/2.46 | 431.25 |
| 70 | 2-methyl-5-morpholinophenyl | H | 2-[3-[3-(Dimethylamino)-1-pyrrolidinyl]phenyl]-7-methoxy-6-(5-oxazolyl)-4(1H)-quinolinone | B2 | A/3.07 | 418.21 |
| 71 | 4-methyl-3-(4-methyl-1-piperazinyl)phenyl | H | 7-Methoxy-2-[4-methyl-3-(4-methyl-1-piperazinyl)phenyl]-6-(5-oxazolyl)-4(1H)-quinolinone | B2 | A/2.54 | 431.25 |
| 72 | 4-methyl-3-(4-Boc-piperazinyl)phenyl | H | 4-[5-[1,4-Dihydro-7-methoxy-6-(5-oxazolyl)-4-oxo-2-quinolinyl]-2-methylphenyl]-1-piperazinecarboxylic acid 1,1-dimethylethyl ester | B2 | A/3.57 | 517.29 |
| 73 | 4-methyl-3-(1-pyrrolidinyl)phenyl | H | 7-Methoxy-2-[4-methyl-3-(1-pyrrolidinyl)phenyl]-6-(5-oxazolyl)-4(1H)-quinolinone | B2 | A/2.46 | 402.22 |
| 74 | 3-[(2-methoxyethyl)amino]-4-methylphenyl | H | 7-Methoxy-2-[3-[(2-methoxyethyl)amino]-4-methylphenyl]-6-(5-oxazolyl)-4(1H)-quinolinone | B2 | A/2.93 | 406.22 |

TABLE 1-continued

| EX. No | R¹ | R³ | Compound Name | Method | HPLC Conditions/time (min.) | M + H⁺ |
|---|---|---|---|---|---|---|
| 75 | [structure: 5-position of phenyl attached; 2-Me, 3-NH-piperidin-4-yl with N-C(O)OEt... actually N-acyl: Me-CH2-C(O)-N-piperidine] | H | 4-[[5-[1,4-Dihydro-7-methoxy-6-(5-oxazolyl)-4-oxo-2-quinolinyl]-2-methylphenyl]amino]-1-piperidinecarboxylic acid ethyl ester | B2 | A/3.18 | 503.27 |
| 76 | [structure: 2-methyl-5-yl phenyl with 3-[(3R)-3-(dimethylamino)pyrrolidin-1-yl]] | H | 2-[3-[(3R)-3-(Dimethylamino)-1-pyrrolidinyl]-4-methylphenyl]-7-methoxy-6-(5-oxazolyl)-4(1H)-quinolinone | B2 | A/2.57 | 445.29 |
| 77 | [structure: 2,3-dihydro-1H-inden-5-yl with 3-(1-pyrrolidinyl)] — actually piperazinyl phenyl | H | 2-[2,3-Dihydro-3-(1-pyrrolidinyl)-1H-inden-5-yl]-7-methoxy-6-(5-oxazolyl)-4(1H)-quinolinone | B2 | A/2.55 | 417.23 |
| 78 | [structure: 2-methyl-5-yl phenyl with 3-thiomorpholinyl] | H | 7-Methoxy-2-[4-methyl-3-(1-piperazinyl)phenyl]-6-(5-oxazolyl)-4(1H)-quinolinone | B2 | A/3.37 | 434.19 |
| 79 | [structure: 3-bromo-4-methoxyphenyl] | H | 2-(3-Bromo-4-methoxyphenyl)-7-methoxy-6-(5-oxazolyl)-4(1H)-quinolinone | A1 | B/1.66 | 429.06 |
| 80 | [structure: 2-methyl-5-yl phenyl with 3-(1,1-dioxido-4-thiomorpholinyl)] | H | 2-[3-(1,1-Dioxido-4-thiomorpholinyl)-4-methylphenyl]-7-methoxy-6-(5-oxazolyl)-4(1H)-quinolinone | B2 | B/1.48 | 466.14 |

TABLE 1-continued

| EX. No | R¹ | R³ | Compound Name | Method | HPLC Conditions/ time (min.) | M + H⁺ |
|---|---|---|---|---|---|---|
| 81 | 5-(2-OMe-phenyl) with 4-morpholinyl at 3-position | H | 7-Methoxy-2-[4-methoxy-3-(4-morpholinyl)phenyl]-6-(5-oxazolyl)-4(1H)-quinolinone | B2 | B/1.50 | 434.25 |
| 82 | 5-(2-OMe-phenyl) with (2R)-2-(methoxymethyl)-1-pyrrolidinyl at 3-position | H | 7-Methoxy-2-[4-methoxy-3-[(2R)-2-(methoxymethyl)-1-pyrrolidinyl]phenyl]-6-(5-oxazolyl)-4(1H)-quinolinone | B2 | A/2.51 | 462.53 |
| 83 | 5-(2-OMe-phenyl) with 1-azetidinyl at 3-position | H | 2-[3-(1-Azetidinyl)-4-methoxyphenyl]-7-methoxy-6-(5-oxazolyl)-4(1H)-quinolinone | B2 | A/2.55 | 404.45 |
| 84 | 5-(2-OMe-phenyl) with 4-methyl-1-piperazinyl at 3-position | H | 7-Methoxy-2-[4-methoxy-3-(4-methyl-1-piperazinyl)phenyl]-6-(5-oxazolyl)-4(1H)-quinolinone | B2 | A/2.41 | 447.51 |
| 85 | 5-(2-OMe-phenyl) with [2-(methylamino)ethyl]amino at 3-position | H | 7-Methoxy-2-[4-methoxy-3-[[2-(methylamino)ethyl]amino]phenyl]-6-(5-oxazolyl)-4(1H)-quinolinone | B2 | A/2.50 | 421.48 |
| 86 | 5-(2-OMe-phenyl) with (3R)-3-(dimethylamino)-1-pyrrolidinyl at 3-position | H | 2-[3-[(3R)-3-(Dimethylamino)-1-pyrrolidinyl]-4-methoxyphenyl]-7-methoxy-6-(5-oxazolyl)-4(1H)-quinolinone | B2 | A/2.50 | 461.55 |

TABLE 1-continued

| EX. No | R¹ | R³ | Compound Name | Method | HPLC Conditions/ time (min.) | M + H⁺ |
|---|---|---|---|---|---|---|
| 87 | (5-substituted-2-methoxyphenyl)-NH-CH₂CH₂-O-Me | H | 7-Methoxy-2-[4-methoxy-3-[(2-methoxy-ethyl)amino]phenyl]-6-(5-oxazolyl)-4(1H)-quinolinone | B2 | A/2.91 | 422.46 |
| 88 | (5-substituted-2-methoxyphenyl)-NH-CH₂CH₂-morpholinyl | H | 7-Methoxy-2-[4-methoxy-3-[[2-(4-morpholinyl)eth-yl]amino]phenyl]-6-(5-oxazolyl)-4(1H)-quinolinone | B2 | A/2.50 | 477.57 |
| 89 | 3-cyano-4-methylphenyl | H | 5-[1,4-Dihydro-7-methoxy-6-(5-oxazolyl)-4-oxo-2-quinolinyl]-2-methylbenzonitrile | B3 | E/3.57 | 358.38 |
| 90 | 8-oxo-5,6,7,8-tetrahydronaphthalen-2-yl | H | 7-Methoxy-6-(5-oxazolyl)-2-(5,6,7,8-tetrahydro-8-oxo-2-naphthalenyl)-4(1H)-quinolinone | C3 | A/2.95 | 387.10 |
| 91 | 8-hydroxy-5,6,7,8-tetrahydronaphthalen-2-yl | H | 7-Methoxy-6-(5-oxazolyl)-2-(5,6,7,8-tetrahydro-8-hydroxy-2-naphthalenyl)-4(1H)-quinolinone | D3 | A/2.91 | 389.19 |

TABLE 1-continued

| EX. No | R¹ | R³ | Compound Name | Method | HPLC Conditions/ time (min.) | M + H⁺ |
|---|---|---|---|---|---|---|
| 92 | Me-N(Me)-C(=O)-O- tetrahydronaphthalenyl | H | Dimethylcarbamic acid 7-[1,4-dihydro-7-methoxy-6-(5-oxazolyl)-4-oxo-2-quinolinyl]-1,2,3,4-tetrahydro-1-naphthalenyl ester | D3 | A/3.34 | 460.41 |
| 93 | Me-N(Me)- tetrahydronaphthalenyl | H | 2-[8-(Dimethylamino)-5,6,7,8-tetrahydro-2-naphthalenyl]-7-methoxy-6-(5-oxazolyl)-4(1H)-quinolinone | D3 | A/2.43 | 416.20 |
| 94 | -CH₂CH₂Me (ethyl) | H | 2-Ethyl-7-methoxy-6-(5-oxazolyl)-4(1H)-quinolinone | A1 | E/1.33 | 271 |
| 95 | 3-CF₃-phenyl | H | 7-Methoxy-6-(5-oxazolyl)-2-[3-(trifluoromethyl)phenyl]-4(1H)-quinolinone | A1 | E/3.18 | 387.21 |
| 96 | 4-CF₃-phenyl | H | 7-Methoxy-6-(5-oxazolyl)-2-[4-(trifluoromethyl)phenyl]-4(1H)-quinolinone | A1 | E/3.16 | 387.22 |
| 97 | 4-(Me₂N)-chroman-6-yl | H | 2-[4-(Dimethylamino)-3,4-dihydro-2H-1-benzopyran-6-yl]-7-methoxy-6-(5-oxazolyl)-4(1H)-quinolinone | C1 | E/1.40 | 418.09 |
| 98 | cyclohexyl | H | 2-Cyclohexyl-7-methoxy-6-(5-oxazolyl)-4(1H)-quinolinone | C1 | E/1.73 | 271.1 |

TABLE 1-continued

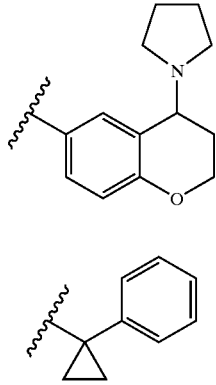

| EX. No | R¹ | R³ | Compound Name | Method | HPLC Conditions/ time (min.) | M + H⁺ |
|---|---|---|---|---|---|---|
| 99 | 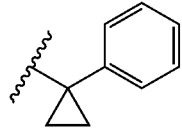 | H | 2-[3,4-Dihydro-4-(1-pyrrolidinyl)-2H-1-benzopyran-6-yl]-7-methoxy-6-(5-oxazolyl)-4(1H)-quinolinone | C1 | E/1.73 | 444.54 |
| 100 | 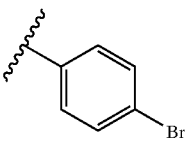 | H | 7-Methoxy-6-(5-oxazolyl)-2-(1-phenylcyclopropyl)-4(1H)-quinolinone | C1 | E/1.76 | 325.15 |
| 101 | 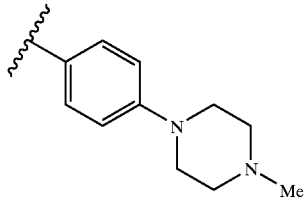 | H | 2-(4-Bromophenyl)-7-methoxy-6-(5-oxazolyl)-4(1H)-quinolinone | A3 | D/3.24 | 397.11 |
| 102 | 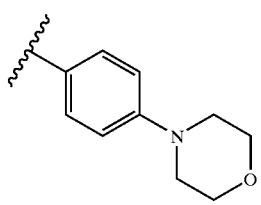 | H | 7-Methoxy-2-[4-(4-methyl-1-piperazinyl)phenyl]-6-(5-oxazolyl)-4(1H)-quinolinone | C2 | D/1.91 | 417.16 |
| 103 |  | H | 7-Methoxy-2-[4-(4-morpholinyl)phenyl]-6-(5-oxazolyl)-4(1H)-quinolinone | C2 | D/2.84 | 404.15 |

EXAMPLE 104

[6-[1,4-Dihydro-7-methoxy-6-(5-oxazolyl)-4-oxo-2-quinolinyl]-2,3-dihydro-1H-inden-1-yl]methylcarbamic acid phenylmethyl ester

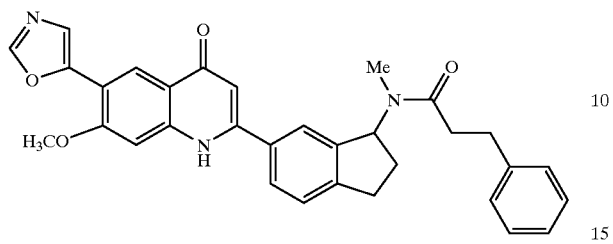

Example 104, Part A

6-Bromo-2,3-dihydro-N-methyl-1H-inden-1-amine

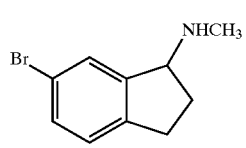

104A

To a solution of 6-bromoindanol (0.65 g, 3.02 mmol) in toluene (10 mL) was added thionyl chloride (0.34 mL, 4.53 mmol) and the contents heated at 50° C. for one hour. The reaction mixture was cooled to room temperature and partitioned between dichloromethane (20 mL) and water (20 mL). The dichlromethane layer was dried over sodium sulfate and concentrated under reduced pressure to yield a liquid (0.63 g) which was used as such for the subsequent step without further purification.

To 6-bromo-1-chloroindane obtained in the previous step was added methylamine (6 mL of a 33% solution in ethanol) and the contents heated in a sealed tube at 90° C. for eighteen hours. The reaction mixture was concentrated under reduced pressure and purified by silica gel flash chromatography using dichloromethane/methanol to yield the title compound (0.251 g, 37%). $^1$H NMR (CDCl$_3$): □ 7.45 (s, 1H), 7.25 (d, 1H), 7.0 (d, 1H), 4.1 (t, 1H), 2.9 (m, 1H), 2.7 (m, 1H), 2.5 (brs, 1H), 2.4 (s, 3H), 2.3 (m, 1H), 1.8 (m, 1H).

Example 104, Part B (6-Bromo-2,3-dihydro-1H-inden-1-yl)methylcarbamic acid phenylmethyl ester

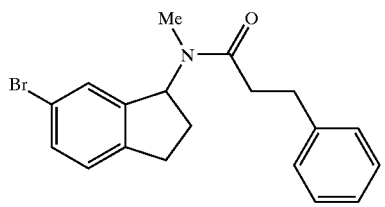

104B

To a solution of 104A (0.251 g, 1.11 mmol) in dioxane/water (10:5 mL) was added sodium carbonate (0.294 g, 2.77 mmol) followed by benzyloxycarbonyl chloride (0.19 mL, 1.33 mmol) at room temperature. The reaction mixture was stirred at room temperature for one hour and partitioned between ethyl acetate (2×20 mL) and water (20 mL). The ethyl acetate layer is dried over sodium sulfate and concentrated under reduced pressure to yield the title compound (0.392 g, 98%). $^1$H NMR (CDCl$_3$, mixture of rotomers): □ (7.3 m, 7H), 7.0 (m, 1H), 5.8, 5.7 (t, 1H), 5.1 (s, 2H), 2.9 (s, 1H), 2.8 (s, 1H), 2.6, 2.55 (s, 3H), 2.3 (m, 1H), 1.9 (m, 1H).

Example 104, Part C

[2,3-Dihydro-6-[(trimethylsilyl)ethynyl]-1H-inden-1-yl]methylcarbamic acid phenylmethyl ester

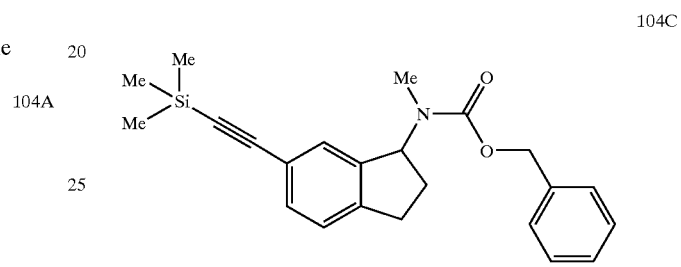

104C

A mixture of 104B (0.392 g, 1.08 mmol), (trimethylsilyl)acetylene (0.18 mL, 1.3 mmol), bis(triphenylphosphine)palladium(II) chloride (0.030 g, 0.04 mmol), copper(I) iodide (0.016 g, 0.08 mmol) and triethylamine (0.33 mL, 2.4 mmol) in toluene was heated to 80° C. for 2 hrs. The reaction mixture was filtered over celite. The filtrate was concentrated under reduced pressure and purified by silica gel flash chromatography employing dichloromethane/methanol to give the title compound (0.375 g, 91%). LC-MS: Column A, retention time=4.5 minutes, m/z 378.17 (M+H)$^+$.

Example 104, Part D (6-Ethynyl-2,3-dihydro-1H-inden-1-yl)methylcarbamic acid phenylmethyl ester

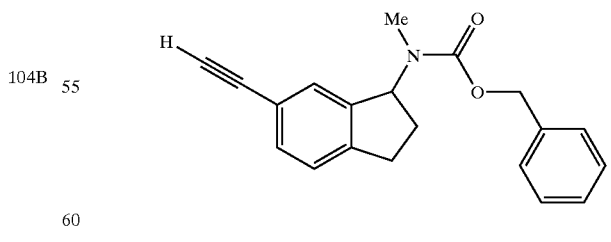

Compound 104C (0.375 g, 0.99 mmol) was subjected to the same conditions as outlined in C2 (example 4) to yield the title compound (0.285 g, 94%). LC-MS: Column A, retention time=3.86 minutes, m/z 306.14 (M+H)$^+$.

Example 104, Part F

[6-[1,4-Dihydro-7-methoxy-6-(5-oxazolyl)-4-oxo-2-quinolinyl]-2,3-dihydro-1H-inden-1-yl]methylcarbamic acid phenylmethyl ester

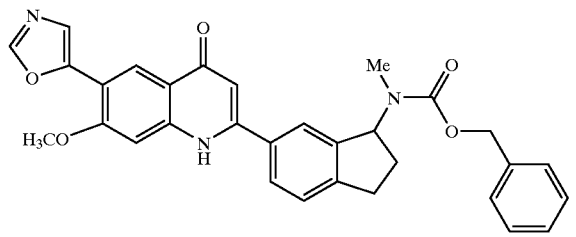

Compound 104D (0.285 g, 0.94 mmol) was subjected to the same conditions as outlined in C2 (example 4) to yield the title compound (0.145 g, 94%). LC-MS: Column C, retention time=3.45 minutes, m/z 522.26 (M+H)$^+$.

EXAMPLE 105

2-[2,3-Dihydro-3-(methylamino)-1H-inden-5-yl]-7-methoxy-6-(5-oxazolyl)-4(1H)-quinolinone

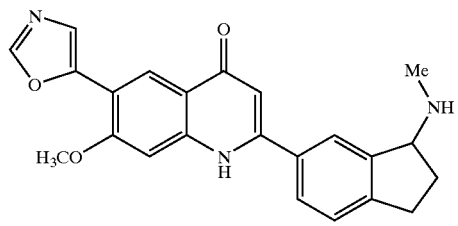

To 104 (0.14 g, 0.26 mmol) in 20 mL of methanol was added 10% Palladium on carbon (0.09 g) and the contents hydrogenated at 40 psi for six hours. The reaction mixture was filtered and the filtrate concentrated to yield the title compound (0.063 g, 61%). LC-MS: Column A, retention time=2.46 minutes, m/z 388.12 (M+H)$^+$.

EXAMPLE 106

2-[2,3-Dihydro-3-(1-pyrrolidinyl)-1H-inden-5-yl]-7-methoxy-6-(5-oxazolyl)-4(1H)-quinolinone

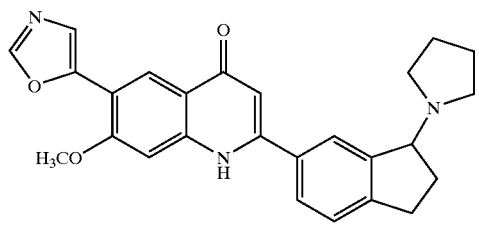

Example 106, Part A 1-(6-Bromo-2,3-dihydro-1H-inden-1-yl)pyrrolidine

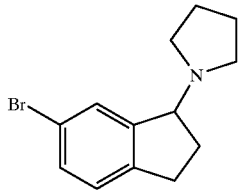

6-bromoindanol (0.3 g, 1.39 mmol) was subjected to the same conditions as 104, part A by substituting methylamine with pyrrolidine (1.16 mL, 14 mmol) to yield the title compound (0.195 g, 52%). $^1$H NMR (CDCl$_3$): 7.4 (s, 1H), 7.25 (d, 1H), 7.0 (d, 1H), 4.1 (t, 1H), 2.9 (m, 1H), 2.6 (m, 1H), 2.55 (m, 4H), 2.1 (m, 2H), 1.7 (brs, 4H).

Example 106 Part B 1-(6-Ethynyl-2,3-dihydro-1H-inden-1-yl)pyrrolidine

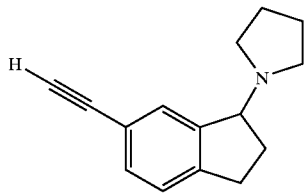

Compound 106A (0.195 g, 0.73 mmol) was subjected to the same conditions as 104, part B and C to yield the title compound (0.130 g, 84%). LC-MS: Column A, retention time=1.85 minutes, m/z 212.17 (M+H)$^+$.

Example 106, Part C

2-[2,3-Dihydro-3-(1-pyrrolidinyl)-1H-inden-5-yl]-7-methoxy-6-(5-oxazolyl)-4(1H)-quinolinone

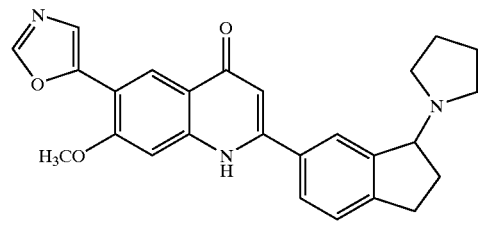

Compound B (0.13 g, 0.63 mmol) was subjected to the same conditions as outlined in C2 (example 4) to yield the title compound (0.007 g). LC-MS: Column C, retention time=2.36 minutes, m/z 428.24 (M+H)$^+$.

EXAMPLE 107

2-[2,3-Dihydro-3-(4-morpholinyl)-1H-inden-5-yl]-7-methoxy-6-(5-oxazolyl)-4(1H)-quinolinone

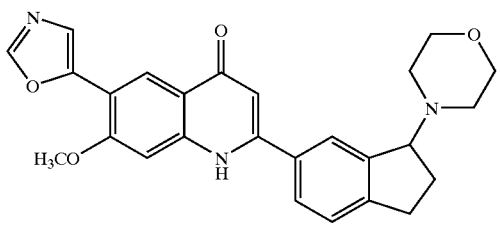

Example 107, Part A 1-(6-Bromo-2,3-dihydro-1H-inden-1-yl)morpholine

107A

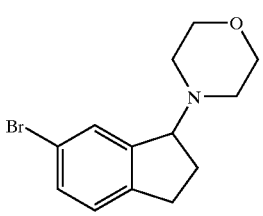

6-bromoindanol (0.3 g, 1.39 mmol) was subjected to the same conditions as 104, part A by substituting methylamine with morpholine (4.0 mL) in toluene (5 mL) to yield the title compound (0.35 g, 89%). $^1$H NMR (CDCl$_3$): 7.5 (s, 1H), 7.3 (d, 1H), 7.0 (d, 1H), 4.2 (t, 1H), 3.7 (brs, 4H), 2.8 (m, 1H), 2.7 (m, 1H), 2.4 (m, 4H), 2.1 (m, 2H).

Example 107, Part B 4-(6-Ethynyl-2,3-dihydro-1H-inden-1-yl)morpholine

107B

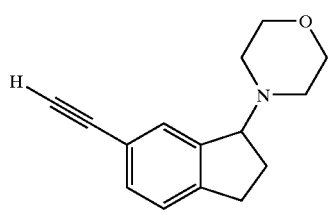

Compound 107A (0.35 g, 1.24 mmol) was subjected to the same conditions as 104, part B and C to yield the title compound (0.243 g, 86%). LC-MS: Column A, retention time=1.73 minutes, m/z 228.14 (M+H)$^+$.

Example 107, Part C

2-[2,3-Dihydro-3-(4-morpholinyl)-1H-inden-5-yl]-7-methoxy-6-(5-oxazolyl)-4(1H)-quinolinone

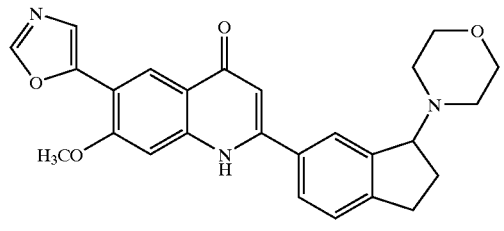

Compound 104B (0.233 g, 1.04 mmol) was subjected to the same conditions as outlined in C2 (example 4) to yield the title compound (0.045 g). LC-MS: Column C, retention time=2.34 minutes, m/z 444.25 (M+H)$^+$.

EXAMPLE 108

2-[3-(1-Azetidinyl)-2,3-dihydro-1H-inden-5-yl]-7-methoxy-6-(5-oxazolyl)-4(1H)-quinolinone

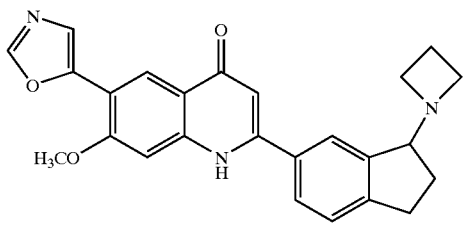

6-bromoindanol (0.3 g, 1.39 mmol) was subjected to the same conditions as 104, part A by substituting methylamine with azetidine (0.9 mL 13.9 mmol) in toluene (5 mL) to yield the title compound (0.167 g, 47%). $^1$H NMR (CDCl$_3$) 7.3 (s, 1H), 7.2 (d, 1H), 7.0 (d, 1H), 3.8 (m, 1H), 3.2 (m, 4H), 3.0 (m, 1H), 2.8 (m, 1H), 2.0 (m, 3H), 1.8 (m, 1H).

Example 108, Part B 1-(6-Ethynyl-2,3-dihydro-1H-inden-1-yl)azetidine

108B

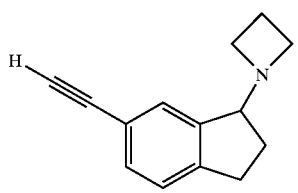

Compound 108A (0.167 g, 0.66 mmol) was subjected to the same conditions as 104, part B and C to yield the title compound (0.075 g, 57%). LC-MS: Column A, retention time=1.67 minutes, m/z 198.11 (M+H)$^+$.

Example 108, Part C

2-[3-(1-Azetidinyl)-2,3-dihydro-1H-inden-5-yl]-7-methoxy-6-(5-oxazolyl)-4(1H)-quinolinone

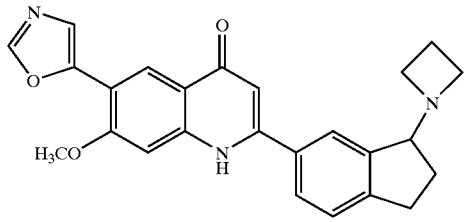

Compound 108B (0.0.075 g, 0.391 mmol) was subjected to the same conditions as outlined in C2 (example 4) to yield the title compound (0.015 g). LC-MS: Column C, retention time=2.32 minutes, m/z 414.26 (M+H)+.

EXAMPLE 109

7-Methoxy-2-[(3-methylphenyl)methyl]-6-(5-oxazolyl)-4(1H)-quinolinone

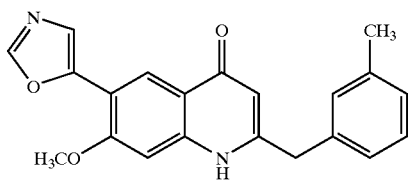

Example 109, Part A

3-Methyl-b-oxobenzenebutanoic acid ethyl ester

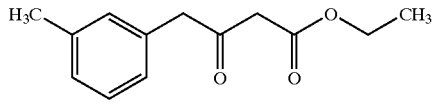

m-tolylacetic acid (2.0 g, 13.33 mmol) was subjected to the same conditions as outlined in method A3 (example 3) to yield the title compound (2.7 g, 92%). 1H NMR (CDCl3): □ 7.25 (m, 1H), 7.1 (d, 1H), 7.0 (m, 2H), 4.2 (q, 2H), 3.8 (s, 2H), 3.4 (s, 2H), 2.4 (s, 3H), 1.2 (t, 3H).

Example 109, Part B

3-[[3-Methoxy-4-(5-oxazolyl)phenyl]amino]-4-(3-methylphenyl)-2-propenoic acid ethyl ester

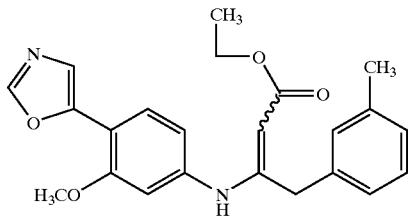

Compound 109A (1.0 g, 4.54 mmol) was subjected to the same conditions as outlined in method A3 (example 3) to yield the title compound (1.2 g, 67%).

Example 109, Part C

7-Methoxy-2-[(3-methylphenyl)methyl]-6-(5-oxazolyl)-4(1H)-quinolinone

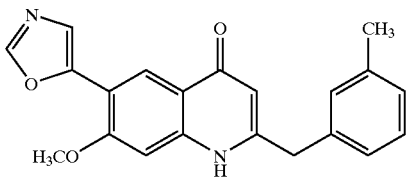

Compound 109B (0.075 g, 0.391 mmol) was subjected to the same conditions as outlined in A3 (example 4) to yield the title compound (0.6 g, 68%). LC-MS: Column A, retention time=3.21 minutes, m/z 347.05 (M+H)+.

EXAMPLE 110

2-(2,3-Dihydro-3-methoxy-1H-inden-5-yl)-7-methoxy-6-(5-oxazolyl)-4(1H)-quinolinone

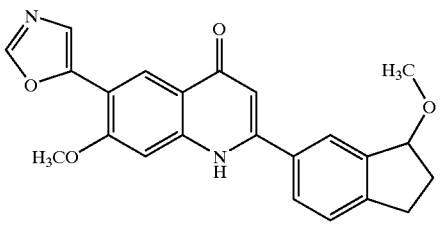

Example 110, Part A

6-Bromo-2,3-dihydro-1-methoxy-1H-indene

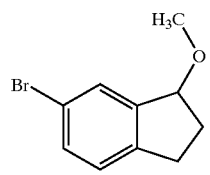

110A

To a solution of 6-bromoindanol (0.51 g, 2.4 mmol) in anhydrous tetrahydrofuran (10 mL), was added sodium hydride (0.097 g, 3.84 mmol) over a period of five minutes at room temperature. The reaction mixture was stirred at room temperature for fifteen minutes and iodomethane (0.22 mL, 3.6 mmol) was added. After thirty minutes at room temperature, the reaction mixture was partitioned between ethyl acetate (20 mL) and water (20 mL). The ethyl acetate layer was washed with brine (20 mL), dried over sodium sulfate and concentrated to yield the title compound (0.485 g, 89%). 1H NMR (CDCl3) : □ 7.5 (s, 1H), 7.3 (d, 1H), 7.0 (d, 1H), 4.7 (m, 1H), 3.3 (s, 3H), 3.0 (m, 1H), 2.7 (m, 1H), 2.3 (m, 1H), 2.0 (m, 1H).

Example 110, Part B

6-Ethynyl-2,3-dihydro-1-methoxy-1H-indene

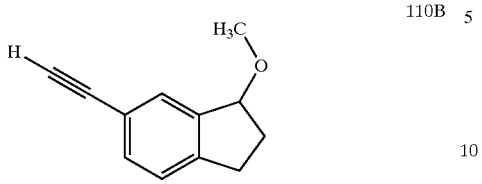

110B

Compound 110A (0.485 g, 2.14 mmol) was subjected to the same conditions as 104, part B and C to yield the title compound (0.35 g, 95%). ¹H NMR (CDCl₃): □ 7.5 (s, 1H), 7.3 (d, 1H), 7.0 (d, 1H), 4.7 (m, 1H), 3.3 (s, 3H), 3.0 (m, 1H), 2.9 (s, 1H), 2.7 (m, 1H), 2.3 (m, 1H), 2.0 (m, 1H).

Example 110, Part C 2-(2,3-Dihydro-3-methoxy-1H-inden-5-yl)-7-methoxy-6-(5-oxazolyl)-4(1H)-quinolinone

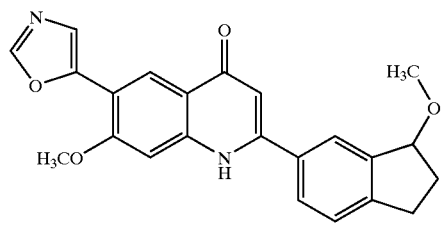

Compound 110B (0.163 g, 0.94 mmol) was subjected to the same conditions as outlined in C2 (example 4) to yield the title compound (0.05 g, 27%). LC-MS: Column A, retention time=3.17 minutes, m/z 389.11 (M+H)⁺.

EXAMPLE 111

2-(2,3-Dihydro-1-methyl-1H-isoindol-5-yl)-7-methoxy-6-(5-oxazolyl)-4(1H)-quinolinone

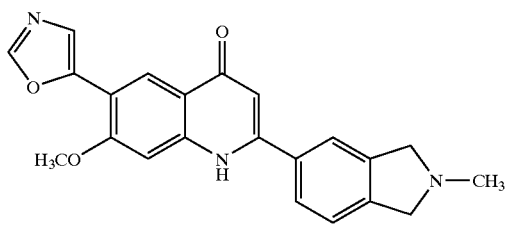

Example 111, Part A

6-Ethynyl-2,3-dihydro-2-methyl-1H-isoindole

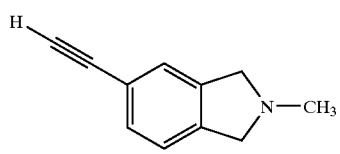

111A 5-bromo-2-(N-methyl)isoindoline (prepared in a similar manner to 5-bromoisoindoline, as reported in EP0343560)

(0.1.1 g, 5.18 mmol) was subjected to the same conditions as 104, part B and C to yield the title compound (0.298 g, 22%). LC-MS: Column A, retention time=1.05 minutes, m/z 158.04 (M+H)⁺.

Example 111, Part B 2-(2,3-Dihydro-1-methyl-1H-isoindol-5-yl)-7-methoxy-6-(5-oxazolyl)-4(1H)-quinolinone

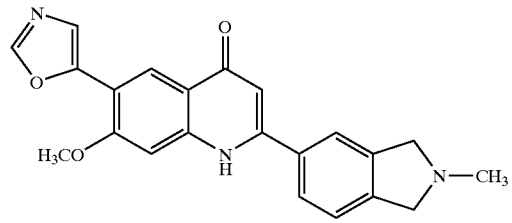

111B

Compound □□□□(0.298 g) was subjected to the same conditions as outlined in C2 (example 4) to yield the title compound (0.05 g ). LC-MS: Column A, retention time= 2.18 minutes, m/z 374.16 (M+H)⁺.

EXAMPLE 112

7-Methoxy-2-[3-[(4-methoxyphenyl)methoxy]phenyl]-6-(5-oxazolyl)-4(1H)-quinolinone

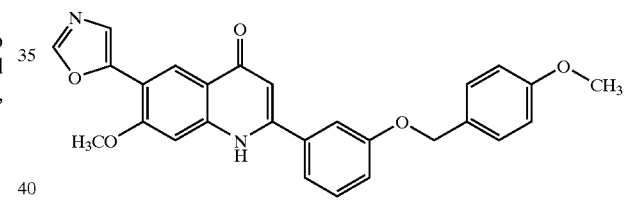

Example 112, Part A

3-[(4-Methoxyphenyl)methoxy]benzoic acid methyl ester

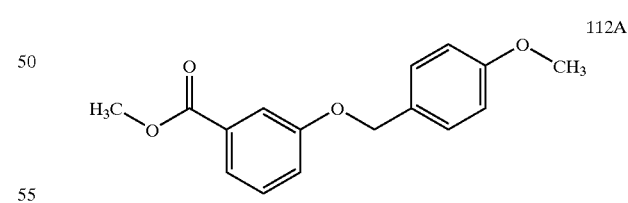

112A

To a solution of methyl-3-hydroxybenzoate (5.0 g, 32.8 mmol) in acetone (30 mL) was added potassium carbonate (6.82 g, 49.2 mmol) and p-methoxybenzyl chloride (4.5 mL, 32.8 mmol). The contents are heated under reflux for forty eight hours, concentrated under pressure and partitioned between ethyl acetate (100 mL) and water (100 mL). The ethyl acetate layer was dried over sodium sulfate and concentrated to yield the title compound (8.87 g, 99%). ¹H NMR (CDCl₃): □ 7.8 (m, 2H), 7.4 (m, 3H), 7.15 (m, 1H), 6.9 (d, 2H), 5.1 (s, 2H), 3.9 (s, 3H), 3.8 (s, 3H).

Example 112, Part B

3-[(4-Methoxyphenyl)methoxy]benzoic acid

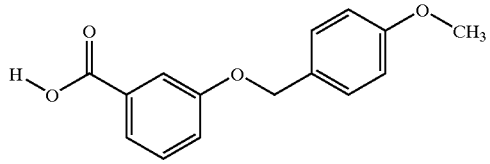

To compound 112A (8.87 g, 32.61 mmol) in a mixture of dioxane and water (15:10 mL) was added lithium hydroxide (2.73 g, 65.22 mmol) and the contents heated under reflux for two hours. The reaction mixture was concentrated and partitioned between ethyl acetate (2×300 mL) and water (600 mL). The aqueous layer was made acidic using 1N hydrochloric acid (aqueous) and extracted into ethyl acetate (2×300 mL). The ethyl acetate layer was dried over sodium sulfate and concentrated to yield the title compound (8.2 g, 97%). $^1$H NMR (DMSO-d6): ☐ 11.0 (s, 1H), 7.6 (m, 2H), 7.4 (m, 3H), 7.2 (m, 1H), 6.9 (d, 2H), 5.1 (s, 2H), 3.9 (s, 3H), 3.8 (s, 3H).

Example 112, Part C

3-[(4-Methoxyphenyl)methoxyl-b-oxobenzenepropanoic acid ethyl ester

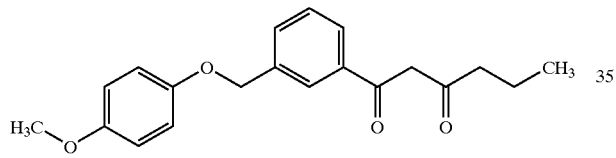

Compound 112B (8.1 g, 31.39 mmol) was subjected to the same conditions as outlined in method A3 (example 3) to yield the title compound (9.8 g, 95%). $^1$H NMR (CDCl$_3$): ☐ 7.6 (brs, 1H), 7.5 (d, 1H), 7.4 (m, 3H), 7.2 (m,1H), 6.9 (d, 2H), 5.0 (s, 2H), 4.2 (q, 2H), 3.9 (s, 2H), 3.8 (s, 3H), 1.2 (t, 3H).

Example 112, Part D

3-[[3-Methoxy-4-(5-oxazolyl)phenyl]amino]-3-[3-[(4-methoxyphenyl)methoxy]phenyl]-2-propenoic acid ethyl ester

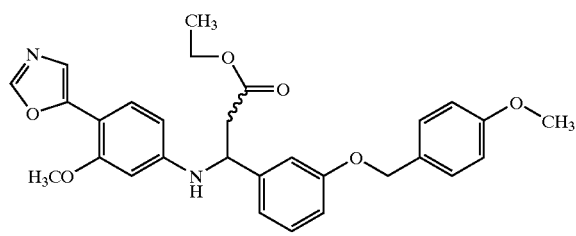

Compound 112C (5.0 g, 15.24 mmol) was subjected to the same conditions as outlined in method A3 (example 3) to yield the title compound (5.5 g, 72%).

Example 112, Part E

7-Methoxy-2-[3-[(4-methoxyphenyl)methoxy]phenyl]-6-(5-oxazolyl)-4(1H)-quinolinone

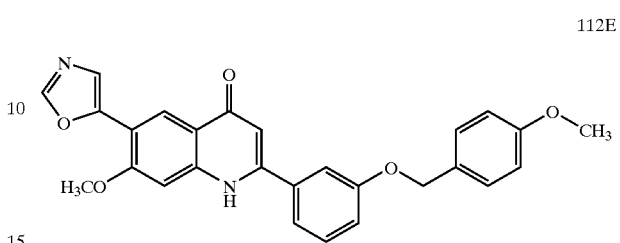

Compound 112D (5.3 g, 10.6 mmol) was subjected to the same conditions as outlined in A3 (example 4) to yield the title compound (2.8 g, 58%). LC-MS: Column A, retention time=3.54 minutes, m/z 455.10 (M+H)$^+$.

EXAMPLE 113

2-(3-Hydroxyphenyl)-7-methoxy-6-(5-oxazolyl)-4(1H)-quinolinone

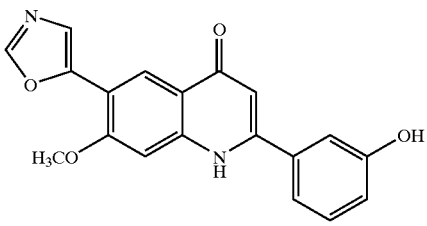

To compound 112 (0.2 g, 0.44 mmol) was added trifluoroacetic acid (2 mL) and the contents stirred at room temperature for thirty minutes. The reaction mixture was concentrated and azeotroped twice with toluene. To the residue was added a mixture of methanol and ether (7:3 mL) and the solid that separates out is filtered and dried to yield the title compound (0.14 g, 95%). LC-MS: Column A, retention time=2.8 minutes, m/z 335.10 (M+H)$^+$.

EXAMPLE 114

2-[3-[2-(Dimethylamino)ethoxy]phenyl]-7-methoxy-6-(5-oxazolyl)-4(1H)-quinolinone

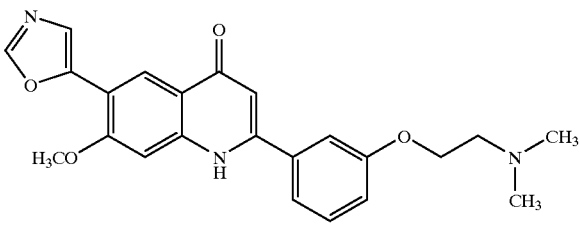

Example 114, Part A

7-Methoxy-2-[3-[(4-methoxyphenyl)methoxy]phenyl]-6-(5-oxazolyl)-4-(phenylmethoxy)quinoline

114A

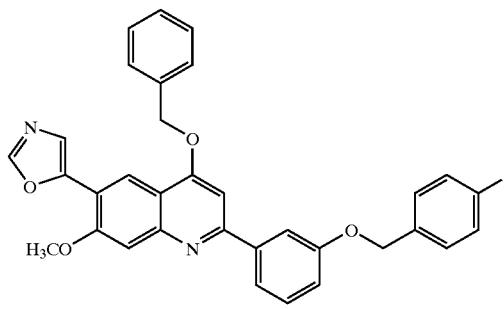

To a solution of compound 112 (0.4 g, 0.88 mmol) in anhydrous dimethylformamide (10 mL) was added sodium hydride (0.027 g, 1.056 mmol) over a two minute period. The reaction mixture was heated for ten minutes at 80° C. followed by the addition of benzyl bromide (0.13 mL, 1.056 mmol) at that temperature. The reaction mixture was heated for a further ten minutes and concentrated under reduced pressure. To the residue was added water (20 mL) and the solid that separates out is filtered and dried to yield the title compound (0.475 g, 99%). LC-MS: Column A, retention time=3.69 minutes, m/z 545.12 (M+H)$^+$.

Example 114, Part B

3-(7-Methoxy-6-(5-oxazolyl)-4-(phenylmethoxy)-2-quinolinyl]phenol

114B

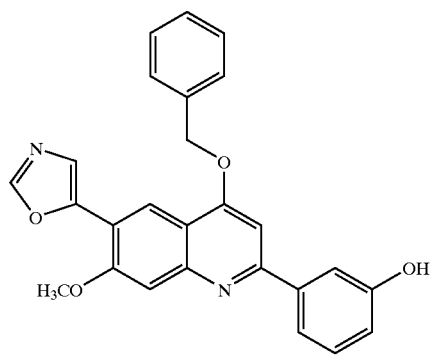

To compound 114A obtained above (0.475 g, 0.87 mmol) was added trifluoroacetic acid (6 mL) and the contents stirred at room temperature for forty minutes. The reaction mixture was concentrated and made basic by the slow addition of saturated aqueous sodium bicarbonate. The solid that separates out was extracted into ethyl acetate (110 mL), dried over sodium sulfate and concentrated to yield the title compound (0.36 g, 97%). LC-MS: Column A, retention time=3.24 minutes, m/z 425.08 (M+H)$^+$.

Example 114, Part C

2-[3-[7-Methoxy-6-(5-oxazolyl)-4-(phenylmethoxy)-2-quinolinyl]phenoxy]-N,N-dimethylethanamine

114C

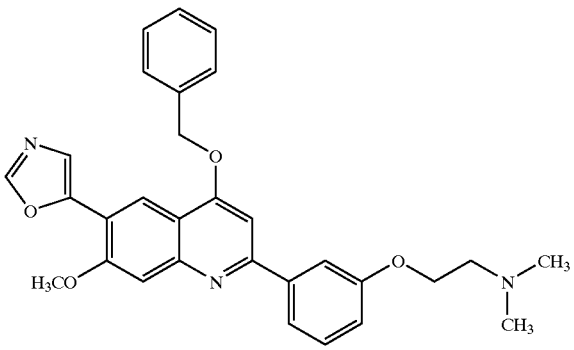

To a solution of compound 114B (0.275 g, 0.65 mmol) in anhydrous dimethyformamide (10 mL) was added potassium carbonate (0.134 g, 0.975 mmol) and the contents heated to 80° C. for two minutes. 1-chloro-2-dimethylaminoethane (0.78 mL, 0.78 mmol of a 1.0M solution in chlorobenzene) was added and the contents heated at 80° C. for two hours. Additional potassium carbonate (2×0.134 g) and 1-chloro-2-dimethylaminoethane (2×0.78 mL, 0.78 mmol of a 1.0M solution in chlorobenzene) was added in one hour intervals at 80° C. The reaction mixture was concentrated and partitoned between dichloromethane (20 mL) and water (20 mL). The dichloromethane layer was dried over sodium sulfate, concentrated and column purified using silica gel flash column chromatography (dichloromethane/methanol as eluent) to yield the title compound (0.155 g, 48%). LC-MS: Column C, retention time=2.74 minutes, m/z 496.22 (M+H)$^+$.

Example 114, Part D

2-[3-[2-(Dimethylamino)ethoxy]phenyl]-7-methoxy-6-(5-oxazolyl)-4(1H)-quinolinone

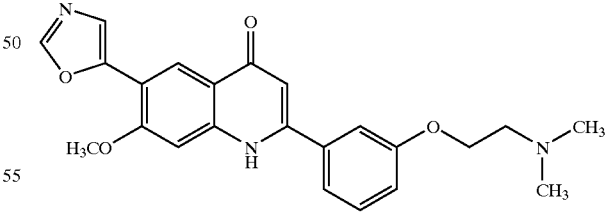

To a solution of compound 114C in methanol (0.155 g, 0.31 mmol) was added 10% palladium on carbon (0.07 g) and the contents hydrogenated at 20 psi for two hours. The reaction mixture was filtered and the filter pad washed with methanol (3×10 mL). The filtrate was concentrated under reduced pressure to yield the title compound (0.119 g, 94%). LC-MS: Column A, retention time=2.23 minutes, m/z 406.37 (M+H)$^+$.

EXAMPLE 115

7-Methoxy-2-[3-(2-(4-morpholinyl)ethoxylphenyl]-6-(5-oxazolyl)-4(1H)-quinolinone

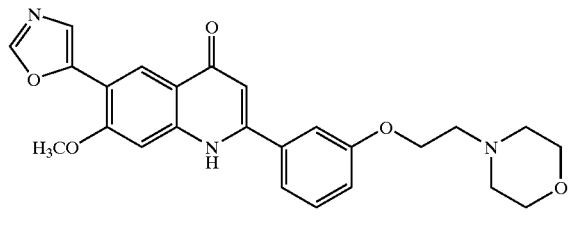

The title compound was made in a manner similar to 114 employing 2-chloroethylmorpholine in place of 1-chloro-2dimethylaminoethane in step C. LC-MS: Column A, retention time=2.29 minutes, m/z 448 (M+H)$^+$.

EXAMPLE 116

6-Methoxy-7-(5-oxazolyl)-3-phenyl-2H-1,4-benzothiazine 1,1-dioxide

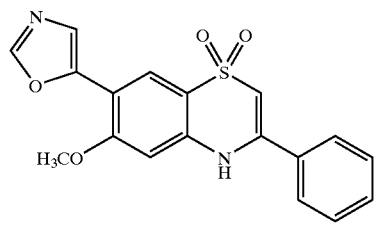

Example 116, Part A

[[2-Amino-4-methoxy-5-(5-oxazolyl)phenyl] thio]carbonitrile

116A

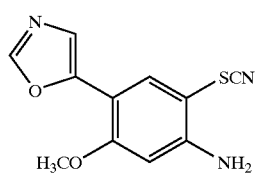

To a solution of 1D (2.0 g, 10.52 mmol) in methanol (20 mL) was added ammonium thiocyanate (1.6 g, 21.04 mmol). The contents were cooled to −5° C. and bromine (0.34 mL, 6.62 mmol) was added dropwise. The reaction mixture was stirred at −5° C. for 10 minutes and at room temperature for twenty minutes. The solid that separates out was washed with water (2×20 mL), ethanol (2×10 mL) and dried to yield the title compound (1.4 g, 54%). $^1$H NMR (DMSO-d6): 8.32 (s, 1H), 7.67 (s, 1H), 7.28 (s, 1H), 6.56 (s, 1H), 6.3 (brs, 2H), 3.88 (s, 3H).

Example 116, Part B

N-[5-Methoxy-4-(5-oxazolyl)-2-(thiocyanato)phenyl]acetamide

116B

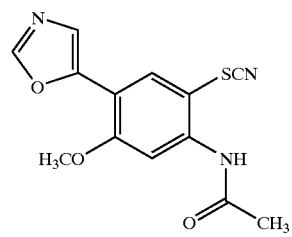

To a solution of 116A (0.4 g, 1.62 mmol) in dichloromethane (10 mL) was added triethylamine (0.22 mL, 1.62 mmol) and the contents cooled to 0° C. Acetyl chloride (0.11 mL, 1.62 mmol) was added and the contents stirred at room temperature for one hour. The reaction mixture was filtered and the solid washed with dichloromethane (2×10 mL) and dried to yield the title compound (0.436 g, 93%). LC-MS: Column A, retention time=2.06 minutes, m/z 290.3 (M+H)$^+$.

Example 116, Part C

N-[5-Methoxy-4-(5-oxazolyl)-2-[(2-oxo-2-phenylethyl)thio]phenyl]acetamide

116C

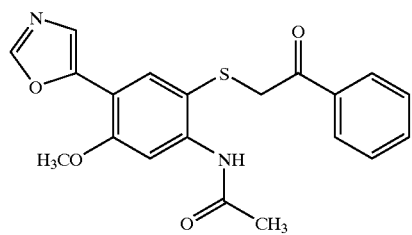

To a solution of 116B (0.396 g, 1.37 mmol) in a mixture of ethanol and dimethylformamide (10:3 mL), at 0° C. was added sodium borohydride (0.104 g, 2.74 mmol) in one lot. After five minutes, acetone (5 mL) was added and the reaction mixture stirred at room temperature for one minute. 2-bromoacetophenone (0.272 g, 1.37 mmol) was added in one lot and the contents stirred at room temperature for forty five minutes. The reaction mixture was concentrated under reduced pressure. To the residue that is obtained was added ethyl acetate (10 mL). The solid that is thrown out (0.035 g) was filtered and dried to yield the title compound. The filtrate was concentrated and subjected to silica gel flash column chromatography (dichloromethane/ethyl acetate as eluent) to yield another batch of the title compound (combined yield: 0.120 g, 23%). LC-MS: Column A, retention time=3.14 minutes, m/z 383.08 (M+H)$^+$.

Example 116, Part D

N-[5-Methoxy-4-(5-oxazolyl)-2-[(2-oxo-2-phenylethyl)sulfonyl]phenyl]acetamide

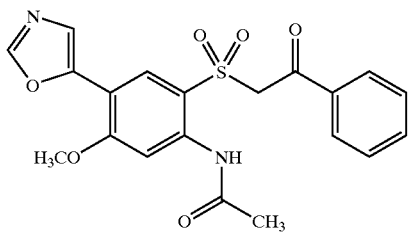

116D

To a solution of 116C (0.12 g, 0.31 mmol) in acetic acid (5 mL) was added a few crystals of sodium tungstate followed by hydrogen peroxide (30% aqueous solution, 0.1 mL, 0.93 mmol) at room temperature. The raction mixture was stirred at room temperature for eighteen hours and the solid that is thrown out was filtered, washed with water and dried to yield the title compound (0.105 g, 81%). LC-MS: Column A, retention time=2.96 minutes, m/z 415.03 (M+H)+.

Example 116, Part E

6-Methoxy-7-(5-oxazolyl)-3-phenyl-2H-1,4-benzothiazine 1,1-dioxide

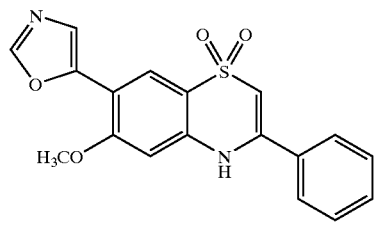

A solution of 116D (0.105 g, 0.25 mmol) in 4N aqueous hydrochloric acid (3 mL) was heated at 110° C. for one hour. The reaction mixture was cooled to room temperature and the solid that separates out was filtered, washed with water (3×10 mL) and dried to yield the title compound (0.055 g, 61%). LC-MS: Column A, retention time=2.94 minutes, m/z 355.07 (M+H)+.

EXAMPLE 117

6-Methoxy-3-(4-methoxyphenyl)-7-(5-oxazolyl)-2H-1,4-benzothiazine 1,1-dioxide

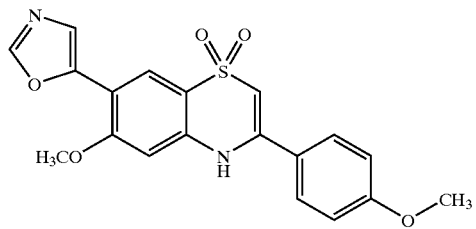

The title compound was made in a manner similar to 116 employing 2-bromo-4'methoxyacetophenone in place of 2bromoacetophenone in step 116C. LC-MS: Column A, retention time=3.09 minutes, m/z 384.97 (M+H)+.

EXAMPLE 118

3-Hydroxy-7-methoxy-6-(5-oxazolyl)-2-phenyl-4(1H)-quinolinone

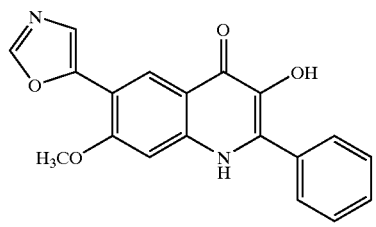

Example 118, Part A

2-Amino-4-methoxy-5-(5-oxazolyl)benzoic acid methyl ester

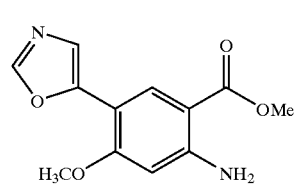

118A

A steel bomb was charged with iodo aniline (1.18 g, 3.73 mmol) DMF (15 ml) bis(triphenylphosphine)palladium(II) dichloride (135 mg, 0.19 mmol), triethylamine (1.56 ml, 11.4 mmol), and methanol (20 ml). The reaction mixture was heated at 120° C. under a carbon monoxide atmosphere for eighteen hours, cooled to room temperature, concentrated under reduced pressure and purified by silica gel flash column chromatography employing ethyl acetate/hexane (2:3) to yield the title compound (706 mg, 76%). $^1$H NMR (CDCl$_3$) δ 3.81 (s, 3H), 3.86 (s, 3H), 6.10 (s, 1H), 7.37 (s, 1H), 7.80 (s, 1H), 8.20 (s, 1H).

Example 118, Part B

2-Amino-4-methoxy-5-(5-oxazolyl)benzoic acid

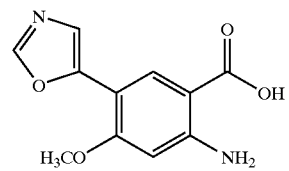

To the methyl ester (706 mg, 2.85 mmol) was added lithium hydroxide (251 mg, 5.97 mmol), water (5 ml) THF (20 ml) and MeOH (20 ml). The reaction mixture was heated under reflux for eighteen hours and concentrated under reduced pressure. The pH of the reaction was adjusted to 4–5 employing 1 N HCl. The solid that separates out was filtered rinsed with water and dried to yield the title compound (630 mg, 94%). $^1$H NMR (DMSO) δ 3.89 (s, 3H), 6.45 (s, 1H), 7.0 (br, 2H), 7.26 (s, 1H), 8.06 (s, 1H), 8.29 (s, 1H), 12.0 (broad, 1H).

118B

Example 118, Part C

2-Amino-4-methoxy-5-(5-oxazolyl)benzoic acid 2-oxo-2-phenylethyl ester

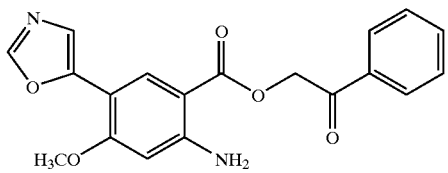

118C

To a solution of acid 118B (0.279 g, 1.19 mmol) in acetone (10 ml) was added potassium carbonate (0.215 g, 1.19 mmol) and the contents stirred at room temperature for 30 min. Then 2-bromoacetophenone (0.236 g, 1.19 mmol) was added and the reaction mixture was heated under reflux for eighteen hours. The reaction mixture was concentrated under reduced pressure and partitioned between dichloromethane (20 mL) and water (20 mL). The dichloromethane layer was dried over sodium sulfate and concentrated under reduced pressure to yield the title compound (0.410 g, 97%). LC-MS: Column A, retention time=3.25 minutes, m/z 353.09 (M+H)+.

Example 118, Part C

3-Hydroxy-7-methoxy-6-(5-oxazolyl)-2-phenyl-4(1H)-quinolinone

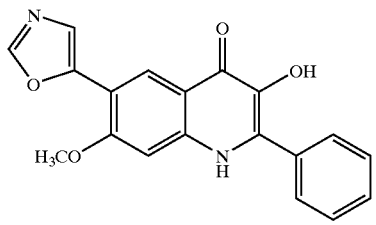

To phosphorous pentoxide (0.073 g, 0.51 mmol) in 1,2-dichlorobenzene (2 mL) was added hexamethyldisiloxane (0.43 mL, 2.04 mmol) and the contents heated at 150° C. for thirty minutes. To the clear solution was added 118B (0.06 g, 0.17 mmol) and the contents heated at 150° C. for 2.5 hours. The reaction mixture was cooled to room temperature and filtered. The solid is washed with ethyl acetate (5×10 mL), water (10 mL), saturated aqueous sodium bicarbonate (10 mL), water (10 mL) and dried to yield the title compound (0.035 g, 61%). LC-MS: Column A, retention time= 2.88 minutes, m/z 335.38 (M+H)+.

EXAMPLE 119

3-Hydroxy-7-methoxy-2-(2-methylphenyl)-6-(5-oxazolyl)-4(1H)-quinolinone

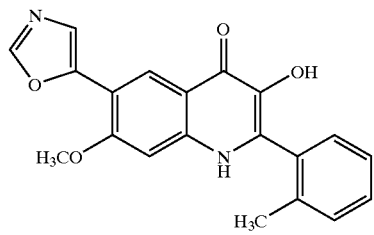

The title compound was made in a manner similar to 118 employing 2-bromo-2'methylacetophenone in place of 2-bromoacetophenone in step 118A. LC-MS: Column C, retention time=2.82 minutes, m/z 349.12 (M+H)+.

EXAMPLE 120

3-Hydroxy-7-methoxy-2-(3-methylphenyl)-6-(5-oxazolyl)-4(1H)-quinolinone

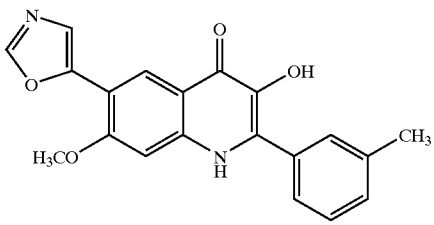

The title compound was made in a manner similar to 118 employing 2-bromo-3'methylacetophenone in place of 2-bromoacetophenone in step 118A. LC-MS: Column A, retention time=3.04 minutes, m/z 349.18 (M+H)+.

EXAMPLE 121

3-Hydroxy-7-methoxy-2-(4-methylphenyl)-6-(5-oxazolyl)-4(1H)-quinolinone

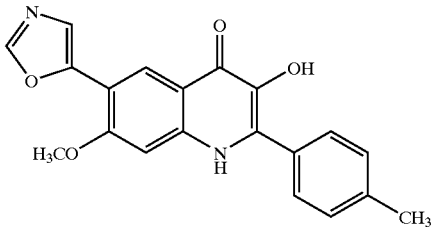

The title compound was made in a manner similar to 118 employing 2-bromo-4'methylacetophenone in place of 2-bromoacetophenone in step 118A. LC-MS: Column A, retention time=3.13 minutes, m/z 349.37 (M+H)+.

EXAMPLE 122

2-(3,4-Dimethylphenyl)-3-hydroxy-7-methoxy-6-(5-oxazolyl)-4(1H)-quinolinone

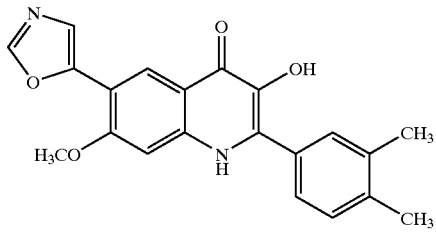

The title compound was made in a manner similar to 118 employing 2-bromo-3',4'methylacetophenone in place of 2-bromoacetophenone in step 118A. LC-MS: Column A, retention time=3.26 minutes, m/z 363.18 (M+H)$^+$.

EXAMPLE 123

3-Hydroxy-7-methoxy-2-(4-methoxyphenyl)-6-(5-oxazolyl)-4(1H)-quinolinone

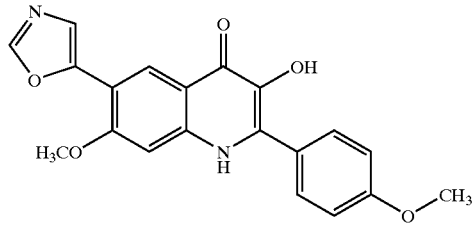

The title compound was made in a manner similar to 118 employing 2-bromo-4'methoxyacetophenone in place of 2-bromoacetophenone in step 118A. LC-MS: Column A, retention time=2.89 minutes, m/z 365.13 (M+H)$^+$.

EXAMPLE 124

2-(4-Chloro-3-methylphenyl)-3-hydroxy-7-methoxy-6-(5-oxazolyl)-4(1H)-quinolinone

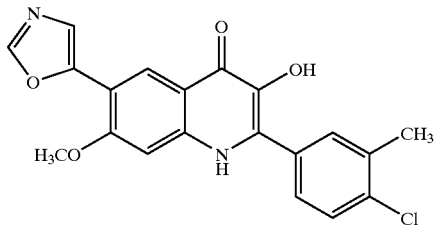

Example 124, Part A

2-Amino-4-methoxy-5-(5-oxazolyl)benzoic acid 2-(4-chloro-3-methylphenyl)-2-oxoethyl ester

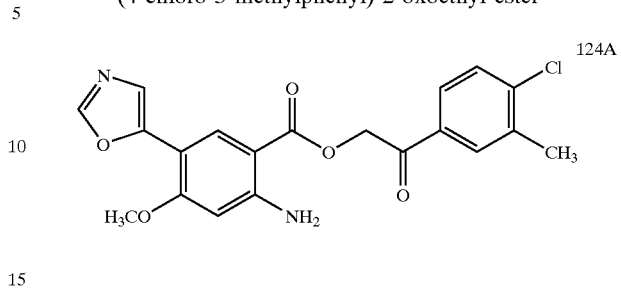

The title compound was made in a manner similar to 118 employing 2-bromo-4'chloro-3'methylacetophenone in place of 2-bromoacetophenone in step 118A.

Example 124, Part B 2-(4-Chloro-3-methylphenyl)-3-hydroxy-7-methoxy-6-(5-oxazolyl)-4(1H)-quinolinone

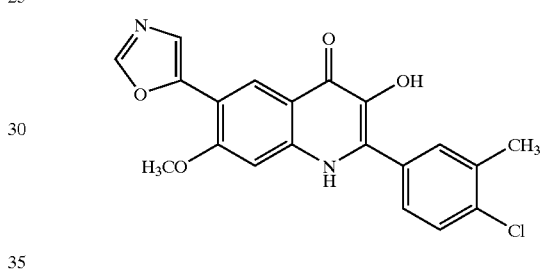

To a solution of 124A (0.06 g, 0.15 mmol) in acetic acid (1.5 mL) was added ammonium acetate (0.044 g, 2.25 mmol) and the contents heated at 120° C. for eighteen hours. The reaction mixture was concentrated and partitioned between dichloromethane/methanol (8:2, 20 mL) and water (20 mL). The dichloromethane/methanol layer was dried over sodium sulfate and concentrated. To the residue was added methanol and the solid that separates out was filtered. The filtrate was concentrated under reduced pressure and purified by preparative HPLC to yield the title compound (0.005 g) as the trifluoroacetic acid salt. LC-MS: Column A, retention time=3.44 minutes, m/z 383 (M+H)$^+$.

Example 125

2-(2,3-Dihydro-3-methoxy-1H-inden-5-yl)-3-hydroxy-7-methoxy-6-(5-oxazolyl)-4(1H)-quinolinone

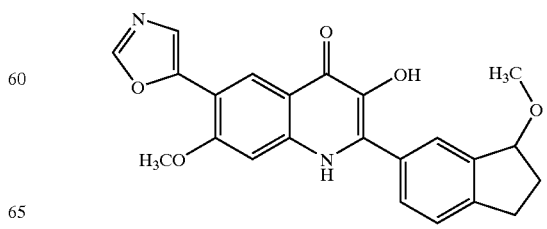

Example 125, Part A

2-Bromo-1-(2,3-dihydro-3-methoxy-1H-inden-5-yl)ethanone

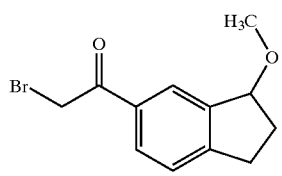

125A

To a solution of 110A (0.525 g, 2.31 mmol) in anhydrous dioxane (10 mL) was sequentially added tributyl(1-ethoxyvinyl)tin (0.82 mL, 2.42 mmol) and bis(triphenylphosphine)palladium(II)dichloride (0.081 g, 0.11 mmol). The reaction mixture was heated at 100° C. for eighteen hours, cooled to room temperature and filtered.

To the filtrate was added water (10 mL) followed by N-bromosuccinamide (0.452 g, 2.54 mmol) and the contents stirred at room temperature for one hour. The reaction mixture was partitioned between ethyl acetate (2×20 mL) and water (10 mL). The ethyl acetate layer was washed with brine, dried over sodium sulfate, concentrated and purified by silica gel flash chromatography (hexane/ethyl acetate, 9:1 as eluent) to yield the title compound (0.495 g, 79%). $^1$H NMR (CDCl$_3$): □ 7.93 (s, 1H), 7.85 (d, 1H), 7.3 (d, 1H), 4.8 (m, 1H), 4.4 (m, 2H), 3.4 (s, 1H), 3.1 (m, 1H), 2.85 (m, 1H), 2.4 (m, 1H), 2.1 (m, 1H).

Example 125, Part B 2-(2,3-Dihydro-3-methoxy-1H-inden-5-yl)-3-hydroxy-7-methoxy-6-(5-oxazolyl)-4(1H)-quinolinone

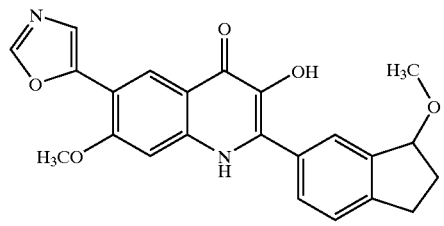

The title compound was made in a manner similar to 118 employing 125A in place of 2-bromoacetophenone in step A. LC-MS: Column A, retention time=3.01 minutes, m/z 405.17 (M+H)$^+$.

EXAMPLE 126

3-Hydroxy-7-methoxy-2-[2-(methylsulfonyl)phenyl]-6-(5-oxazolyl)-4(1H)-quinolinone

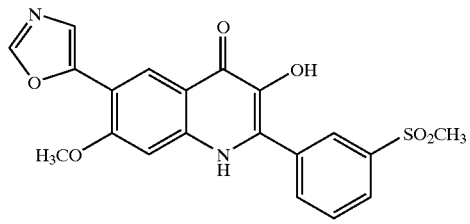

To 118A (125 mg. 0.35 mmol) was added Eaton's reagent (4.5 ml) and the contents heated at 100° C. for 2.5 hr. The reaction mixture was poured into crushed ice and extracted with dichloromethane. The dichloromethane layer is successively washed with sat. aqueous sodium bicarbonate, brine, dried over sodium sulfate, concentrated and purified by silica gel flash chromatography (100% Ethyl acetate as eluent) to give the title compound (10 mg). LC-MS: Column A, retention time=3.04 minutes, m/z 413.04 (M+H)$^+$.

EXAMPLE 127

2-[1-(Dimethylamino)-2,3-dihydro-1H-inden-5-yl]-7-methoxy-6-(5-oxazolyl)-4(1H)-quinolinone

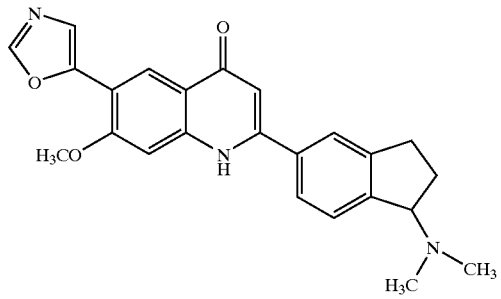

Example 127, Part A

5-Bromo-2,3-dihydro-N,N-dimethyl-1H-inden-1-amine

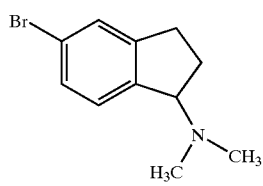

127A

To a solution of 5-bromo-1-chloro-indane (542 mg, 2.35 mmol) in toluene (9 ml) was added dimethylamine (3 ml) and resulting mixture was heated at 90° C. for 1.5 hr. The reaction mixture is concentrated under reduced pressure to yield the title compound (300 mg, 53%). $^1$H NMR (CDCl$_3$): 2.06 (m, 2H), 2.24 (s, 6H), 2.81–2.93 (m, 2H), 4.27 (t, 1H), 7.22 (d, 1H), 7.33 (d 1H), 7.36 (s, 1H).

Example 127, Part B

2-[1-(Dimethylamino)-2,3-dihydro-1H-inden-5-yl]-7-methoxy-6-(5-oxazolyl)-4(1H)-quinolinone

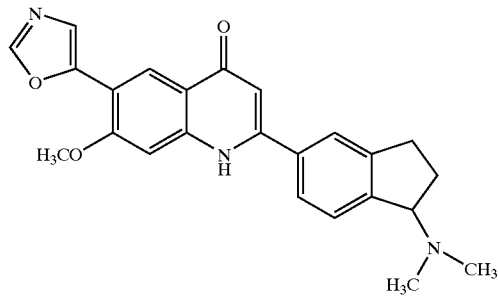

Compound 127A was subjected to the conditions outlined in C2 to yield the title compound. LC-MS: Column A, retention time=2.41 minutes, m/z 402.15 (M+H)$^+$.

EXAMPLE 128

2-(2,3-Dihydro-3-methoxy-2,2-dimethyl-1H-inden-5-yl)-7-methoxy-6-(5-oxazolyl)-4(1H)-quinolinone

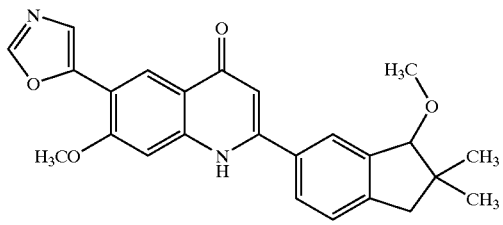

This compound was prepared using conditions outlined in C2 and using 5-Bromo-2,2-dimethyl-1-hydroxy-indane. LC-MS: Column A, retention time=3.50 minutes, m/z 417.13 (M+H)$^+$.

EXAMPLE 129

2-(2,3-Dihydro-3-methoxy-1,1-dimethyl-1H-inden-5-yl)-7-methoxy-6-(5-oxazolyl)-4(1H)-quinolinone

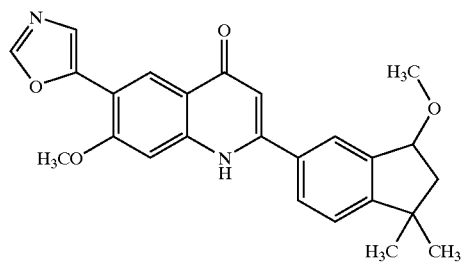

Example 129, Part A

5-Bromo-2,3-dihydro-3-methoxy-1,1-dimethyl-1H-indene

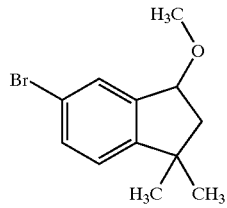

129A

To a solution of 5-Bromo-3,3-dimethyl-1-hydroxy-indane (200 mg, 0.83 mmol) in THF was added sodium hydride (32 mg, 1.33 mmol) and resulting mixture was stirred for 15 min. Iodomethane was added dropwise and stirring continued for 1 hr. The reaction mixture was concentrated under reduced pressure, extracted into ethyl acetate, washed with H$_2$O, dried over Na$_2$SO$_4$, concentrated and purified using silica gel flash chromatography (EtOAc/Hex, 1:5 as eluent) to yield the title compound (105 mg). $^1$H NMR(CDCl$_3$): □ 1.14 (s, 3H), 1.28 (s, 3H), 1.85 (s, 1H), 2.18 (s, 1H), 3.34 (s, 3H), 4.70 (t, 1H), 6.98 (s, 1H), 7.222 (d, 1H), 7.41 (s, 1H).

Example 129, Part B 2-(2,3-Dihydro-3-methoxy-1,1-dimethyl-1H-inden-5-yl)-7-methoxy-6-(5-oxazolyl)-4(1H)-quinolinone

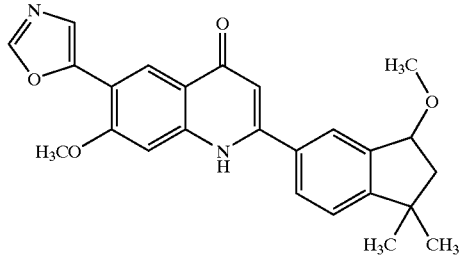

Compound 129A was subjected to the conditions outlined in C2 to yield the title compound. LC-MS: Column A, retention time=3.41 minutes, m/z 417.13(M+H)$^+$.

EXAMPLE 130 trans-2-[3-(Dimethylamino)-2,3-dihydro-2-methoxy-1H-inden-5-yl]-7-methoxy-6-(5-oxazolyl)-4(1H)-quinolinone

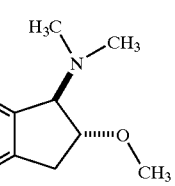

Example 130, Part A trans-6-Bromo-2,3-dihydro-2-hydroxy-N,N-dimethyl-1H-inden-1-amine

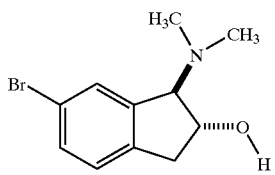

130A

A mixture of 5-bromoindene (608 mg, 3.12 mmol) and m-CPBA (804 mg, 3.27 mmol) in $CH_2Cl_2$ was stirred at room temperature for eighteen hours. The solid that separated out was filtered. The filtrate was concentrated under reduced pressure and subjected to silica gel flash chromatography (EtOAc/Hex 1:8 as eluent) to give the epoxide (350 mg, 53%) which was used as such for the subsequent step.

To the epoxide obtained above (350 mg, 1.66 mmol), dimethylamine (5.6 M in ethanol, 3 ml) was added and the contents heated in a sealed tube at 100° C. for eighteen hours. The reaction mixture was concentrated under reduced pressure and the residue partitioned between ethyl acetate (30 mL) and 1N HCl (15 ml). The HCl layer was basified with 1 N NaOH and extracted into EtOAc, washed with brine, dried over $Na_2SO_4$ and concentrated to yield the title compound (420 mg, 95%). $^1$H NMR (CDCl$_3$): □ 2.37 (s, 6H), 2.70 (q, 1H), 3.15 (q, 1H), 4.06 (d, 1H), 4.60 (q, 1H), 7.02 (d, 1H), 7.29 (d, 1H), 7.42 (s, 1H).

Example 130, Part B trans-6-Bromo-2,3-dihydro-2-methoxy-N,N-dimethyl-1H-inden-1-amine

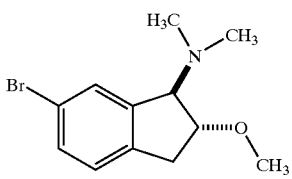

130C

Compound 130A was methylated analogous to 129 (part A) to yield the title compound.

Example 130, Part C trans-2-[3-(Dimethylamino)-2,3-dihydro-2-methoxy-1H-inden-5-yl]-7-methoxy-6-(5-oxazolyl)-4(1H)-quinolinone

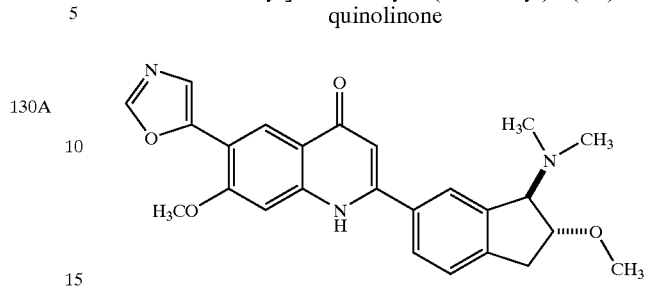

Compound 130D was subjected to the conditions outlined in C2 to yield the title compound. LC-MS: Column A, retention time=2.69 minutes, m/z 432.09(M+H)$^+$.

EXAMPLE 131 trans-2-[3-(Dimethylamino)-2,3-dihydro-2-hydroxy-1H-inden-5-yl]-7-methoxy-6-(5-oxazolyl)-4(1H)-quinolinone

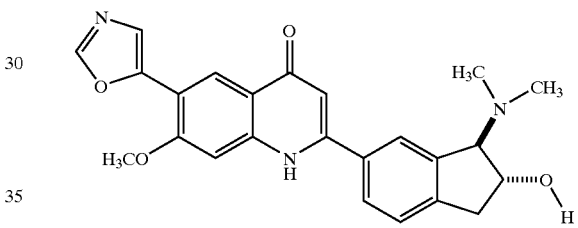

Compound 130 was subjected to the conditions outlined in C2 to yield the title compound. LC-MS: Column A, retention time=2.40 minutes, m/z 418.07(M+H)$^+$.

EXAMPLE 132 trans-6-[1,4-Dihydro-7-methoxy-6-(5-oxazolyl)-4-oxo-2-quinolinyl]-1-(dimethylamino)-2,3-dihydro-1H-inden-2-ol methylcarbamate

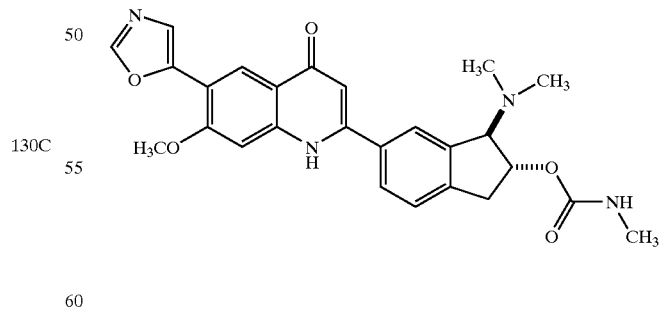

A mixture of 131 (50 mg, 0.12 mmol), methyl isocyanate (15 mg, 0.14 mmol) in pyridine (1 ml) was heated at 65° C. for 2 hr. The reaction mixture was concentrated under reduced pressure and to the residue was added ethyl acetate. The solid that separates out is filtered and dried to yield the title compound (15 mg). LC-MS: Column A, retention time=2.59 minutes, m/z 475.16 (M+H)$^+$.

EXAMPLE 133

Ethylcarbamic acid trans-6-[1,4-dihydro-7-methoxy-6-(5-oxazolyl)-4-oxo-2-quinolinyl]-1-(dimethylamino)-2,3-dihydro-1H-inden-2-yl ester

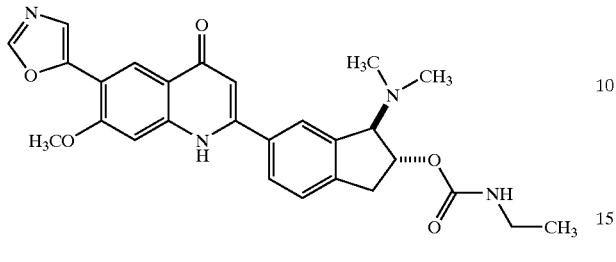

This compound was prepared analogous to 132 using ethyl isocyanate. LC-MS: Column A, retention time=2.76 minutes, m/z 489.16 (M+H)$^+$.

EXAMPLE 134

(1-Methylethyl)carbamic acid trans-6-[1,4-dihydro-7-methoxy-6-(5-oxazolyl)-4-oxo-2-quinolinyl]-1-(dimethylamino)-2,3-dihydro-1H-inden-2-yl ester

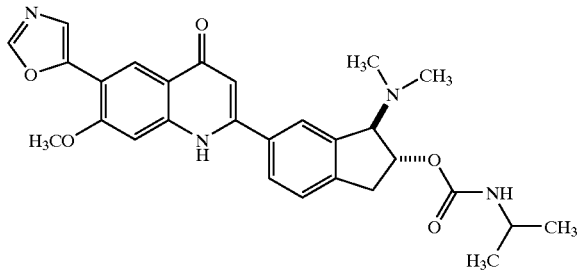

This compound was prepared analogous to 132 using isopropyl isocyanate. LC-MS: Column A, retention time=2.46 minutes, m/z 503.17 (M+H)$^+$.

EXAMPLE 135

(2-Chloroethyl)carbamic acid trans-6-[1,4-dihydro-7-methoxy-6-(5-oxazolyl)-4-oxo-2-quinolinyl]-1-(dimethylamino)-2,3-dihydro-1H-inden-2-yl ester

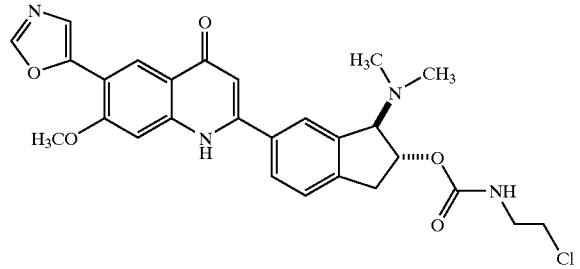

This compound was prepared analogous to 132 using 2-chloroethyl isocyanate. LC-MS: Column A, retention time=2.79 minutes, m/z 523.07 (M+H)$^+$.

EXAMPLE 136

Imidodicarbonic acid trans-6-[1,4-dihydro-7-methoxy-6-(5-oxazolyl)-4-oxo-2-quinolinyl]-1-(dimethylamino)-2,3-dihydro-1H-inden-2-yl methyl ester

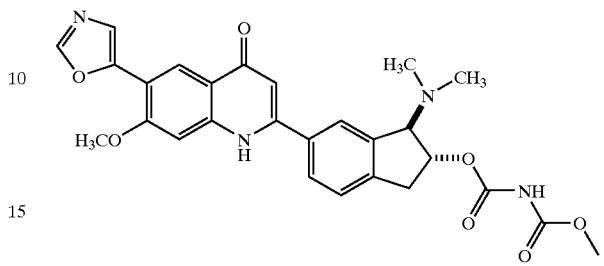

This compound was prepared analogous to 132 using methyl isocyanatoformate. LC-MS: Column A, retention time=2.61 minutes, m/z 519.12 (M+H)$^+$.

EXAMPLE 137

7-Methoxy-2-[4-methyl-3-(phenylmethoxy)phenyl]-6-(5-oxazolyl)-4(1H)-quinolinone

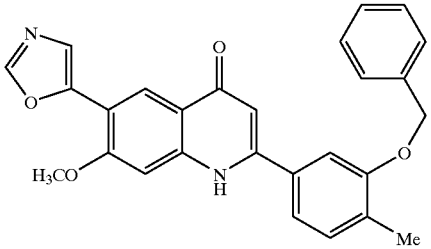

Example 137, Part A

4-Methyl-b-oxo-3-(phenylmethoxy)benzenepropanoic acid ethyl ester

137A

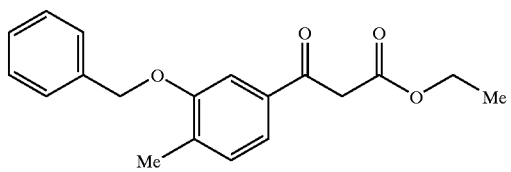

Compound 137A was prepared from 3-benzyl-4-methylbenzoic acid in an analogous way to Method A3 (Example 3). HPLC retention time; 1.770 min.; Column conditions B.

Example 2, Part B

7-Methoxy-2-[4-methyl-3-(phenylmethoxy)phenyl]-6-(5-oxazolyl)-4(1H)-quinolinone 137 was prepared from 137A in a similar method to Method A2 (Example 2) with pyridinium p-toluenesulfonate used for the H+ source and diphenyl ether replacing xylene in the cyclization step. HPLC retention time: 1.814 min.; Column conditions B; 439$^+$ (M+H)$^+$.

EXAMPLE 138

2-(3-Hydroxy-4-methylphenyl)-7-methoxy-6-(5-oxazolyl)-4(1H)-quinolinone

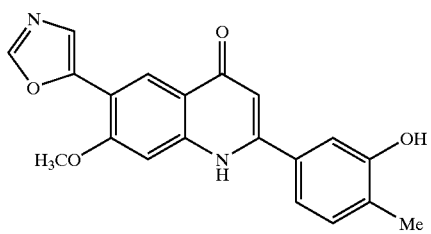

Example 138, Part A

7-Methoxy-4-(methoxymethoxy)-2-[4-methyl-3-(phenylmethoxy)phenyl]-6-(5-oxazolyl)quinoline

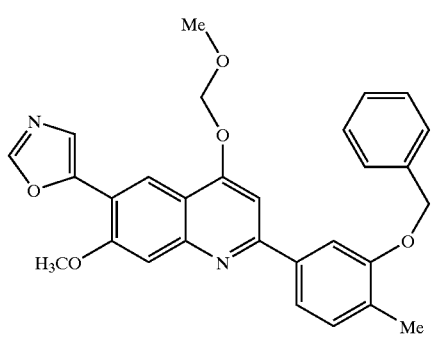

138A

Compound 138A was prepared from 137 in an analogous method to the first step in Method B1 (Example 3) with the reaction being run at 70° C. HPLC retention time: 1.711 min.; Column conditions B.

Example 138, Part B 2-(3-Hydroxy-4-methylphenyl)-7-methoxy-6-(5-oxazolyl)-4(1H)-quinolinone 138 was prepared from 138A through hydrogenation using palladium on activated carbon (10%), $H_2$, and MeOH/THF (12.5:1 ratio) as solvent. HPLC retention time: 2.886 min.; Column conditions: YMC S5 ODS 4.6×50 mm; Gradient time: 4 min.; Flow rate=4 ml/min.; Solvent A=10% MeOH, 90% $H_2O$, 0.1% TFA; Solvent B=90% MeOH, 10% $H_2O$, 0.1% TFA; Start % B=0; Final % B=100; 349+(M+H)+.

EXAMPLE 139

7-Methoxy-2-[3-(2-methoxyethoxy)-4-methylphenyl]-6-(5-oxazolyl)-4(1H)-quinolinone

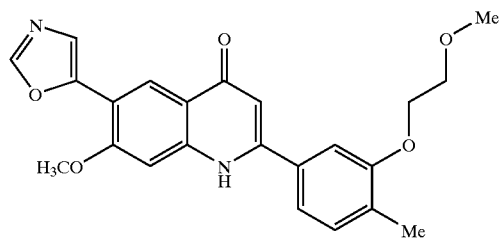

Example 139, Part A

5-[7-Methoxy-4-(methoxymethoxy)-6-(5-oxazolyl)-2-quinolinyl]-2-methylphenol

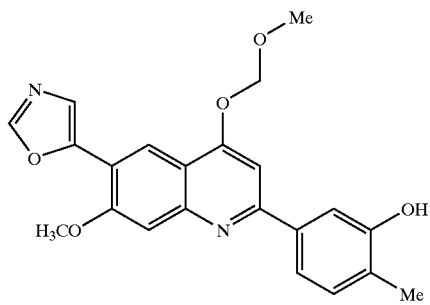

139A 139A was prepared from 138A through hydrogenation using palladium on activated carbon (10%), $H_2$, and MeOH/THF (12.5:1 ratio) as solvent. HPLC retention time: 1.458 min.; Column conditions B.

Example 139, Part B

7-Methoxy-2-[3-(2-methoxyethoxy)-4-methylphenyl]-6-(5-oxazolyl)-4(1H)-quinolinone 139 was prepared by coupling 138A with 2-chloroethyl methyl ether using $K_2CO_3$ in DMF at 80° C. Aqueous work up done before compounds were deprotected using TFA in $CH_2Cl_2$. Products then purified by Prep HPLC. HPLC retention time: 1.58 min.; column conditions B; (M+H)+ 407.

EXAMPLE 140

7-Methoxy-2-[4-methyl-3-[(1-methyl-3-piperidinyl)methoxy]phenyl]-6-(5-oxazolyl)-4(1H)-quinolinone

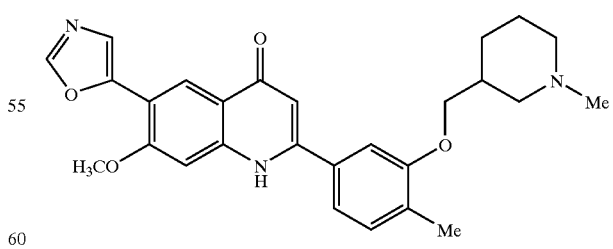

140 was prepared by coupling 138A with the respective 3-chloromethyl-1-methyl piperdine using $K_2CO_3$ in DMF at 80° C. Aqueous work up done before compounds were deprotected using TFA in $CH_2Cl_2$. Products then purified by Prep HPLC. HPLC retention time: 1.41 min.; column conditions B; (M+H)+ 460.

EXAMPLES 141–149

Examples 141–149 were prepared using 138A, the respective alcohols, diethyl azodicarboxylate, and triphenylphosphine in THF. Compounds were purified by normal phase silica gel column before being deprotected with TFA in $CH_2Cl_2$. Compounds then purified by either normal phase silica gel column or by Prep HPLC.

TABLE 2

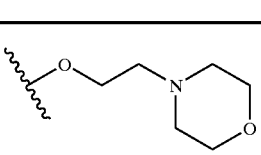

| Ex. No. | Compound Name | R[1] | HPLC conditions/ retention time (min.) | LC-MS $(M + H)^+$ |
|---|---|---|---|---|
| 141 | 7-Methoxy-2-[4-methyl-3-[2-(4-morpholinyl) ethoxy] phenyl]-6-(5-oxazolyl)-4(1H)-quinolinone | 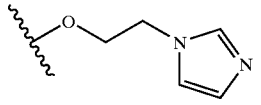 | B/1.27 | 462+ |
| 142 | 7-Methoxy-2-[4-methyl-3-[[2-(1H-imidazol-1-yl) ethoxy]phenyl]-6-(5-oxazolyl)-4(1H)-quinolinone | 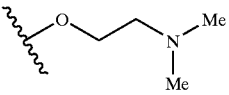 | F/1.35 | 443+ |
| 143 | 2-[3-[2-(Dimethylamino) ethoxy]-4-methylphenyl]-7-methoxy-6-(5-oxazolyl)-4(1H)-quinolinone | 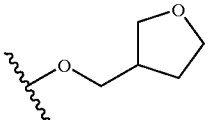 | F/1.35 | 420+ |
| 144 | 7-Methoxy-2-[4-methyl-3-[(tetrahydro-3-furanyl)methoxy] phenyl]-6-(5-oxazolyl)-4(1H)-quinolinone | 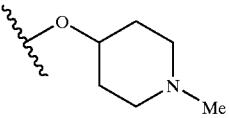 | B/1.57 | 433+ |
| 145 | 7-Methoxy-2-[4-methyl-3-[(1-methyl-4-piperidinyl)oxy] phenyl]-6-(5-oxazolyl)-4(1H)-quinolinone | 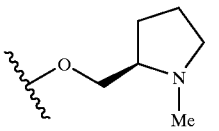 | B/1.32 | 446+ |
| 146 | 7-Methoxy-2-[4-methyl-3-[[(2S)-1-methyl-2-pyrrolidinyl] methoxy]phenyl]-6-(5-oxazolyl)-4(1H)-quinolinone | | B/1.33 | 446+ |

TABLE 2-continued

| Ex. No. | Compound Name | R[1] | HPLC conditions/ retention time (min.) | LC-MS (M + H)+ |
|---|---|---|---|---|
| 147 | 7-Methoxy-2-[4-methyl-3-[(1-methyl-3-pyrrolidinyl)oxy]phenyl]-6-(5-oxazolyl)-4(1H)-quinolinone | | B/1.30 | 432+ |
| 148 | 7-Methoxy-2-[4-methyl-3-[2-(2-pyridinyl)ethoxy]phenyl]-6-(5-oxazolyl)-4(1H)-quinolinone | | C/2.64 | 454+ |
| 149 | 7-Methoxy-2-[4-methyl-3-[(tetrahydro-2-furanyl)methoxy]phenyl]-6-(5-oxazolyl)-4(1H)-quinolinone | | A/3.24 | 433+ |

Example 150

6-[1,4-Dihydro-7-methoxy-6-(5-oxazolyl)-4-oxo-2-quinolinyl]-2,3-dihydro-N,N,N-trimethyl-1H-inden-1-aminium

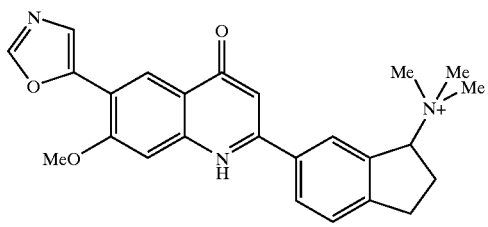

150 was prepared by methylating 10 using $K_2CO_3$ and methyl iodide in acetone refluxing at 48° C. Compound was purified by Prep HPLC. HPLC retention time: 1.20 min.; column condition B; (M+H)+ 417+.

EXAMPLE 151
2-[3-(Dimethylamino)-2,3-dihydro-1H-inden-5-yl]-3-hydroxy-7-methoxy-6-(5-oxazolyl)-4(1H)-quinolinone

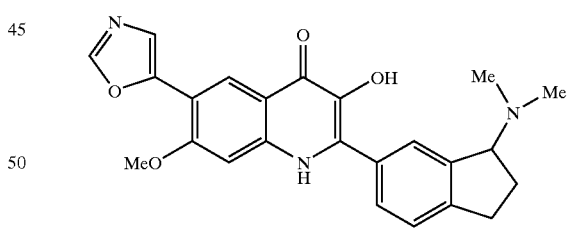

Example 151, Part A
6-(Bromoacetyl)-2,3-dihydro-N,N-dimethyl-1H-inden-1-amine

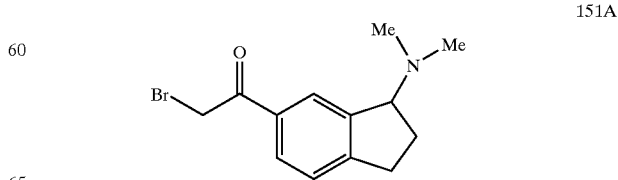

151A 151A was prepared from 10A by an analogous method described for the preparation of 110A.

Example 151, Part B

2-Amino-4-methoxy-5-(5-oxazolyl)benzoic acid 2-[2,3-dihydro-3-(dimethylamino)-1H-inden-5-yl]-2-oxoethyl ester

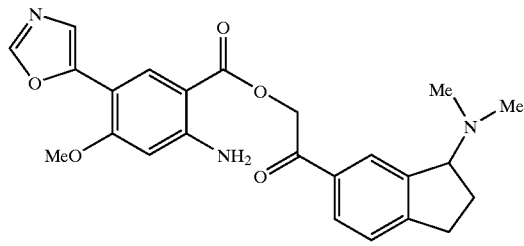

151B

A mixture of 118B (58 mg, 0.246 mmol) and potassium carbonate (75 mg, 0.542 mmol) in dry DMF (1.0 mL) was heated to 90° C. for 1 hr, then cooled to 0° C. A solution of Compound 1b (69 mg, 0.246 mmol) in 1.0 mL of dry DMF was added and the mixture was stirred at ambient temperature for 2.0 hr. The reaction mixture partitioned between ethyl acetate and ice water, extracted with ethyl acetate (2×). The combined organic extracts were washed once with 10% LiCl aq. solution, dried over anhydrous $Na_2SO_4$. Concentration in vacuo followed by flash chromatography ($CH_2Cl_2$-MeOH: 95:5) on silica gel afforded 50 mg of 151B as a colorless oil.

Example 151, Part C

2-[3-(Dimethylamino)-2,3-dihydro-1H-inden-5-yl]-3-hydroxy-7-methoxy-6-(5-oxazolyl)-4(1H)-quinolinone A mixture of Compound 151B (27 mg, 0.062 mmol), p-TsOH monohydrate (24 mg, 0.124 mmol) and propionic acid (92 mg, 1.24 mmol) in 2 mL of dry toluene was heated to reflux for 4.0 hr. After the solvent was removed under reduced pressure, the residue was taken into $CH_2Cl_2$ and washed with pH 7.0 buffer solution. The organic layer was dried over anhydrous $Na_2SO_4$. Concentration in vacuo followed by flash chromatography ($CH_2Cl_2$-MeOH—$NH_4OH$: 90:10:0 to 90:10:1) on silica gel afforded 23.8 mg of the target compound as a, yellow solid. HPLC retention time: 2.289 min (Column conditions C). LC-MS: 418$^+$ (M+H)$^+$.

EXAMPLE 152

1,4-Dihydro-3-hydroxy-7-methoxy-2-(4-methylphenyl)-4-oxo-6-quinolinecarbonitrile

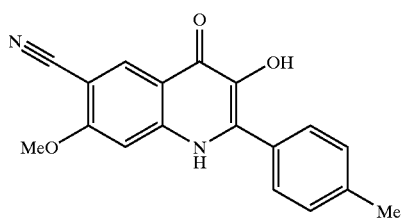

Example 152, Part A

2-Amino-5-cyano-4-methoxybenzoic acid

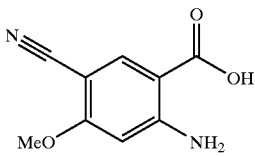

152A

Compound 152A was prepared by an analogous method as that of 118B starting from 3-methoxy-4-cyanoaniline.

Example 152, Part B

2-Amino-5-cyano-4-methoxybenzoic acid 2-(4-methylphenyl)-2-oxoethyl ester

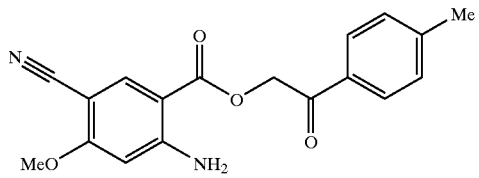

152B 152B was prepared by an analogous method as that of 151B starting from Compound 152A.

Example 152, Part C 1,4-Dihydro-3-hydroxy-7-methoxy-2-(4-methylphenyl)-4-oxo-6-quinolinecarbonitrile 152 was prepared by an analogous method described for the preparation of 151. HPLC retention time: 2.836 min (Column conditions C). LC-MS: 307$^+$ (M+H)$^+$.

EXAMPLE 153

1,4-Dihydro-3-hydroxy-7-methoxy-2-(3-methylphenyl)-4-oxo-6-quinolinecarbonitrile

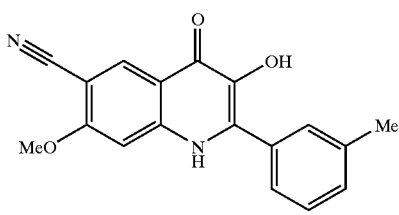

153 was prepared by an analogous method as that of Compound 152. HPLC retention time: 2.806 min (Column conditions C). LC-MS: 307$^+$ (M+H)$^+$.

147

EXAMPLE 154

7-Methoxy-6-(5-oxazolyl)-4(1H)-quinolinone

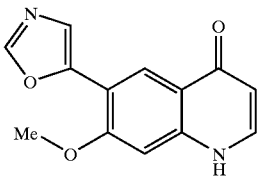

Example 154, Part A

5-[[[3-Methoxy-4-(5-oxazolyl)phenyl]amino]methylene]-2,2-dimethyl-1,3-dioxane-4,6-dione

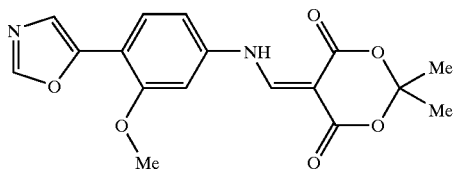

154A

To 1D (500 mg, 2.6 mmol) in MeOH (5 mL) at room temperature was added 5-(Methoxymethylene)-2,2-dimethyl-1,3-dioxane-4,6-dione (490 mg, 2.6 mmol). The mixture was stirred at room temperature for 15 min then cooled in an ice bath and the solid filtered with cold MeOH rinse to give 880 mg (97%) of a yellow solid solid.

Example 154, Part B

7-Methoxy-6-(5-oxazolyl)-4(1H)-quinolinone 154A (820 mg, 2.38 mmol) in diphenylether (10 mL) was heated in a 200° C. bath for 2.5 h. The reaction was then cooled to room temperature and 10 mL hexane was added. The solid was filtered to give 545 mg (95%) of the title compound as an off white solid. HPLC Ret. Time: 2.756 min (Method A). Mass Spec: 243 (M+H$^+$).

EXAMPLE 155

7-Methoxy-2-(methylthio)-6-(5-oxazolyl)-4(1H)-quinolinone

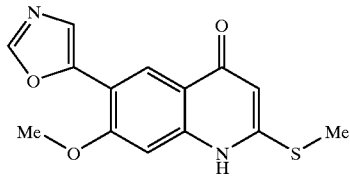

To 1D (500 mg, 2.63 mmol) in diphenylether (5 mL) was added 5-[Bis(methylthio)methylene]-2,2-dimethyl-1,3-dioxane-4,6-dione (653 g, 2.63 mmol) and the mixture heated to 120° C. for 2 h. The reaction was then heated to 200° C. for 15 min then cooled to room temperature. Hexane was added to the mixture and the solid was filtered to give 675 mg (89%) of the title compound as a yellow solid. HPLC Ret. Time: 2.316 min (Method A). Mass Spec: 289 (M+H$^+$)

148

EXAMPLE 156

2-(2,3-Dihydro-3-hydroxy-1H-inden-5-yl)-7-methoxy-6-(5-oxazolyl)-4(1H)-quinolinone

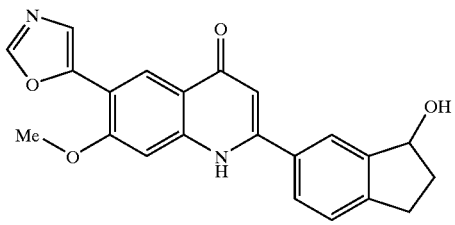

Example 156, Part A

6-Bromo-2,3-dihydro-1-[[tris(1-methylethyl)silyl]oxy]-1H-indene

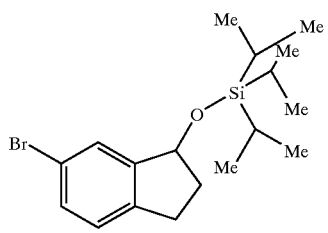

156A

To 6-Bromo-2,3-dihydro-1H-inden-1-ol (300 mg, 1.41 mmol) in CH$_2$Cl$_2$ (4 mL) was added 2,6-lutidine (151 µL, 1.41 mmol) followed by triisopropylsilyltriflate (378 µL, 1.41 mmol) at room temperature. The reaction was stirred for 30 min then added to 1N HCl and extracted. The organic layer was washed with saturated sodium bicarbonate then brine and dried over MgSO$_4$. The solvent was removed in vacuo and the crude material purified by column chromatography.

Example 156, Part B 2,2-Dimethyl-5-[(methylthio) [3[[tris(1-methylethyl)silyl]oxy]-1H-inden-5-yl]methylene]-1,3-dioxane-4,6-dione

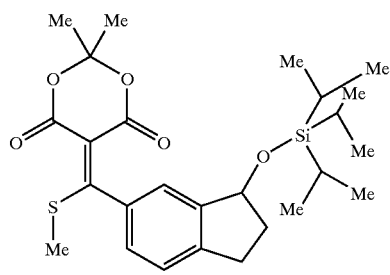

156B

To 156A (843 mg, 1.72 mmol) in THF (10 mL) with magnesium (83 mg, 3.43 mmol) at 50° C. was added catalytic dibromoethane. The reaction was cooled to room temperature then transferred via canula to 5-[Bis(methylthio)methylene]-2,2-dimethyl-1,3-dioxane-4,6-dione (380 mg, 1.53 mmol) in THF (10 mL). The reaction was quenched with 1N HCl and extracted with Et$_2$O. The organic layer was washed with brine, dried over MgSO$_4$, filtered and the solvent removed in vacuo. The crude product was used as is in the next step.

Example 156, Part C

7-Methoxy-6-(5-oxazolyl)-2-[3-[[tris(1-methylethyl) silyl oxy]-1H-inden-5-yl]-4(1H)-quinolinone

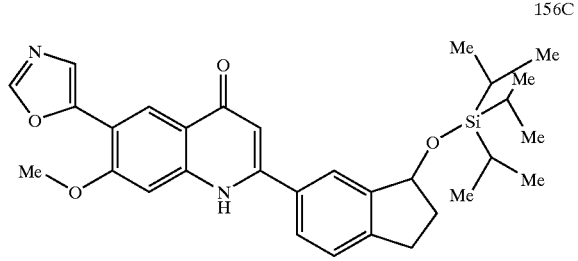

156C

To crude 156B (1.5 mmol) in diphenylether (10 mL) was added 1D (290 mg, 1.52 mmol) and the reaction was heated to 140° C. for 6 h then heated to 200° C. for 15 min. The reaction was cooled to room temperature and hexane was added, then the solid filtered and rinsed with hexane to give 539 mg 156C.

Example 156, Part D 2-(2,3-Dihydro-3-hydroxy-1H-inden-5-yl)-7-methoxy-6-(5-oxazolyl)-4(1H)-quinolinone To 156C (100 mg, 0.19 mmol) in MeOH (30 mL) was added 1N HCl (7 mL) and the reaction stirred at room temperature for 18 h. The solvent was then removed in vacuo and water was added. The solid precipitate was filtered with water rinse followed by Et$_2$O rinse to give 67 mg (95%) of the title compound as a off white solid. HPLC retention time: 2.749 min (Method A). Mass Spec: 375 (M+H$^+$)

EXAMPLE 157

2-(3,4-Dimethoxyphenyl)-7-methoxy-6-(5-oxazolyl)-4(1H)-quinolinone

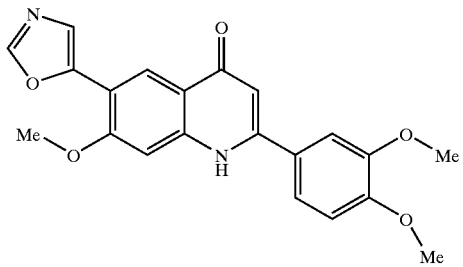

Example 157, Part A 5-((3,4-Dimethoxyphenyl)[[3-methoxy-4-(5-oxazolyl)phenyl]amino]methylene]-2,2-dimethyl-1,3-dioxane-4,6-dione

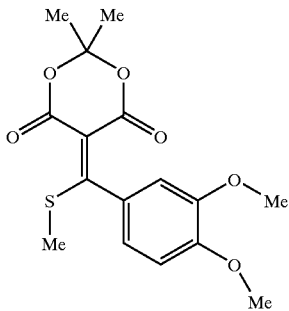

157A 157A was prepared from 4-bromoveratrole (100 mg, 0.46 mmol) and 5-[Bis(methylthio)methylene]-2,2-dimethyl-1,3-dioxane-4,6-dione (76 mg, 0.3 mmol) using the same procedure as 156B to give 80 mg (78%).

Example 157, Part B

5-[[5-((Dimethylamino)methyl]-3-thienyl] (methylthio)methylene]-2,2-dimethyl-1,3-dioxane-4,6-dione

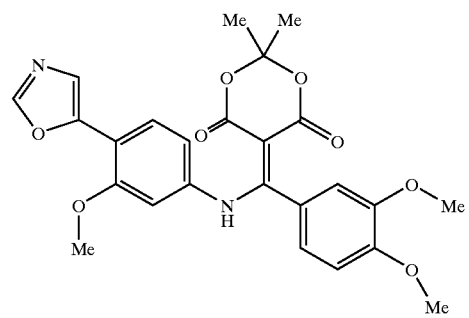

157B

To 157A (60 mg, 0.17 mmol) in EtOH (2 mL) was added 1D (34 mg, 0.17 mmol) and the reaction was heated to reflux for 12 h. The reaction was cooled in ice and the solid filtered with cold EtOH rinse to give 48 mg of 157B.

Example 157, Part C 2-(3,4-Dimethoxyphenyl)-7-methoxy-6-(5-oxazolyl)-4(1H)-quinolinone 157B (40 mg, 0.083 mmol) in diphenylether (700 μL) was heated to 200° C. for 1 h then cooled to room temperature. Hexane was added to the mixture and the solid filtered with hexane rinse to give 28 mg (87%) of the title compound. HPLC retention time: 2.756 min (Method A). Mass Spec: 379 (M+H$^+$).

EXAMPLE 158

2-[5-[(Dimethylamino)methyl]-3-thienyl]-7-methoxy-6-(5-oxazolyl)-4(1H)-quinolinone

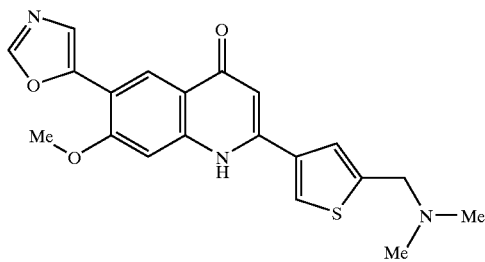

Example 158, Part A

5-[[5-[(Dimethylamino)methyl]-3-thienyl](methylthio)methylene]-2,2-dimethyl-1,3-dioxane-4,6-dione

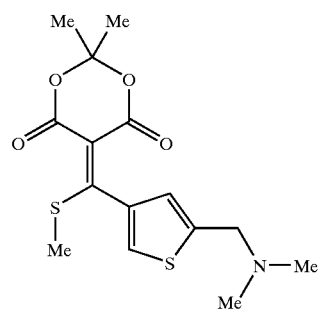

158A

To 4-Bromo-N,N-dimethyl-2-thiophenemethanamine (130 mg, 0.59 mmol) in THF (2 mL) cooled to −78° C. was added n-BuLi (230 µL, 0.59 mmol) dropwise. The reaction was stirred at −78° C. for 15 min then the reaction was rapidly tranfered via canula to 5-[Bis(methylthio)methylene]-2,2-dimethyl-1,3-dioxane-4,6-dione (125 mg, 0.50 mmol) in THF (2 mL) stirring at room temperature. The reaction was quenched with 1N HCl and extracted with CH$_2$Cl$_2$ and saturated sodium bicarbonate. The crude reaction residue was purified by column chromatography to give 74 mg of 158A.

Example 158, Part B

2-[5-[(Dimethylamino)methyl]-3-thienyl]-7-methoxy-6-(5-oxazolyl)-4(1H)-quinolinone To 158A (74 mg, 0.21 mmol) in diphenylether (2 mL) was added ID (41 mg, 0.21 mmol) and the reaction was heated to 120° C. for 6 h. The reaction was heated to 200° C. for 10 min then cooled to room temperature. Hexane was added to the reaction and the solid was filtered with hexane rinse to give 54 mg (67%) of the title compound. HPLC retention time: 2.033 min (Method A). Mass Spec: 382 (M+H$^+$).

EXAMPLE 159

2-[3-(Dimethylamino)-2,3-dihydro-1H-inden-5-yl]-7-methoxy-6-(5-oxazolyl)-4(1H)-quinolinone enantiomer A;

2-[3-(Dimethylamino)-2,3-dihydro-1H-inden-5-yl]-7-methoxy-6-(5-oxazolyl)-4(1H)-quinolinone enantiomer B

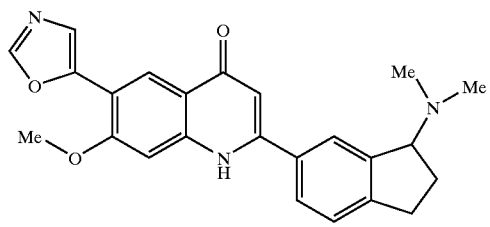

Example 159, Part A

5-[[3-(Dimethylamino)-2,3-dihydro-1H-inden-5-yl](methylthio)methylene]-2,2-dimethyl-1,3-dioxane-4,6-dione

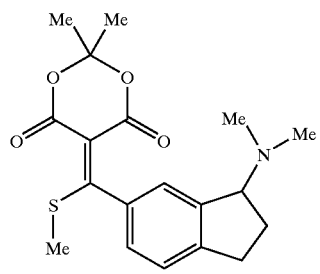

159A 159A was prepared from 10B (1.1 g, 4.58 mmol) and 5-[Bis(methylthio)methylene]-2,2-dimethyl-1,3-dioxane-4,6-dione (755 mg, 3.04 mmol) using the same procedure as 156B to give 1.2 g (72%).

Example 159, Part B, 159 was prepared from 159A (1.2 g, 3.32 mmol) and 1D (630 mg, 3.32 mmol) using the same procedure as 158 to give 1.0 g (75%). HPLC retention time: 2.22 min. (Method A). Mass Spec: 402 (M+H$^+$).

The two enantiomers were separated on a chiral preperative AS HPLC column eluted with 15% EtOH/Hexane with 0.12% Et$_3$N. The analytical chiral HPLC retention time for the first enantioner A is 11.5 min on a chiral AS analytical column eluted with 14% EtOH/Hexane with 0.12% Et$_3$N at 2 mL/min on a 35 min run time.

The second enantiomer B has a retention time on the analytical chiral AS column of 16.1 min using the same conditions.

Both enantiomers gave identical retention times with method A and identical Mass Spectra as given above.

EXAMPLE 160

7-Methoxy-2-(methylamino)-6-(5-oxazolyl)-4(1H)-quinolinone

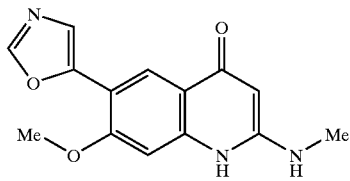

Example 160, Part A

5-[[[3-Methoxy-4-(5-oxazolyl)phenyl]amino](methylthio)methylene]-2,2-dimethyl-1,3-dioxane-4,6-dione

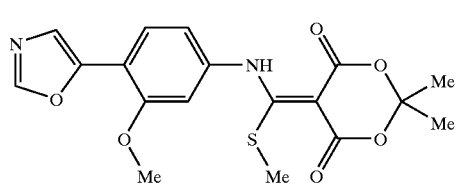

160A

To 1D (316 mg, 1.66 mmol) in MeOH (3 mL) was added 5-[Bis(methylthio)methylene]-2,2-dimethyl-1,3-dioxane-4,6-dione (412.5 mg, 1.66 mmol) and stirred at room temperature for 5 h. The reaction was cooled in an ice bath and filtered to give 620 mg (96%) of the title compound, as a yellow solid.

Example 160, Part B

5-[[[3-Methoxy-4-(5-oxazolyl)phenyl]amino](methylamino)methylene]-2,2-dimethyl-1,3-dioxane-4,6-dione

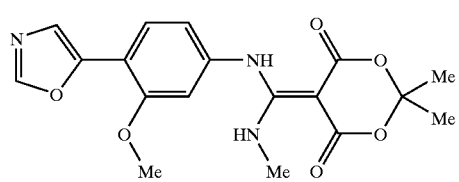

160B

To 160A (60 mg, 0.154 mmol) in THF (2 mL) was added dimethylamine (1 mL, M in H$_2$O) followed by HgCl$_2$ (41.8 mg, 0.154 mmol) at room temperature. The reaction was stirred for 2 h at room temperature then filtered. Water was added and the mixture extracted 3 times with CH$_2$Cl$_2$. The organic layer was washed with brine and dried over MgSO$_4$. After the solvent was removed the residue was purified by column chromatography to give 51.6 mg 160B.

Example 160, Part C

7-Methoxy-2-(methylamino)-6-(5-oxazolyl)-4(1H)-quinolinone 160B (51.6 mg, 0.14 mmol) in diphenylether (2 mL) was heated to 250° C. for 2 h. The reaction was cooled to room temperature and hexane was added. The solid was filtered and washed with hexane to give 29 mg (77%) of the title compound. HPLC retention time: 2.289 min (Method A). MassSpec: 272 (M+H$^+$).

EXAMPLE 161

2-(Dimethylamino)-7-methoxy-6-(5-oxazolyl)-4(1H)-quinolinone

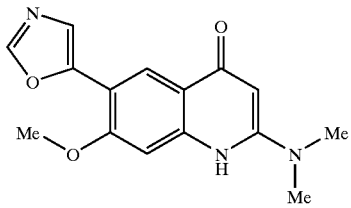

Example 161, Part A

5-[(Dimethylamino)[[3-methoxy-4-(5-oxazolyl)phenyl]amino]methylene]-2,2-dimethyl-1,3-dioxane-4,6-dione

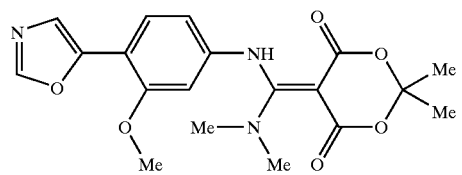

161A 161A was prepared from 160A (60 mg, 0.154 mmol) and dimethylamine (2 mL, M in EtOH) using the same procedure as 160B to give 35 mg.

Example 161, Part B 2-(Dimethylamino)-7-methoxy-6-(5-oxazolyl)-4(1H)-quinolinone 161 was prepared from 161A (35 mg, 0.09 mmol) and diphenylether (1 mL) using the same procedure as 160 to give 16 mg (62%) of the title compound. HPLC retention time: 2.276 min (Method A). Mass Spec 286 (M+H$^+$).

EXAMPLE 162

[6-[1,4-Dihydro-7-methoxy-6-(5-oxazolyl)-4-oxo-2-quinolinyl]-2,3-dihydro-1H-inden-1-yl]methylcarbamic acid 1,1-dimethylethyl ester

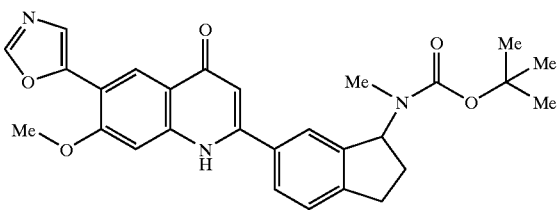

Example 162, Part A (6-Bromo-2,3-dihydro-1H-inden-1-yl)methylcarbamic acid 1,1-dimethylethyl ester

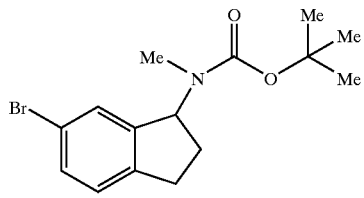

162A

To 104A (650 mg, 2.86 mmol) in MeOH (2 mL) was added di-tertbutyldicarbonate (722 mg, 3.44 mmol) and triethylamine (220 μL). The reaction was heated to reflux for 1 h then the solvent removed in vacuo and the residue was dissolved in Et$_2$O and washed with water then brine. The organic layer was dried over MgSO$_4$, filtered and the solvent removed in vacuo to give 782 mg of 162A.

Example 162, Part B

[6-[(2,2-Dimethyl-4,6-dioxo-1,3-dioxan-5-ylidene)(methylthio)methyl]-2,3-dihydro-1H-inden-1-yl]methylcarbamic acid 1,1-dimethylethyl ester

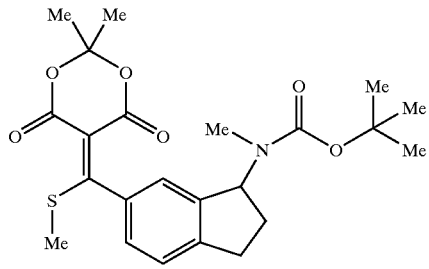

162B 162B was prepared from 162A (682 mg, 2.1 mmol) and 5-[Bis(methylthio)methylene]-2,2-dimethyl-1,3-dioxane-4,6-dione (495 mg, 2.1 mmol) using the same procedure as 156B to give 538 mg (57%).

Example 162, Part C

[6-[1,4-Dihydro-7-methoxy-6-(5-oxazolyl)-4-oxo-2-quinolinyl]-2,3-dihydro-1H-inden-1-yl]methylcarbamic acid 1,1-dimethylethyl ester 162 was prepared from 162B (538 mg, 1.2 mmol) and 1D (247 mg, 1.2 mmol) using the same procedure as 156C to give 269 mg (46%) of the title compound. HPLC retention time: 3.466 min (Method A). Mass spec: 488 (M+H$^+$).

EXAMPLE 163

N-[6-[1,4-Dihydro-7-methoxy-6-(5-oxazolyl)-4-oxo-2-quinolinyl]-2,3-dihydro-1H-inden-1-yl]-N-methylacetamide

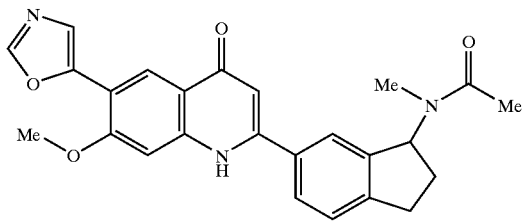

Example 163, Part A

2-[2,3-Dihydro-3-(methylamino)-1H-inden-5-yl]-7-methoxy-6-(5-oxazolyl)-4(1H)-quinolinone

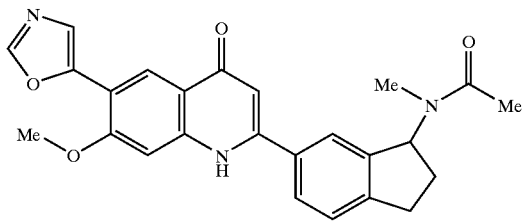

163A

To 162 (269 mg, 0.55 mmol) was added TFA (10 mL) and the mixture was stirred at room temperature for 3 h. The TFA was removed in vacuo and 1N HCl was added. The solid formed was filtered rinsed with 1N HCl and dried under vacuum to give 164.5 mg (70.5%) of 163A as an HCl salt.

Example 163, Part B

N-[6-[1,4-Dihydro-7-methoxy-6-(5-oxazolyl)-4-oxo-2-quinolinyl]-2,3-dihydro-1H-inden--yl]-N-methylacetamide To 163A (20 mg, 0.052 mmol) in DMF (1.5 mL) with Et$_3$N (18 μL, 0.13 mmol) cooled in a −10° C. bath was slowly added acetylchloride (3.7 μL, 0.052 mmol) dissolved in CH$_2$Cl$_2$ (0.5 mL). The reaction was stirred at −10° C. for 1 h then the solvent was removed in vacuo and the residue dissolved in CH$_2$Cl$_2$ and washed with water and brine. The organic phase was dried over MgSO$_4$ filtered and the solvent removed in vacuo to give 6.5 mg. HPLC retention time: 2.769 min (Method A). Mass spec: 430 (M+H$^+$).

EXAMPLE 164

N-[6-[1,4-Dihydro-7-methoxy-6-(5-oxazolyl)-4-oxo-2-quinolinyl]-2,3-dihydro-1H-inden-1-yl]-2-methoxy-N-methylacetamide

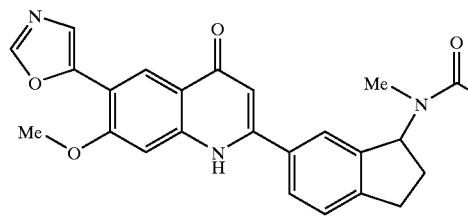

164 was prepared from 163A (20 mg, 0.052 mmol) and methoxy acetylchloride (4.7 µL, 0.052 mmol) using the same procedure as 163 to give 20.4 mg of the title compound. HPLC retention time: 2.752 min (Method A). Mass spec: 460 (M+H$^+$).

EXAMPLE 165

N-[6-[1,4-Dihydro-7-methoxy-6-(5-oxazolyl)-4-oxo-2-quinolinyl]-2,3-dihydro-1H-inden-1-yl]-N-methyl-1H-imidazole-1-acetamide

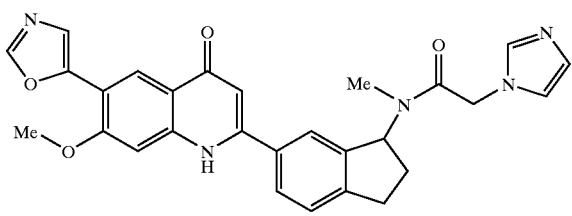

To 163A (20 mg, 0.052 mmol) in DMF (1.5 mL) with Et$_3$N (18 µL, 0.13 mmol) cooled in a −10° C. bath was slowly added chloroacetylchloride (4.1 µL, 0.052 mmol) dissolved in CH$_2$Cl$_2$ (0.5 mL). The reaction was stirred at −10° C. for 1 h then imidazole (7 mg, 0.1 mmol) and K$_2$CO$_3$ (21.5 mg, 0.156 mmol) and the reaction was heated to 60° C. for 1 h. The solvent was removed in vacuo and the residue purified by preparative chromatography to give 3.8 mg of the title compound. HPLC retention time: 2.539 min (Method A). Mass spec: 496 (M+H$^+$).

EXAMPLE 166

N-[6-[1,4-Dihydro-7-methoxy-6-(5-oxazolyl)-4-oxo-2-quinolinyl]-2,3-dihydro-1H-inden-1-yl]-N-methyl-4-morpholineacetamide

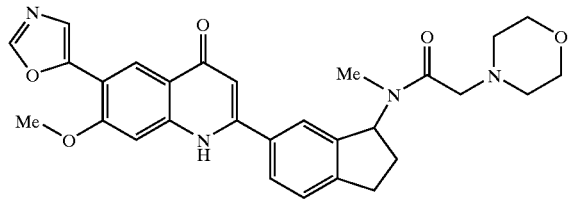

166 was prepared from 163A (20 mg, 0.052 mmol) and morpholine (10.8 µL, 0.1 mmol) using the same procedure as 165 to give 0.9 mg of the title compound. HPLC retention time: 2.526 min (Method A). Mass spec: 515 (M+H$^+$).

EXAMPLE 167

N-[6-[1,4-Dihydro-7-methoxy-6-(5-oxazolyl)-4-oxo-2-quinolinyl]-2,3-dihydro-1H-inden-1-yl]-N-methyl-2H-1,2,3-triazole-2-acetamide

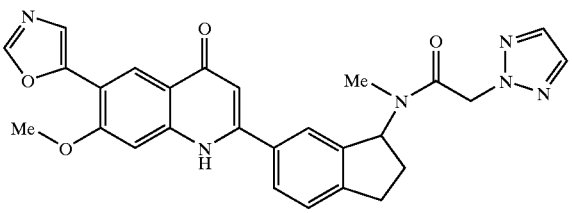

157 was prepared from 163A (39.7 mg, 0.102 mmol) and triazole (17.7 mg, 0.256 mmol) using the same procedure as 165 to give 7.8 mg of the title compound. HPLC retention time: 2.726 min (Method A). Mass spec: 497 (M+H$^+$).

EXAMPLE 168

N-[6-[1,4-Dihydro-7-methoxy-6-(5-oxazolyl)-4-oxo-2-quinolinyl]-2,3-dihydro-1H-inden-1-yl]-N-methyl-1H-1,2,3-triazole-1-acetamide

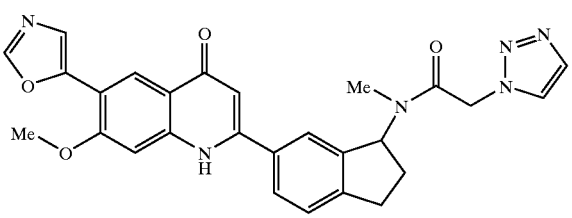

168 was prepared from 163A (39.7 mg, 0.102 mmol) and triazole (17.7 mg, 0.256 mmol) using the same procedure as 165 to give 15.4 mg of the title compound. HPLC retention time: 2.659 min (Method A). Mass spec: 497 (M+H$^+$).

EXAMPLE 169

[6-[1,4-Dihydro-7-methoxy-6-(5-oxazolyl)-4-oxo-2-quinolinyl]-2,3-dihydro-1H-inden-1-yl] methylcarbamic acid ethyl ester

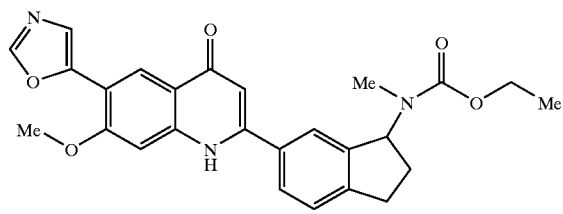

169 was prepared from 163A (25 mg, 0.059 mmol) and ethylchloroformate (5.6 µL, 0.059 mmol) using the same procedure as 164 to give 2.8 mg of the title compound. HPLC retention time: 3.202 min (Method A). Mass spec: 460 (M+H$^+$).

EXAMPLE 170

Dimethylcarbamic acid 6-[1,4-dihydro-7-methoxy-6-(5-oxazolyl)-4-oxo-2-quinolinyl]-2,3-dihydro-1H-inden-1-yl ester

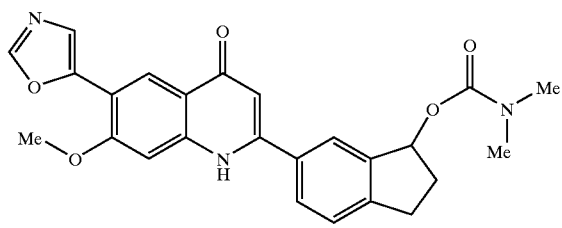

To 163A (15 mg, 0.04 mmol) in DMF (1 mL) was added NaH (2.4 mg, 0.1 mmol) at room temperature. The mixture was stirred for 10 min then cooled in −78° C. bath and dimethylcarbamyl chloride (3.7 μL, 0.04 mmol) in DMF (1 mL) was added. The reaction was slowly brought to room temperature and stirred for 18 h. The reaction was quenched with 1 drop of acetic acid and the solvent removed in vacuo. Water was added and the precipitate filtered and rinsed with water to give 11.3 mg. HPLC retention time: 3.108 min (Method A). Mass spec: 446 (M+H$^+$).

EXAMPLE 171

2-[2,3-Dihydro-1-(1-pyrrolidinyl)-1H-inden-5-yl]-7-methoxy-6-(5-oxazolyl)-4(1H)-quinolinone

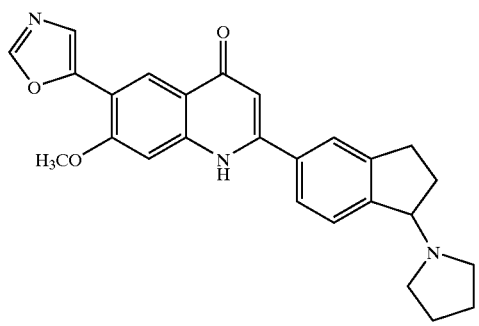

This compound was prepared analogous to 127 starting from 5-bromo-1-chloro-indane and using pyrrolidine instead of dimethylamine. LC-MS: HPLC conditions A, retention time=2.53 minutes, m/z 428.15 (M+H)$^+$.

EXAMPLE 172

4-Acetyl-6-[1,4-dihydro-7-methoxy-6-(5-oxazolyl)-4-oxo-2-quinolinyl]-3,4-dihydro-2H-1,4-benzoxazine

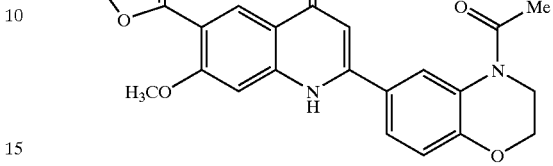

This compound was prepared in an analogous fashion to method C2. LC-MS: HPLC conditions E, retention time= 2.72 minutes, m/z 418.12 (M+H)$^+$.

EXAMPLE 173

1,2,3,4-Tetrahydro-6-methoxy-7-(5-oxazolyl)-9H-cyclopenta[b]quinolin-9-one

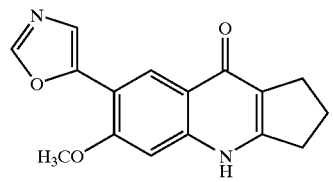

This compound was prepared in an analogous fashion to method A2. LC-MS: HPLC conditions E, retention time= 2.25 minutes, m/z 283.15 (M+H)$^+$.

EXAMPLE 174

7-Methoxy-2-[4-(4-morpholinylmethyl)phenyl]-6-(5-oxazolyl)-4(1H)-quinolinone

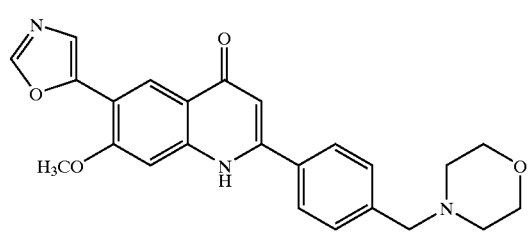

This compound was prepared in an analogous fashion to method A3. LC-MS: HPLC conditions E, retention time= 1.86 minutes, m/z 418.23 (M+H)$^+$.

Obviously, numerous modifications and variations of the present invention are possible in light of the above teachings. It is therefore to be understood that within the scope of the appended claims, the invention may be practiced otherwise than as specifically described herein.

What is claimed is:

1. A compound of formula (I)

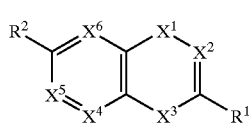

(I)

or enantiomers, diastereomers, tautomers, pharmaceutically acceptable salts and solvates thereof wherein:
$X^1$ is C=O;
$X^2$ is $CR^3$;
$X^3$ is —NH—;
$X^4$ is $CR^4$;
$X^5$ is $CR^5$;
$X^6$ is $CR^6$;
$R^1$ is alkyl, substituted alkyl, alkenyl, substituted alkenyl, alkynyl, substituted alkynyl, cycloalkyl, substituted cycloalkyl, aryl, substituted aryl, heterocycloalkyl, or heteroaryl;
$R^2$ is a substituted or unsubstituted monocyclic heteroaryl group;
$R^3$ is hydrogen, hydroxy, halogen, cyano, $CO_2R^7$, $NR^8R^9$, alkyl, substituted alkyl, alkenyl, substituted alkenyl, alkynyl, substituted alkynyl, cycloalkyl, substituted cycloalkyl, aryl, substituted aryl, heterocycloalkyl or heteroaryl;
$R^4$, $R^5$, and $R^6$ are independently selected from the group consisting of hydrogen, halogen, nitro, cyano, O—$R^7$, $NR^8R^9$, $SR^7$, $S(O)R^7$, $SO_2R^7$, $SO_3R^7$, $SO_2NR^8R^9$, $CO_2R^7$, $C(O)NR^8R^9$, C(O)alkyl, C(O) substituted alkyl, alkyl, substituted alkyl, alkenyl, substituted alkenyl, alkynyl and substituted alkynyl;
$R^7$, $R^{10}$, and $R^{11}$, are independently selected from the group consisting of hydrogen, alkyl, substituted alkyl, alkenyl, alkynyl, cycloalkyl, substituted cycloalkyl, C(O)alkyl, C(O)substituted alkyl, C(O)cycloalkyl, C(O) substituted cycloalkyl, C(O)aryl, C(O)substituted aryl, C(O)Oalkyl, C(O)Osubstituted alkyl, C(O)heterocycloalkyl, C(O)heteroaryl, aryl, substituted aryl, heterocycloalkyl and heteroaryl; and
$R^8$ and $R^9$ are independently selected from the group consisting of hydrogen, alkyl, substituted alkyl, cycloalkyl, substituted cycloalkyl, alkenyl, alkynyl, C(O)alkyl, C(O)substituted alkyl, C(O)cycloalkyl, C(O)substituted cycloalkyl, C(O)aryl, C(O) substituted aryl, C(O)Oalkyl, C(O)Osubstituted alkyl, C(O)heterocycloalkyl, C(O)heteroaryl, aryl, substituted aryl, heterocycloalkyl, and heteroaryl or $R^8$ and $R^9$ taken together with the nitrogen atom to which they are attached complete a heterocycloalkyl or heteroaryl ring with the following proviso:

(c) when $R^2$ is heteroaryl, at least one of the heteroatoms must be O.

2. A compound of claim 1 of formula (III)

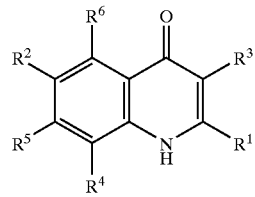

(III)

or enantiomers, diastereomers, tautomers, pharmaceutically acceptable salts and solvates thereof wherein:
$R^2$ is 4-oxazolyl, substituted 4-oxazolyl, 5-oxazolyl, or substituted 5-oxazolyl;
$R^3$ is hydrogen, hydroxy, $NR^8R^9$, alkyl of 1 to 4 carbons, alkenyl of 2 to 4 carbons, alkynyl of 2 to 4 carbons, substituted alkyl of 1 to 4 carbons, phenyl, substituted phenyl, cycloalkyl of 5 to 7 carbons, substituted cycloalkyl of 5 to 7 carbons, monocyclic heterocycloalkyl and monocyclic heteroaryl;
$R^4$ is hydrogen, halogen, nitro, hydroxy, alkyl of 1 to 4 carbons, cyano, $CF_3$, $OCF_3$, $OCH_3$, $SCH_3$, $S(O)CH_3$, or $S(O)_2CH_3$;
$R^5$ is hydrogen, halogen, nitro, hydroxy, alkyl of 1 to 4 carbons, cyano, vinyl, $CF_3$, $CF_2CF_3$, CH=$CF_2$, $OCH_3$, $OCF_3$, $OCHF_2$, $SCH_3$, $S(O)CH_3$, or $S(O)_2CH_3$; and
$R^6$ is hydrogen, halogen, nitro, hydroxy, alkyl of 1 to 4 carbons, cyano, $CF_3$, $OCH_3$, $OCF_3$, $SCH_3$, $S(O)CH_3$, and $S(O)_2CH_3$.

3. A compound of claim 2 or enantiomers, diastereomers, tautomers, pharmaceutically acceptable salts and solvates thereof
wherein:
$R^2$ is 4-oxazolyl, substituted 4-oxazolyl, 5-oxazolyl, or substituted 5-oxazolyl;
$R^3$ is hydrogen, hydroxy, halogen, methyl or $NR^8R^9$;
$R^4$ is hydrogen;
$R^5$ is halogen, methyl, ethyl, substituted alkenyl, alkyne, OMe or $OCF_3$; and
$R^6$ is hydrogen.

4. A compound of claim 3 or enantiomers, diastereomers, tautomers, pharmaceutically acceptable salts and solvates thereof wherein:
$R^2$ is 4-oxazolyl, substituted 4-oxazolyl, 5-oxazolyl or substituted 5-oxazolyl;
$R^3$ is hydrogen, hydroxy, halogen or methyl;
$R^4$ is hydrogen;
$R^5$ is halogen, methyl or OMe; and
$R^6$ is hydrogen.

5. A compound of claim 1 of formula (V)

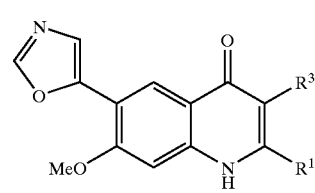

(V)

or enantiomers, diastereomers, tautomers, pharmaceutically acceptable salts and solvates thereof selected from:

a compound of formula (V) wherein:
R¹ is

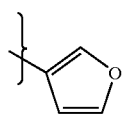

and R³ is hydrogen;
a compound of formula (V) wherein:
R² is

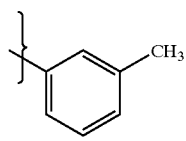

and R³ is hydrogen;
a compound of formula (V) wherein:
R¹ is

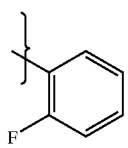

and R³ is hydrogen;
a compound of formula (V) wherein:
R¹ is CH₃ and R³ is hydrogen;
a compound of formula (V) wherein:

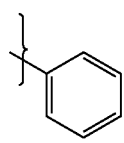

and R³ is CH₃;
a compound of formula (V) wherein:
R¹ is

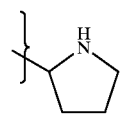

and R³ is hydrogen;
a compound of formula (V) wherein:
R¹ is

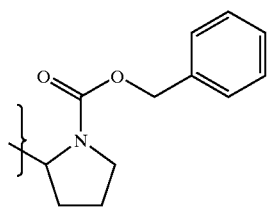

and R³ is hydrogen;

a compound of formula (V) wherein:
R¹ is

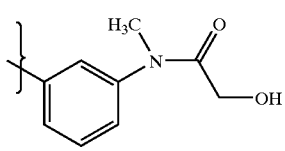

and R³ is hydrogen;
a compound of formula (V) wherein:
R¹ is

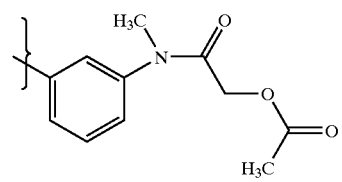

and R³ is hydrogen;
a compound of formula (V) wherein:
R¹ is

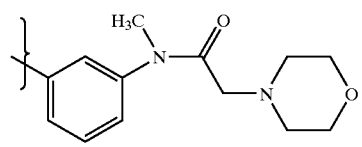

and R³ is hydrogen;
a compound of formula (V) wherein:
R¹ is

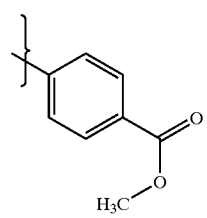

and R³ is hydrogen;
a compound of formula (V) wherein:
R¹ is

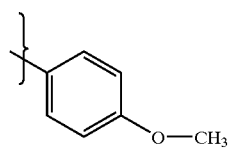

and R³ is hydrogen;

a compound of formula (V) wherein:
 R¹ is

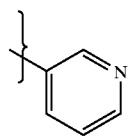

and R³ is hydrogen;

a compound of formula (V) wherein:
 R¹ is

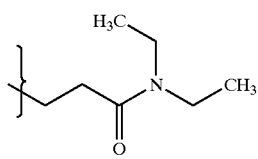

and R³ is hydrogen;

a compound of formula (V) wherein:
 R¹ is

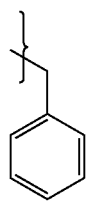

and R³ is hydrogen;

a compound of formula (V) wherein:
 R¹ is

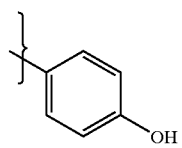

and R³ is hydrogen;

a compound of formula (V) wherein:
 R¹ is

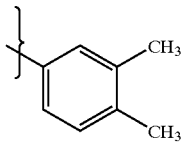

and R³ is hydrogen;

a compound of formula (V) wherein:
 R¹ is

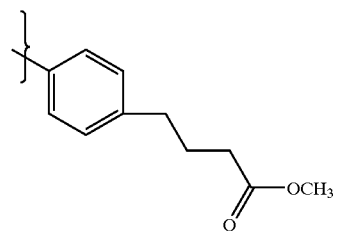

and R³ is hydrogen;

a compound of formula (V) wherein:
 R¹ is

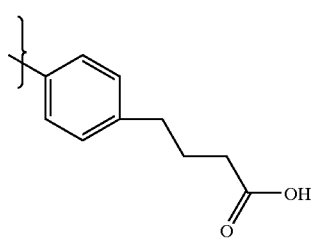

and R³ is hydrogen;

a compound of formula (V) wherein:
 R¹ is

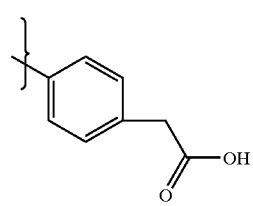

and R³ is hydrogen;

a compound of formula (V) wherein:
 R¹ is

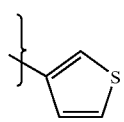

and R³ is hydrogen;

a compound of formula (V) wherein:
 R¹ is

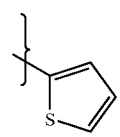

and R³ is hydrogen;

a compound of formula (V) wherein:
R¹ is

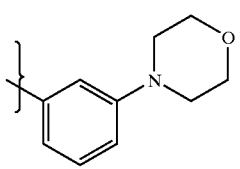

and R³ is hydrogen;
a compound of formula (V) wherein:
R¹ is

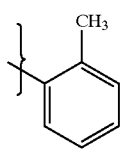

and R³ is hydrogen;
a compound of formula (V) wherein:
R¹ is

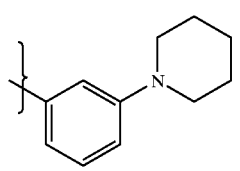

and R³ is hydrogen;
a compound of formula (V) wherein:
R¹ is

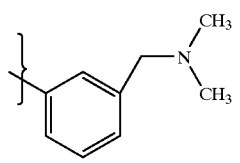

and R³ is hydrogen;
a compound of formula (V) wherein:
R¹ is

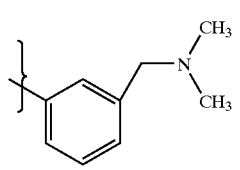

and R³ is Br;

a compound of formula (V) wherein:
R¹ is

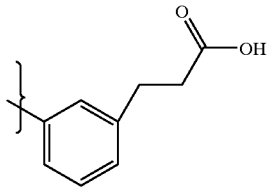

and R³ is hydrogen;
a compound of formula (V) wherein:
R¹ is

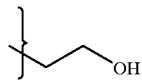

and R³ is hydrogen;
a compound of formula (V) wherein:
R¹ is

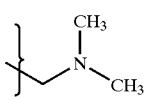

and R³ is hydrogen;
a compound of formula (V) wherein:
R¹ is

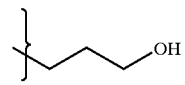

and R³ is hydrogen;
a compound of formula (V) wherein:
R¹ is

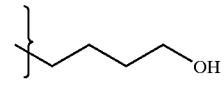

and R³ is hydrogen;
a compound of formula (V) wherein:
R¹ is

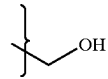

and R³ is hydrogen;
a compound of formula (V) wherein:
R¹ is

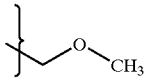

and R³ is hydrogen;

a compound of formula (V) wherein:
R¹ is

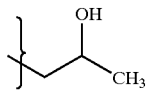

and R³ is hydrogen;
a compound of formula (V) wherein:
R¹ is

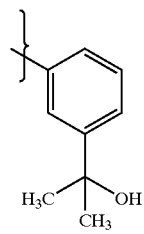

and R³ is hydrogen;
a compound of formula (V) wherein:
R¹ is

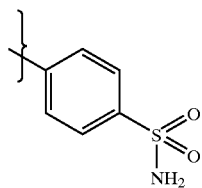

and R³ is hydrogen;
a compound of formula (V) wherein:
R¹ is

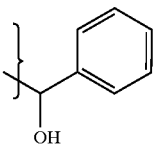

and R³ is hydrogen;
a compound of formula (V) wherein:
R¹ is

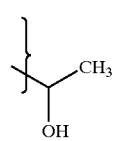

and R³ is hydrogen;

a compound of formula (V) wherein:
R¹ is

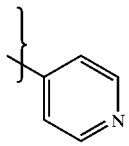

and R³ is hydrogen;
a compound of formula (V) wherein:
R¹ is

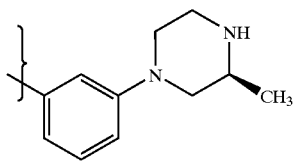

and R³ is hydrogen;
a compound of formula (V) wherein:
R¹ is

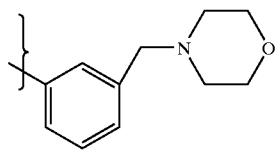

and R³ is hydrogen;
a compound of formula (V) wherein:
R¹ is

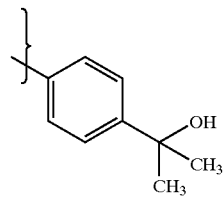

and R³ is hydrogen;
a compound of formula (V) wherein:
R¹ is

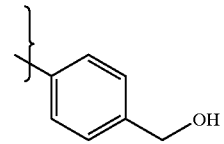

and R³ is hydrogen;

a compound of formula (V) wherein:
R¹ is

[3-(4-methoxybenzyloxy)phenyl group]

and R³ is hydrogen;

a compound of formula (V) wherein:
R¹ is

[3-hydroxyphenyl group]

and R³ is hydrogen;

a compound of formula (V) wherein:
R¹ is

[3-(2-(dimethylamino)ethoxy)phenyl group]

and R³ is hydrogen;

a compound of formula (V) wherein:
R¹ is

[2-methyl-2,3-dihydro-1H-isoindol-5-yl group]

and R³ is hydrogen;

a compound of formula (V) wherein:
R¹ is

[thiazol-4-yl group]

and R³ is hydrogen;

a compound of formula (V) wherein:
R¹ is

[2-(piperidin-1-yl)thiazol-4-yl group]

and R³ is hydrogen;

a compound of formula (V) wherein:
R¹ is

[3,5-dimethylphenyl group]

and R³ is hydrogen;

a compound of formula (V) wherein:
R¹ is

[3-(methylthio)phenyl group]

and R³ is hydrogen;

a compound of formula (V) wherein:
R¹ is

[3-(methylsulfonyl)phenyl group]

and R³ is hydrogen;

a compound of formula (V) wherein:
R¹ is

[3-(4-(2-methoxyethyl)piperazin-1-yl)phenyl group]

and R³ is hydrogen;

a compound of formula (V) wherein:
R¹ is

[3-(2,6-dimethylmorpholin-4-yl)phenyl group]

and R³ is hydrogen;

a compound of formula (V) wherein:
R¹ is

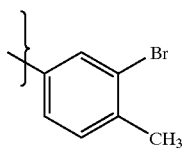

and R³ is hydrogen;
a compound of formula (V) wherein:
R¹ is

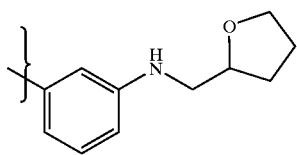

and R³ is hydrogen;
a compound of formula (V) wherein:
R¹ is

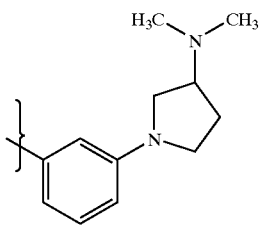

and R³ is hydrogen;
a compound of formula (V) wherein:
R¹ is

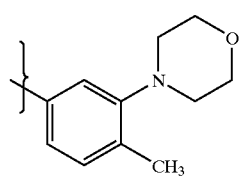

and R³ is hydrogen;
a compound of formula (V) wherein:
R¹ is

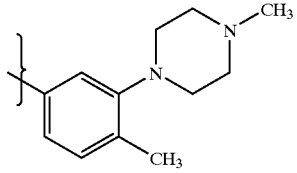

and R³ is hydrogen;

a compound of formula (V) wherein:
R¹ is

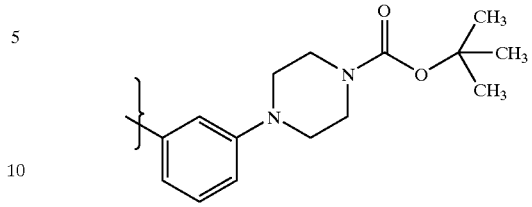

and R³ is hydrogen;
a compound of formula (V) wherein:
R¹ is

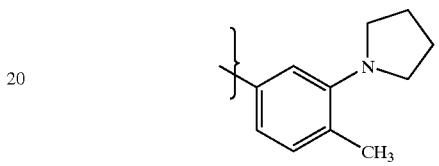

and R³ is hydrogen;
a compound of formula (V) wherein:
R¹ is

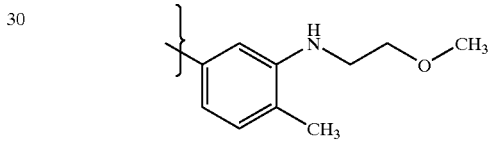

and R³ is hydrogen;
a compound of formula (V) wherein:
R¹ is

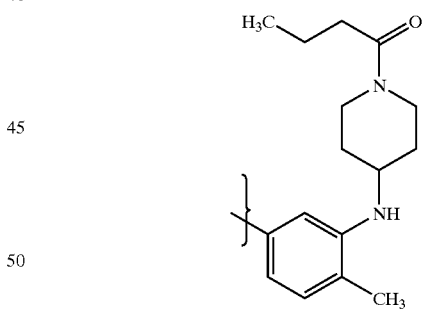

and R³ is hydrogen;
a compound of formula (V) wherein:
R¹ is

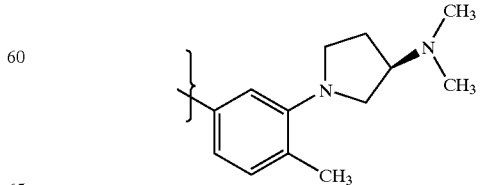

and R³ is hydrogen;

a compound of formula (V) wherein:
R¹ is

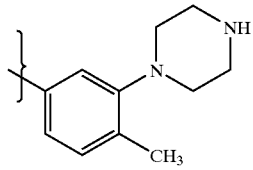

and R³ is hydrogen;

a compound of formula (V) wherein:
R¹ is

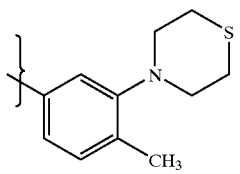

and R³ is hydrogen;

a compound of formula (V) wherein:
R¹ is

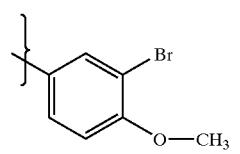

and R³ is hydrogen;

a compound of formula (V) wherein:
R¹ is

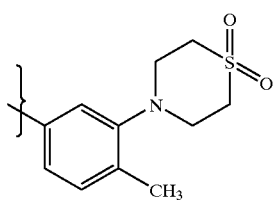

and R³ is hydrogen;

a compound of formula (V) wherein:
R¹ is

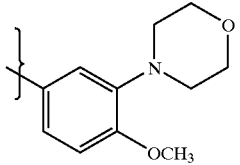

and R³ is hydrogen;

a compound of formula (V) wherein:
R¹ is

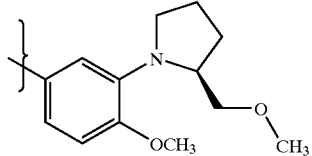

and R³ is hydrogen;

a compound of formula (V) wherein:
R¹ is

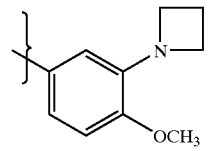

and R³ is hydrogen;

a compound of formula (V) wherein:
R¹ is

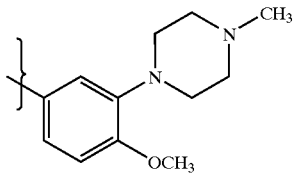

and R³ is hydrogen;

a compound of formula (V) wherein:
R¹ is

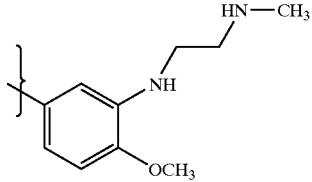

and R³ is hydrogen;

a compound of formula (V) wherein:
R¹ is

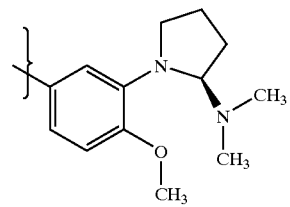

and R³ is hydrogen;

a compound of formula (V) wherein:
  R¹ is

[structure: phenyl with NH-CH2CH2-O-CH3 and OCH3 substituents]

and R³ is hydrogen;

a compound of formula (V) wherein:
  R¹ is

[structure: phenyl with NH-CH2CH2-morpholine and OCH3 substituents]

and R³ is hydrogen;

a compound of formula (V) wherein:
  R¹ is

[structure: phenyl with CN and CH3 substituents]

and R³ is hydrogen;

a compound of formula (V) wherein:
  R¹ is

[structure: tetralone (7-substituted-1-oxo-tetrahydronaphthalene)]

and R³ is hydrogen;

a compound of formula (V) wherein:
  R¹ is

[structure: 7-substituted-1-hydroxy-tetrahydronaphthalene]

and R³ is hydrogen;

a compound of formula (V) wherein:
  R¹ is

[structure: 7-substituted tetrahydronaphthalene-1-yl N,N-dimethylcarbamate]

and R³ is hydrogen;

a compound of formula (V) wherein:
  R¹ is

[structure: 7-substituted-1-(N,N-dimethylamino)-tetrahydronaphthalene]

and R³ is hydrogen;

a compound of formula (V) wherein:
  R¹ is

[structure: -CH2CH3 (ethyl)]

and R³ is hydrogen;

a compound of formula (V) wherein:
  R¹ is

[structure: 3-(trifluoromethyl)phenyl]

and R³ is hydrogen;

a compound of formula (V) wherein:
  R¹ is

[structure: 4-(trifluoromethyl)phenyl]

and R³ is hydrogen;

a compound of formula (V) wherein:
 R¹ is

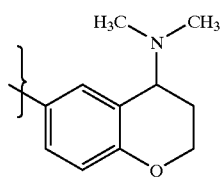

and R³ is hydrogen;

a compound of formula (V) wherein:
 R¹ is

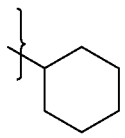

and R³ is hydrogen;

a compound of formula (V) wherein:
 R¹ is

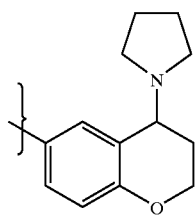

and R³ is hydrogen;

a compound of formula (V) wherein:
 R¹ is

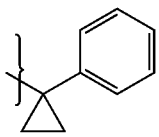

and R³ is hydrogen;

a compound of formula (V) wherein:
 R¹ is

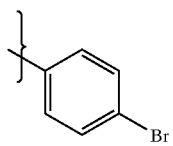

and R³ is hydrogen;

a compound of formula (V) wherein:
 R¹ is

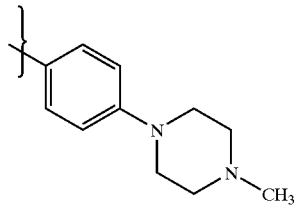

and R³ is hydrogen;

and a compound of formula (V) wherein:
 R¹ is

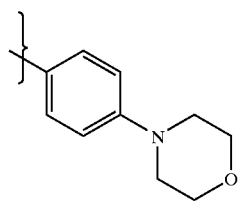

and R³ is hydrogen.

6. A compound of claim 1 or enantiomers, diastereomers, tautomers, pharmaceutically acceptable salts and solvates thereof selected from:

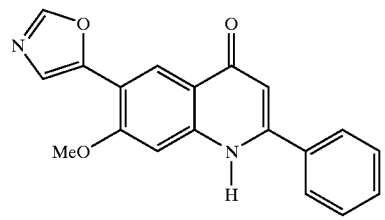

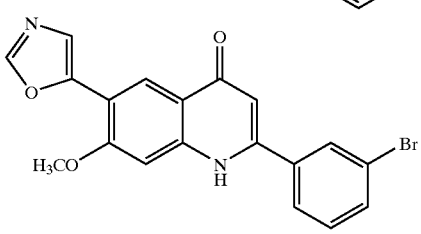

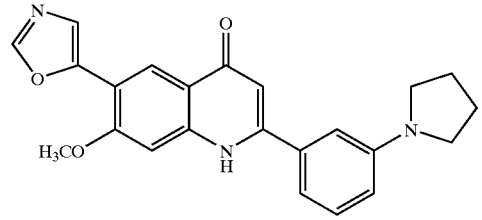

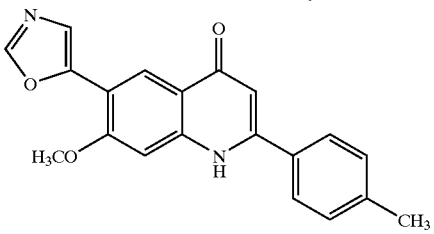

-continued

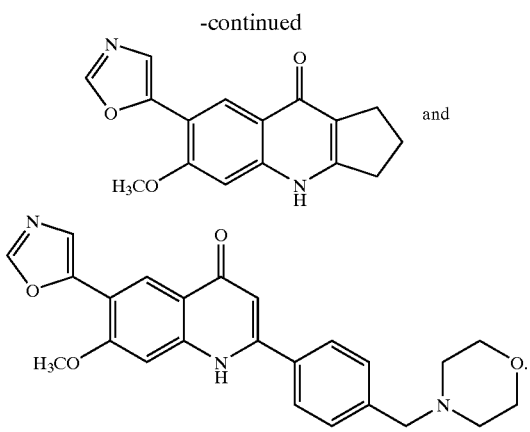

and

7. A pharmaceutical composition comprising a compound of claim 1 and a pharmaceutically acceptable carrier.

8. A pharmaceutical composition comprising a compound of claim 2 and a pharmaceutically acceptable carrier.

9. A pharmaceutical composition comprising a compound of claim 3 and a pharmaceutically acceptable carrier.

10. A pharmaceutical composition comprising a compound of claim 4 and a pharmaceutically acceptable carrier.

11. A pharmaceutical composition comprising a compound of claim 5 and a pharmaceutically acceptable carrier.

12. A pharmaceutical composition comprising a compound claim 6 and a pharmaceutically acceptable carrier.

13. A method of treating inosine monophosphate dehydrogenase associated disorders selected from inflammatory bowel disease, hepatitis B, hepatitis C, herpes simplex I, herpes simplex II, rheumatoid arthritis, asthma, and transplant rejection comprising: administering to a subject a therapeutically effective amount of a compound of claim 1.

14. A method of treating inosine monophosphate dehydrogenase associated disorders selected from inflammatory bowel disease, hepatitis B, hepatitis C, herpes simplex I, herpes simplex II, rheumatoid arthritis, asthma, and transplant rejection comprising: administering to a subject a therapeutically effective amount of a compound of claim 2.

15. A method of treating inosine monophosphate dehydrogenase associated disorders selected from inflammatory bowel disease, hepatitis B, hepatitis C, herpes simplex I, herpes simplex II, rheumatoid arthritis, asthma, and transplant rejection comprising: administering to a subject a therapeutically effective amount of a compound of claim 3.

16. A method of treating inosine monophosphate dehydrogenase associated disorders selected from inflammatory bowel disease, hepatitis B, hepatitis C, herpes simplex I, herpes simplex II, rheumatoid arthritis, asthma, and transplant rejection comprising: administering to a subject a therapeutically effective amount of a compound of a phosphodiesterase Type 4 inhibitor and a compound of claim 1.

17. A method for the treatment or prevention of allograft rejection comprising: administering a therapeutically effective amount of a phosphodiesterase Type 4 inhibitor and a compound of claim 1.

18. A method of claim 16 wherein: the phosphodiesterase Type 4 inhibitor is [4-[3-(cyclopentyloxy)-4-methoxyphenyl]-2-pyrrolidinone].

19. A method of treating inosine monophosphate dehydrogenase associated disorders selected from inflammatory bowel disease, hepatitis B, hepatitis C, herpes simplex I, herpes simplex II, rheumatoid arthritis, asthma, and transplant rejection comprising: administering to a subject a therapeutically effective amount of a compound of claim 7.

20. A method of treating inosine monophosphate dehydrogenase associated disorders selected from inflammatory bowel disease, hepatitis B, hepatitis C, herpes simplex I, herpes simplex II, rheumatoid arthritis, asthma and transplant rejection comprising: administering to a subject a therapeutically effective amount of a compound of claim 7 and another agent known to be useful in treatment of such disorders.

21. A method of treating inosine monophosphate dehydrogenase associated disorders selected from inflammatory bowel disease, hepatitis B, hepatitis C, herpes simplex I, herpes simplex II, rheumatoid arthritis, asthma, and transplant rejection comprising: administering to a subject a therapeutically effective amount of a compound of claim 7 and a phosphodiesterase Type 4 inhibitor.

22. A method for the treatment or prevention of allograft rejection comprising: administering a therapeutically effective amount of the pharmaceutical composition of claim 7 and a phosphodiesterase Type 4 inhibitor.

* * * * *